(12) United States Patent
Bold et al.

(10) Patent No.: US 6,514,974 B2
(45) Date of Patent: Feb. 4, 2003

(54) PYRIDO-, PYRIMIDO-, PYRIDAZO- AND PYRAZO- PYRIDAZINES HAVING ANGIOGENESIS INHIBITING ACTIVITY

(75) Inventors: Guido Bold, Gipf-Oberfrick (CH); Jörg Frei, Hölstein (CH); Peter Traxler, Schönenbuch (CH); Karl-Heinz Altmann, Reinach (CH); Helmut Mett, Neuenburg (DE); David Raymond Stover, Wilmington, MA (US); Jeanette Marjorie Wood, Biel-Benken (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/859,858

(22) Filed: May 17, 2001

(65) Prior Publication Data

US 2002/0091261 A1 Jul. 11, 2002

Related U.S. Application Data

(62) Division of application No. 09/367,273, filed as application No. PCT/EP98/00764 on Oct. 20, 1999, now Pat. No. 6,258,812.

(30) Foreign Application Priority Data

Feb. 13, 1997 (CH) ................................. 315-97

(51) Int. Cl.⁷ ..................... A61K 31/50; C07D 401/00; C07D 237/00
(52) U.S. Cl. .................. 514/252.03; 544/238; 544/237; 544/268
(58) Field of Search ...................... 514/252.03; 544/238, 544/237, 268

(56) References Cited

U.S. PATENT DOCUMENTS 2,960,504 A 11/1960 Druey et al. ................... 544/23
6,258,812 B1 * 7/2001 Bold et al. ............. 514/252.03

FOREIGN PATENT DOCUMENTS

AU 5184293 6/1994

(List continued on next page.)

OTHER PUBLICATIONS

Chemical Abstracts 115: 256197S (1991).
Haworth R.D. et al., J.Chem.Soc., pp. 777–782 (1948).
Michael P. Seed, Exp.Opin.Invest.Drugs, vol. 5, No. 12, pp. 1617–1637 (1996).
Yamaguchi M. et al., J.Med.Chem., vol. 36, pp. 4052–4060 (1993).
Wagaw S. et al., J.Org.Chem., vol. 61, pp. 7240–7241 (1996).
Chemical Abstracts 38: 8761f.
Derwent Abstract 11584T–B.

(List continued on next page.)

Primary Examiner—Mukund J. Shah
Assistant Examiner—Sudhaker B. Patel
(74) Attorney, Agent, or Firm—Joseph J. Borovian

(57) ABSTRACT

The invention relates to compounds of formula I,

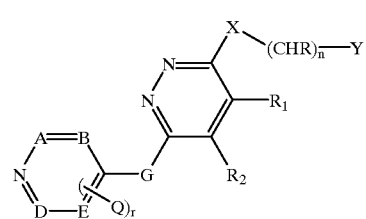

(I)

wherein r is 0 to 2, n is 0 to 2; m is 0 to 4; $R_1$ and $R_2$ (i) are in each case a lower alkyl, or (ii) together form a bridge in subformula I*

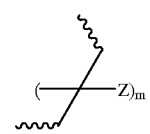

(I*)

or (iii) together form a bridge in subformula I**

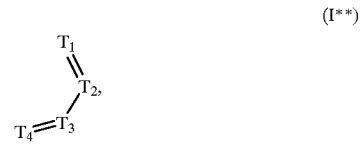

(I**)

wherein one or two of the ring members $T_1$, $T_2$, $T_3$, and $T_4$ are nitrogen, and the remainder are in each case CH; A, B, D, and E are N or CH, wherein not more than 2 of these radicals are N; G is lower alkylene, acyloxy- or hydroxy-lower alkylene, —$CH_2$—O—, —$CH_2$—S—, —$CH_2$—NH—, oxa, thia, or imino; Q is methyl; R is H or lower alkyl; X is imino, oxa, or thia; Y is aryl, pyridyl, or (un)substituted cycloalkyl; and Z is mono- or disubstited amino, halogen, alkyl, substituted alkyl, hydroxy, etherified or esterified hydroxy, nitro, cyano, carboxy, esterified carboxy, alkanoyl, carbamoyl, N-mono- or N,N-disubstituted carbamoyl, amidino, guanidino, mercapto, sulfo, phenylthio, phenyl-lower alkylthio, alkylphenylthio, phenylsulfinyl, phenyl-lower alkylsulfinyl, alkylphenylsulfinyl, phenylsulfonyl, phenyl-lower alkylsulfonyl, or alkylphenylsulfony; and wherein the bonds characterized by a wavy line are either single or double bonds; or an N-oxide of said compound with the stipulation that, if Y is pyridyl or unsubstituted cycloalkyl, X is imino, and the remaining radicals are as defined, then G is selected from the group comprising lower alkylene, —$CH_2$—O—, —$CH_2$—S—, oxa and thia; or a salt thereof. The compounds inhibit angiogenesis.

8 Claims, No Drawings

FOREIGN PATENT DOCUMENTS

| | | | |
|---|---|---|---|
| DE | 10 61 788 B | | 7/1959 |
| DE | 1061788 | * | 7/1959 |
| DE | 20 21 195 A | | 11/1970 |
| EP | 600 831 A | | 6/1994 |
| EP | 722 936 A | | 7/1996 |
| GB | 871 753 | | 6/1961 |
| GB | 1094044 | | 12/1967 |
| GB | 1133406 | | 11/1968 |
| GB | 1293565 | | 10/1972 |
| WO | WO 97 26258 A | | 7/1997 |
| WO | WO 97/40020 | | 10/1997 |

OTHER PUBLICATIONS

Chemical Abstracts 55: 11654h.
Derwent Abstract 95–325541/42.
Michael P. Seed, Exp.Opin.Invest.Drugs, vol. 5, No. 12, pp. 1617–1637 (1996).
Derwent Abstract 91–175139/24.
Derwent Abstract 91/175141/24.
Yamaguchi M. et al., J.Med.Chem., vol. 36, pp. 4052–4060 (1993).
Wagaw S. et al., J.Org.Chem., vol. 61, pp. 7240–7241 (1996).
Derwent Abstract 83345R.

* cited by examiner

PYRIDO-, PYRIMIDO-, PYRIDAZO- AND PYRAZO- PYRIDAZINES HAVING ANGIOGENESIS INHIBITING ACTIVITY

This is a divisional of U.S. application Ser. No. 09/367,273 having a 35 USC 371 date of Oct. 20, 1999, now issued as U.S. Pat. No. 6,258,812, which is a 371 of International Application No. PCT/EP 98/00764, filed Feb. 11, 1998.

The invention relates to the use of phthalazine derivatives—alone or in combination with one or more other pharmaceutically active compounds—for the treatment especially of a proliferative disease, such as a tumour disease, a method for the treatment of such disease in animals, especially in humans, and the use of such a compound—alone or in combination with one or more other pharmaceutically active compounds—for manufacture of a pharmaceutical preparation (medicament) for the treatment especially of a proliferative disease, such as a tumour; to certain of these compounds for use in the treatment of the animal or human body; to new phthalazine derivatives; and to processes for the preparation thereof.

BACKGROUND OF THE INVENTION

Two processes, the de novo formation of vessels from differentiating endothelial cells or angioblasts in the developing embryo (vasculogenesis) and the growth of new capillary vessels from existing blood vessels (angiogenesis), are involved in the development of the vascular systems of animal organs and tissues. Transient phases of new vessel formation (neovascularization) also occur in the adult body, for example during the menstrual cycle, pregnancy, or wound healing.

On the other hand, a number of diseases are known to be associated with deregulated angiogenesis, for example retinopathies, psoriasis, haemangioblastoma, haemangioma, and neoplastic diseases (solid tumours).

The complex processes of vasculogenesis and angiogenesis have been found to involve a whole range of molecules, especially angiogenic growth factors and their endothelial receptors, as well as cell adhesion molecules.

Recent findings show that at the centre of the network regulating the growth and differentiation of the vascular system and its components, both during embryonic development and normal growth and in a wide number of pathological anomalies and diseases, lies the angiogenic factor known as "Vascular Endothelial Growth Factor" (=VGEF), along with its cellular receptors (see Breier, G., et al., Trends in Cell Biology 6, 454–6 [1996] and the references cited therein).

EP 0 722 936 discloses certain phthalazines where n is other than 0 in formula I given below, but doesn't disclose their utility against diseases associated with deregulated angiogenesis. DE 1 061 788 discloses a compound with X=oxa falling under formula I below, bit no medical use. None of the two discloses any compound of formula I given below wherein n=0 and X is imino or thia.

VEGF is a dimeric, disulfide-linked 46-kDa glycoprotein and is related to "Platelet-Derived Growth Factor" (PDGF). It is produced by normal cell lines and tumour cell lines, is an endothelial cell-specific mitogen, shows angiogenic activity in in vivo test systems (e.g. rabbit cornea), is chemotactic for endothelial cells and monocytes, and induces plasminogen activators in endothelial cells, which are then involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PLGF) and VEGF-C.

VEGF receptors by contrast are transmembranous receptor tyrosine kinases. They are characterized by an extracellular domain with seven immunoglobulin-like domains and an intracellular tyrosine kinase domain. Various types of VEGF receptor are known, e.g. VEGFR-1, VEGFR-2, and VEGFR-3.

A large number of human tumours, especially gliomas and carcinomas, express high levels of VEGF and its receptors. This has led to the hypothesis that the VEGF released by tumour cells could stimulate the growth of blood capillaries and the proliferation of tumour endothelium in a paracrine manner and thus, through the improved blood supply, accelerate tumour growth. Increased VEGF expression could explain the occurrence of cerebral oedema in patients with glioma. Direct evidence of the role of VEGF as a tumour angiogenesis factor in vivo has been obtained from studies in which VEGF expression or VEGF activity was inhibited. This was achieved with antibodies which inhibit VEGF activity, with dominant-negative VEGFR-2 mutants which inhibited signal transduction, or with the use of antisense-VEGF RNA techniques. All approaches led to a reduction in the growth of glioma cell lines or other tumour cell lines in vivo as a result of inhibited tumour angiogenesis.

Hypoxia and also a large number of growth factors and cytokines, e.g. Epidermal Growth Factor, Transforming Growth Factor α, Transforming Growth Factor β, Interleukin 1, and Interleukin 6, induce the expression of VEGF in cell experiments. Angiogenesis is regarded as an absolute prerequisite for those tumours which grow beyond a maximum diameter of about 1–2 mm; up to this limit, oxygen and nutrients may be supplied to the tumour cells by diffusion. Every tumour, regardless of its origin and its cause, is thus dependent on angiogenesis for its growth after it has reached a certain size.

Three principal mechanisms play an important part in the activity of angiogenesis inhibitors against tumours: 1) Inhibition of the growth of vessels, especially capillaries, into avascular resting tumours, with the result that there is no net tumour growth owing to the balance that is achieved between apoptosis and proliferation; 2) Prevention of the migration of tumour cells owing to the absence of bloodflow to and from tumours; and 3) Inhibition of endothelial cell proliferation, thus avoiding the paracrine growth-stimulating effect exerted on the surrounding tissue by the endothelial cells which normally line the vessels.

The German patent application DE 1 061 788 names generic intermediates for antihypertensives as belonging to the class of phthalazines. No pharmaceutical use for these intermediates has been declared.

SUMMARY OF THE INVENTION

Surprisingly, it has now been found that phthalazine derivatives of formula I, described below, have advantageous pharmacological properties and inhibit, for example, the activity of the VEGF receptor tyrosine kinase and the growth of tumours.

The compounds of formula I permit, for example, an unexpected new therapeutic approach, especially for diseases in the treatment of which, and also for the prevention of which, an inhibition of angiogenesis and/or of the VEGF receptor tyrosine kinase shows beneficial effects.

FULL DESCRIPTION OF THE INVENTION

The compounds comprised in a pharmaceutical formulation preparation or to be used in accordance with the invention are of formula I,

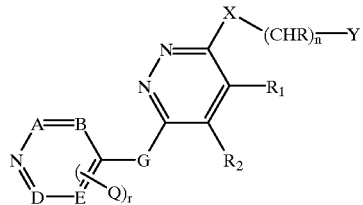

(I)

wherein
r is 0 to 2,
n is 0 to 2,
m is 0 to 4,
$R_1$ and $R_2$
(i) are lower alkyl, especially methyl, or
(ii) together form a bridge in subformula I*

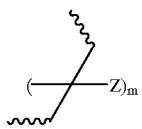

(I*)

the binding being achieved via the two terminal carbon atoms, or
(iii) together form a bridge in subformula I**

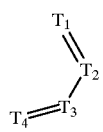

(I**)

wherein one or two of the rings members $T_1$, $T_2$, $T_3$ and $T_4$ are nitrogen, and the others are in each case CH, and the binding is achieved via $T_1$ and $T_4$ A, B, D, and E are, independently of one another, N or CH, with the stipulation that not more than 2 of these radicals are N;

G is lower alkylene, lower alkylene substituted by acyloxy or hydroxy, —$CH_2$—O—, —$CH_2$—S—, —$CH_2$—NH—, oxa (—O—), thia (—S—), or imino (—NH—);

Q is lower alkyl, especially methyl;
R is H or lower alkyl;
X is imino, oxa, or thia;
Y is aryl, pyridyl, or unsubstituted or substituted cycloalkyl; and
Z is mono- or disubstituted amino, halogen, alkyl, substituted alkyl, hydroxy, etherified or esterified hydroxy, nitro, cyano, carboxy, esterified carboxy, alkanoyl, carbamoyl, N-mono- or N,N-disubstituted carbamoyl, amidino, guanidino, mercapto, sulfo, phenylthio, phenyl lower alkylthio, alkylphenylthio, phenylsulfinyl, phenyl-lower alkylsulfinyl, alkylphenylsulfinyl, phenylsulfonyl, phenyl-lower alkylsulfonyl, or alkylphenylsulfonyl, wherein—if more than 1 radical Z (m=≧2) is present—the substituents Z are the same or different from one another, and wherein the bonds characterized, if present, by a wavy line are either single or double bonds;

or an N-oxide of the defined compound, wherein 1 or more N atoms carry an oxygen atom; with the stipulation that, if Y is pyridyl or unsubstituted cycloalkyl, X is imino, and the remaining radicals are as defined, G is selected from the group comprising lower alkylene, —$CH_2$—O—, —$CH_2$—S—, oxa and thia;

or a pharmaceutically acceptable salt thereof.

The general terms used hereinbefore and hereinafter preferably have within the context of this disclosure the following meanings, unless otherwise indicated:

"A pharmaceutical preparation" is one for the treatment of a disease that is associated with deregulated angiogenesis, preferably a disease described herein, especially a proliferative disease, such as a tumour. In a "compound to be used", the use is for the treatment of a diseases that is associated with deregulated angiogenesis, preferably a disease as described herein, especially a proliferative disease, such as a tumour; the use for the manufacture of a pharmaceutical preparation for the treatment of said disease; or a method of use of a compound of formula I, a pharmaceutically acceptable salt thereof or an N-oxide thereof, for the treatment of said disease.

The invention also relates to a compound of formula I, or a pharmaceutically acceptable salt thereof, or an N-oxide thereof, for use in the treatment of a human or animal body, where in said compound n is 0 and any of r, m, $R_1$, $R_2$, A, B, D, E, G, Q, R, X, Y and Z is as defined above or below.

The invention also relates to a compound of the formula I, a salt thereof or an N-oxide thereof, wherein n is 0 and X is imino or thia, and any of r, m, $R_1$, $R_2$, A, B, D, E, G, Q, R, Y and Z is as defined above or below.

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Any asymmetric carbon atoms (for example in compounds of formula I [or an N-oxide thereof], wherein n=1 and R is lower alkyl) may be present in the (R)-, (S)- or (R,S)-configuration, preferably in the (R)- or (S)-configuration. Substituents at a double bond or a ring may be present in cis- (=Z—) or trans (=E—) form. The compounds may thus be present as mixtures of isomers or as pure isomers, preferably as enantiomer-pure diastereomers.

If $R_1$ and $R_2$ together form a bridge in subformula I*, the pertinent compound of formula I has formula IA (compounds of this formula are hereinbefore and hereinafter especially preferred when compounds of formula I are mentioned),

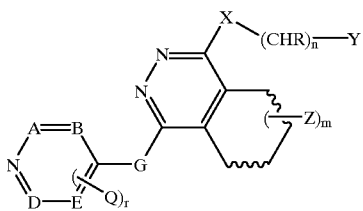

(IA)

wherein the radicals are as defined above for compounds of formula I.

If $R_1$ and $R_2$ together form a bridge in subformula I**, the pertinent compound of formula I has formula IB,

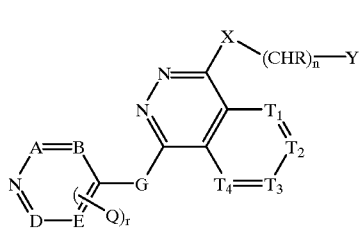

(IB)

wherein the radicals are as defined above for compounds of formula I.

Of the ring members $T_1$, $T_2$, $T_3$ and $T_4$, preferably only one is nitrogen, the remaining three being CH; preferably only $T_3$, especially $T_4$, is nitrogen, whereas the other ring members $T_1$, $T_2$, and $T_4$ or $T_1$, $T_2$, and $T_3$ are CH.

The index r is preferably 0 or 1.

The index n is preferably 0 or 1, especially 0.

The index m is preferably 0, 1, or 2, especially 0 or also 1.

Of ring members A, B, D, and E in formula I, not more than 2 are N, and the remaining ones are CH. Preferably, each of the ring members A, B, D and E are CH.

If G is a bivalent group —$CH_2$—O—, —$CH_2$—S—, or —$CH_2$—NH—, the methylene group in each case is bound to the ring with ring members A, B, D, and E, whereas the heteroatom (O, S, or NH) is bound to the phthalazine ring in formula I.

Lower alkylene G may be branched or preferably linear and is especially branched or preferably linear $C_1$–$C_4$alkylene, especially methylene (—$CH_2$—), ethylene (—$CH_2$—$CH_2$—), trimethylene (—$CH_2$—$CH_2$—$CH_2$—) or tetramethylene (—$CH_2$—$CH_2$—$CH_2$—$CH_2$—). G is preferably methylene.

Acyl in lower alkylene substituted by acyloxy is preferably arylcarbonyloxy, wherein aryl is defined as below, especially benzoyloxy or lower alkanoyloxy, especially benzoyloxy; lower alkylene substituted by acyloxy is especially methylene substituted by benzoyloxy.

Lower alkylene substituted by hydroxy is preferably hydroxymethylene (—CH(OH)—).

G as lower alkylene substituted by acyloxy or hydroxy is preferred, or G as otherwise defined hereinbefore and hereinafter is in each case especially preferred.

Q is preferably bound to A or D (r=1) or to both (r=2), where in the event of binding of Q, A and/or D are/is C(—Q).

Lower alkyl is especially $C_1$–$C_4$-alkyl, e.g. n-butyl, sec-butyl, tert-butyl, n-propyl, isopropyl, or especially methyl or also ethyl.

In the preferred embodiment, aryl is an aromatic radical having 6 to 14 carbon atoms, especially phenyl, naphthyl, fluorenyl or phenanthrenyl, the radicals defined above being unsubstituted or substituted by one or more, preferably up to three, especially one or two substituents, especially selected from amino, mono- or disubstituted amino, halogen, Alkyl, substituted alkyl, hydroxy, etherified or esterified hydroxy, nitro, cyano, carboxy, esterified carboxy, alkanoyl, carbamoyl, N-mono- or N,N-disubstituted carbamoyl, amidino, guanidino, mercapto, sulfo, phenylthio, phenyl-lower alkylthio, alkylphenylthio, phenylsulfinyl, phenyl-lower alkylsulfinyl, alkylphenylsulfinyl, phenylsulfonyl, phenyl-lower alkylsulfonyl, and alkylphenylsulfonyl, or (as an alternative or in addition to the above group of substituents) selected from lower alkenyl, such as ethenyl, phenyl, lower alkylthio, such as methylthio, lower alkanoyl, such as acetyl, lower alkylmercapto, such as methylmercapto (—S—$CH_3$), halogen-lower alkylmercapto, such as trifluoromethylmercapto (—S—$CF_3$), lower alkylsulfonyl, halogen-lower alkylsulfonyl, such as especially trifluoromethane sulfonyl, dihydroxybora (—B(OH)$_2$), heterocyclyl, and lower alkylene dioxy bound at adjacent C-atoms of the ring, such as methylene dioxy; aryl is preferably phenyl which is either unsubstituted or independently substituted by one or two substituents selected from the group comprising amino; lower alkanoylamino, especially acetylamino; halogen, especially fluorine, chlorine, or bromine; lower alkyl, especially methyl or also ethyl or propyl; halogen-lower alkyl, especially trifluoromethyl; hydroxy; lower alkoxy, especially methoxy or also ethoxy; phenyl-lower alkoxy, especially benzyloxy; and cyano, or (as an alternative or in addition to the previous group of substituents) $C_8$–$C_{12}$alkoxy, especially n-decyloxy, carbamoyl, lower alkylcarbamoyl, such as n-methyl- or n-tert-butylcarbamoyl, lower alkanoyl, such as acetyl, phenyloxy, halogen-lower alkyloxy, such as trifluoromethoxy or 1,1,2,2-tetrafluoroethyloxy, lower alkoxycarbonyl, such as ethoxycarbonyl, lower alkylmercapto, such as methylmercapto, halogen-lower alkylmercapto, such as trifluoromethylmercapto, hydroxy-lower alkyl, such as hydroxymethyl or 1-hydroxymethyl, lower alkylsulfonyl, such as methane sulfonyl, halogen-lower alkylsulfonyl, such as trifluoromethane sulfonyl, phenylsulfonyl, dihydroxybora (—B(OH)$_2$), 2-methylpyrimidin-4-yl, oxazol-5-yl, 2-methyl-1,3-dioxolan-2-yl, 1H-pyrazol-3-yl, 1-methyl-pyrazol-3-yl and lower alkylene dioxy bound to two adjacent C-atoms, such as methylene dioxy.

Where mention is made hereinbefore and hereinafter to radicals or substituents as "an alternative or in addition to" the previous group of radicals or substituents, these radicals or substituents and those of the previous group are to be regarded together as one group of substituents from which the respective radicals may be selected, or especially as separate groups. The expression does not mean that one of the radicals following the expression may be added to a member of the previous group by binding. This applies, even if the expression "as an alternative or in addition to" is not mentioned again, for the radicals or substituents, as defined here, in the preferred compounds of formula I defined below.

Mono- or disubstituted amino is especially amino substituted by one or two radicals selected independently of one another from lower alkyl, such as methyl; hydroxy-lower alkyl, such as 2-hydroxyethyl; phenyl-lower alkyl; lower alkanoyl, such as acetyl; benzoyl; substituted benzoyl, wherein the phenyl radical is unsubstituted or especially substituted by one or more, preferably one or two, substituents selected from nitro or amino, or also from halogen, amino, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein the phenyl radical is unsubstituted or especially substituted by one or more, preferably one or two, substituents selected from nitro or amino, or also from halogen, amino, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group comprising benzoylamino and phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl or carbamoyl, or as an alternative or in addition to the previous group of radicals by aminocarbonylamino.

Halogen is especially fluorine, chlorine, bromine, or iodine, especially fluorine, chlorine, or bromine.

In the preferred embodiment, alkyl has up to a maximum of 12 carbon atoms and is especially lower alkyl, especially methyl, or also ethyl, n-propyl, isopropyl, or tert-butyl.

Substituted alkyl is alkyl as last defined, especially lower alkyl, preferably methyl; where one or more, especially up to three, substituents may be present, primarily from the group selected from halogen, especially fluorine, and also from amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred.

Etherified hydroxy is especially $C_8$–$C_{20}$alkyloxy, such as n-decyloxy, lower alkoxy (preferred), such as methoxy, ethoxy, isopropyloxy, or n-pentyloxy, phenyl-lower alkoxy, such as benzyloxy, or also phenyloxy, or as an alternative or in addition to the previous group $C_8$–$C_{20}$alkyloxy, such as n-decyloxy, halogen-lower alkoxy, such as trifluoromethyloxy or 1,1,2,2-tetrafluoroethoxy.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxcarbonyloxy.

Esterified carboxy is especially lower alkoxycarbonyl, such as tert-butoxycarbonyl or ethoxycarbonyl, phenyl-lower alkoxycarbonyl, or phenyloxycarbonyl.

Alkanoyl is primarily alkylcarbonyl, especially lower alkanoyl, e.g. acetyl.

N-mono- or N,N-disubstituted carbamoyl is especially substituted by one or two substituents, lower alkyl, phenyl-lower alkyl, or hydroxy-lower alkyl, at the terminal nitrogen atom.

Alkylphenylthio is especially lower alkylphenylthio.

Alkylphenylsulfinyl is especially lower alkylphenylsulfinyl.

Alkylphenylsulfinyl is especially lower alkylphenylsulfinyl.

Pyridyl Y is preferably 3- or 4-pyridyl.

Z is preferably amino, hydroxy-lower alkylamino, such as 2-hydroxyethylamino, lower alkanoylamino, such as acetylamino, nitrobenzoylamino, such as 3-nitrobenzoylamino, aminobenzoylamino, such as 4-aminobenzoylamino, phenyl-lower alkoxycarbonylamino, such as benzyloxycarbonylamino, or halogen, such as bromine; preferably only one substituent is present (m=1), especially one of the last mentioned, especially halogen. A compound of formula I (or an N-oxide thereof), wherein Z is absent (m=0), is quite especially preferred.

Unsubstituted or substituted cycloalkyl is preferably $C_3$–$C_8$cycloalkyl, which is unsubstituted or substituted in the same way as aryl, especially as defined for phenyl. Cyclohexyl or also cyclopentyl or cyclopropyl are preferred.

Heterocyclyl is especially a five or six-membered heterocyclic system with 1 or 2 heteroatoms selected from the group comprising nitrogen, oxygen, and sulfur, which may be unsaturated or wholly or partly saturated, and is unsubstituted or substituted especially by lower alkyl, such as methyl; a radical selected from 2-methylpyrimidin-4-yl, oxazol-5-yl, 2-methyl-1,3-dioxolan-2-yl, 1H-pyrazol-3-yl, and 1-methyl-pyrazol-3-yl is preferred.

Aryl in the form of phenyl which is substituted by lower alkylene dioxy bound to two adjacent C-atoms, such as methylenedioxy, is preferably 3,4-methylenedioxyphenyl.

The bonds in formula I characterized by wavy lines are present either as single or as double bonds. Preferably both are at the same time either single or double bonds.

An N-oxide of a compound of formula I is preferably an N-oxide in which a phthalazine-ring nitrogen or a nitrogen in the ring with ring members A, B, D, and E carries an oxygen atom, or several of the said nitrogen atoms carry an oxygen atom.

Salts are especially the pharmaceutically acceptable salts of compounds of formula I (or an N-oxide thereof).

Such salts are formed, for example, as acid addition salts, preferably with organic or inorganic acids, from compounds of formula I (or an N-oxide thereof) with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, 2-hydroxybutyric acid, gluconic acid, glucosemonocarboxylic acid, fumaric acid, succinic acid, adipic acid, pimelic acid, suberic acid, azelaic acid, malic acid, tartaric acid, citric acid, glucaric acid, galactaric acid, amino acids, such as glutamic acid, aspartic acid, N-methylglycine, acetylaminoacetic acid, N-acetylasparagine or N-acetylcysteine, pyruvic acid, acetoacetic acid, phosphoserine, 2- or 3-glycerophosphoric acid, glucose-6-phosphoric acid, glucose-1-phosphoric acid, fructose-1,6-bis-phosphoric acid, maleic acid, hydroxymaleic acid, methylmaleic acid, cyclohexanecarboxylic acid, adamantanecarboxylic acid, benzoic acid, salicylic acid, 1- or 3-hydroxynaphthyl-2-carboxylic acid, 3,4,5-trimethoxybenzoic acid, 2-phenoxybenzoic acid, 2-acetoxybenzoic acid, 4-aminosalicylic acid, phthalic acid, phenylacetic acid, mandelic acid, cinnamic acid, glucuronic acid, galacturonic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I (or an N-oxide thereof) may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compounds of formula I (or an N-oxide thereof) have valuable pharmacological properties, as described hereinbefore and hereinafter.

The efficacy of the compounds of the invention as inhibitors of VEGF-receptor tyrosine kinase activity can be demonstrated as follows:

Test for activity against VEGF-receptor tyrosine kinase. The test is conducted using Flt-1 VEGF-receptor tyrosine kinase. The detailed procedure is as follows: 30 µl kinase solution (10 ng of the kinase domain of Flt-1, Shibuya et al., Oncogene 5, 519–24 [1990]) in 20 mM Tris.HCl pH 7.6, 5 mM manganese dichloride ($MnCl_2$), 5 mM magnesium chloride ($MgCl_2$), 1 mM dithiothreitol, 10 µM $Na_3VO_4$ (sodium vanadate), and 30 µg/ml poly(Glu,Tyr) 4:1 (Sigma, Buchs, Switzerland), 8 µM [$^{33}$P]-ATP (0.05 µCi/batch), 1% dimethyl sulfoxide, and 0 to 100 µM of the compound to be tested are incubated together for 15 minutes at room temperature. The reaction is then ended by the addition of 10 µl 0.25 M ethylenediaminetetraacetate (EDTA) pH 7. Using a multichannel dispenser (LAB SYSTEMS, USA), an aliquot of 20 µl is applied to a PVDF (=polyvinyl difluoride) Immobilon P membrane (Millipore, USA), incorporating a Millipore microtiter filter manifold, and connected to a vacuum. Following complete elimination of the liquid, the membrane is washed 4 times successively in a bath containing 0.5% phosphoric acid ($H_3PO_4$), incubated for 10 minutes each time while shaking, then mounted in a Hewlett Packard TopCount Manifold and the radioactivity measured after the addition of 10 µl Microscint® (β-scintillation counter liquid). $IC_{50}$-values are determined by linear regression analysis of the percentages for the inhibition of each compound in three concentrations (as a rule 0.01, 0.1, and 1 µmol).

The antitumour efficacy of the compounds of the invention can be demonstrated in vivo as follows:

In vivo activity in the nude mouse xenotransplant model: female BALB/c nude mice (8–12 weeks old), Novartis Animal Farm, Sisseln, Switzerland) are kept under sterile conditions with water and feed ad libitum. Tumours are induced by subcutaneous injection of tumour cells (human epithelial cell line A-431; American Type Culture Collection (ATCC), Rockville, Md., USA, Catalogue Number ATCC CRL 1555; cell line from an 85-year-old woman; epidermoid carcinoma cell line) into carrier mice. The resulting tumours pass through at least three consecutive transplantations before the start of treatment. Tumour fragments (about 25 mg) are implanted subcutaneously in the left flank of the animals using a 13-gauge trocar needle under Forene® anaesthesia (Abbott, Switzerland). Treatment with the test compound is started as soon as the tumour has reached a mean volume of 100 mm³. Tumour growth is measured two to three times a week and 24 hours after the last treatment by determining the length of two perpendicular axes. The tumour volumes are calculated in accordance with published methods (see Evans et al., Brit. J. Cancer 45, 466–8 [1982]). The antitumour efficacy is determined as the mean increase in tumour volume of the treated animals divided by the mean increase in tumour volume of the untreated animals (controls) and, after multiplication by 100, is expressed as T/C%. Tumour regression (given in %) is reported as the smallest mean tumour volume in relation to the mean tumour volume at the start of treatment. The test compound is administered daily by gavage.

As an alternative to cell line A-431, other cell lines may also be used in the same manner, for example:

the MCF-7 breast adenocarcinoma cell line (ATCC No. HTB 22; see also J. Natl. Cancer Inst. (Bethesda) 51, 1409–16 [1973]);

the MDA-MB 468 breast adenocarcinoma cell line (ATCC No. HTB 132; see also In Vitro 14, 911–15 [1978]);

the MDA-MB 231 breast adenocarcinoma cell line (ATCC No. HTB 26; see also J. Natl. Cancer Inst. (Bethesda) 53, 661–74 [1974]);

the Colo 205 colon carcinoma cell line (ATCC No. CCL 222; see also Cancer Res. 38, 1345–55 [1978]);

the HCT 116 colon carcinoma cell line (ATCC No. CCL 247; see also Cancer Res. 41, 1751–6 [1981]);

the DU145 prostate carcinoma cell line DU 145 (ATCC No. HTB 81; see also Cancer Res. 37, 4049–58 [1978]); and the PC-3 prostate carcinoma cell line PC-3 (ATCC No. CRL 1435; see also Cancer Res. 40, 524–34 [1980]).

A compound of formula I, or N-oxide thereof, inhibits to varying degrees also other tyrosine kinases involved in signal transduction which are mediated by trophic factors, for example Abl kinase, kinases from the Src family, especially c-Src kinase, Lck, and Fyn; also kinases of the EGF family, for example, c-erbB2 kinase (HER-2), c-erbB3 kinase, c-erbB4 kinase; insulin-like growth factor receptor kinase (IGF-1 kinase), especially members of the PDGF-receptor tyrosine kinase family, such as PDGF-receptor kinase, CSF-1-receptor kinase, Kit-receptor kinase and VEGF-receptor kinase; and also serine/threonine kinases, all of which play a role in growth regulation and transformation in mammalian cells, including human cells.

The inhibition of c-erbB2 tyrosine kinase (HER-2) can be measured, for example, in the same way as the inhibition of EGF-R protein kinase (see House et al., Europ. J. Biochem. 140, 363–7 [1984]). The erbB2 kinase can be isolated, and its activity determined, using methods known per se (see T. Akiyama et al., Science 232, 1644 [1986]).

An inhibitory effect can also be found especially on PDGF-receptor kinase, which is determined according to the method described by Trinks et al. (see J. Med. Chem. 37(7): 1015–27 [1994]). Inhibitory activity is shown here in the micromolar range using a compound of formula I (or an N-oxide thereof); the compound defined in Example 1 especially shows inhibitory activity with an $IC_{50}$ of approximately 1 µM.

On the basis of these studies, a compound of formula I (or an N-oxide thereof) according to the invention shows therapeutic efficacy especially against disorders dependent on protein kinase, especially proliferative diseases.

On the basis of their efficacy as inhibitors of VEGF-receptor tyrosine kinase activity, compounds of the invention primarily inhibit the growth of vessels and are thus, for example, effective against a number of diseases associated with deregulated angiogenesis, especially retinopathies, psoriasis, haemangioblastoma, haemangioma, and especially neoplastic diseases (solid tumours), such as especially breast cancer, cancer of the colon, lung cancer (especially small-cell lung cancer), or cancer of the prostate. A compound of formula I (or an N-oxide thereof) inhibits the growth of tumours and is especially suited also to preventing the metastatic spread of tumours and the growth of micrometastases.

A compound of formula I (or an N-oxide thereof) can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of formula I (or an N-oxide thereof) can besides or in addition be administered especially for tumour therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumour regression, or even chemopreventive therapy, for example in patients at risk.

Therapeutic agents for possible combination are especially one or more cytostatic or cytotoxic compounds, for example a chemotherapeutic agent or several selected from the group comprising an inhibitor of polyamine biosynthesis, an inhibitor of protein kinase, especially of serine/threonine protein kinase, such as protein kinase C, or of tyrosine protein kinase, such as epidermal growth factor receptor tyrosine kinase, a cytokine, a negative growth regulator, such as TGF-β or IFN-β, an aromatase inhibitor, a classical cytostatic, and an inhibitor of the interaction of an SH2 domain with a phosphorylated protein.

A compound according to the invention is not only for the (prophylactic and preferably therapeutic) management of humans, but also for the treatment of other warm-blooded animals, for example of commercially useful animals, for example rodents, such as mice, rabbits or rats, or guinea-pigs. Such a compound may also be used as a reference standard in the test systems described above to permit a comparison with other compounds.

In general, the invention relates also to the use of a compound of formula I (or an N-oxide thereof) for the inhibition of VEGF-receptor tyrosine activity.

A compound of formula I (or an N-oxide thereof) may also be used for diagnostic purposes, for example with tumours that have been obtained from warm-blooded animal "hosts", especially humans, and implanted into mice to test them for decreases in growth after treatment with such a compound, in order to investigate their sensitivity to the said compound and thus to improve the detection and determination of possible therapeutic methods for neoplastic diseases in the original host.

With the groups of preferred compounds of formula I mentioned hereinafter, definitions of substituents from the general definitions mentioned hereinbefore may reasonably be used, for example, to replace more general definitions with more specific definitions or especially with definitions characterized as being preferred;

(A) Preference is given to a compound of formula I comprised in a pharmaceutical preparation or to be used according to the invention wherein
r is 0 to 2, preferably 0,
n is 0 or 1,
m is 0 or also 1,
$R_1$, and $R_2$
(i) are lower alkyl, especially methyl, or
(ii) together form a bridge in subformula I*

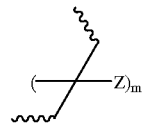

(I*)

the binding being achieved via the two terminal carbon atoms, or
(iii) together form a bridge in subformula I**

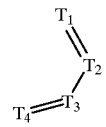

(I**)

wherein one of the ring members $T_1$, $T_2$, $T_3$ and $T_4$ is nitrogen, and the others are in each case CH, and the binding is achieved via $T_1$ and T4
A, B, D, and E are in each case CH, or also A, D, and E are each CH and B is N;
G is lower alkylene, especially methylene or ethylene (—$CH_2$—$CH_2$—), —$CH_2$—NH—, —$CH_2$—O—, hydroxymethylene, or benzoyloxymethylene,
Q is methyl, which is bound to A, to D, or to A and D;
R is H or lower alkyl, especially H or methyl,
X is imino, oxa, or thia,
Y is phenyl, which is unsubstituted or is substituted by one or two substituents independently of one another from the group comprising amino; lower alkanoylamino, especially acetylamino; halogen, especially fluorine, chlorine, or bromine; lower alkyl, especially methyl or also ethyl or propyl; halogen-lower alkyl, especially trifluoromethyl; hydroxy; lower alkoxy, especially methoxy or also ethoxy; phenyl-lower alkoxy, especially benzyloxy; and cyano, or (as an alternative or in addition to the previous group of substituents) lower alkenyl, such as ethenyl, $C_8$–$C_{12}$alkoxy, especially n-decyloxy, lower alkoxycarbonyl, such as tert-butoxycarbonyl, carbamoyl, lower alkylcarbamoyl, such as N-methyl- or N-tert-butylcarbamoyl, lower alkanoyl, such as acetyl, phenyloxy, halogen-lower alkyloxy, such as trifluoromethoxy or 1,1,2,2-tetrafluoroethyloxy, lower alkoxycarbonyl, such as ethoxycarbonyl, lower alkylmercapto, such as methylmercapto, halogen-lower alkylmercapto, such as trifluoromethylmercapto, hydroxy-lower alkyl, such as hydroxymethyl oder 1-hydroxymethyl, lower alkylsulfonyl, such as methanesulfonyl, halogen-lower alkylsulfonyl, such as trifluoromethanesulfonyl, phenylsulfonyl, dihydroxybora (—B(OH)₂), 2-methylpyrimidin-4-yl, oxazol-5-yl, 2-methyl-1,3-dioxolan-2-yl, 1 h-pyrazol-3-yl, 1-methyl-pyrazol-3-yl and lower alkylenedioxy bound to two adjacent C-atoms, such as methylenedioxy, or is also pyridyl, especially 3-pyridyl; especially phenyl, 2-, 3- or 4-aminophenyl, 2-, 3- or 4-acetylaminophenyl, 2-, 3- or 4-fluorophenyl, 2-, 3- or 4-chlorophenyl, 2-, 3- or 4-bromophenyl, 2,3-, 2,4-, 2,5- or 3,4-dichlorophenyl, chlorofluorophenyl, such as 3-chloro-4-fluorophenyl or also 4-chloro-2-fluoroanilino, 2,- 3- or 4-methylphenyl, 2-, 3- or 4-ethylphenyl, 2-, 3- or 4-propylphenyl, methylfluorophenyl, such as 3-fluoro-4-methylphenyl, 2-, 3- or 4-trifluoromethylphenyl, 2-, 3- or 4-hydroxyphenyl, 2-, 3- or 4-methoxyphenyl, 2-, 3- or 4-ethoxyphenyl, methoxychlorophenyl, such as 3-chloro-4-methoxycarbonyl, 2-, 3- or 4-benzyloxyphenyl, 2-, 3- or 4-cyanophenyl, or also 2-, 3- or 4-pyridyl;

Z is amino; N-lower alkylamino, such as N-methylamino; hydroxy-lower alkylamino, such as 2-hydroxyethylamino; phenyl-lower alkylamino, such as benzylamino; N,N-di-lower alkylamino; n-phenyl-lower alkyl-N-lower alkylamino; N,N-di-lower alkylphenylamino; lower alkanoylamino, such as acetylamino; or a substituent from the group comprising benzoylamino or phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl or carbamoyl; or is halogen, especially bromine; especially amino, acetylamino, nitrobenzoylamino, aminobenzoylamino, 2-hydroxyethylamino, benzyloxycarbonylamino or bromine; and, if present (in formula IA), the bonds characterized by a wavy line are in each case a double bond or in each case a single bond;

or of a pharmaceutically acceptable salt thereof; or to such a compound or pharmaceutically acceptable salt thereof wherein n=0 and the other moieties are as defined under (A) for use in the treatment of a disease mentioned hereinbefore or hereinafter; or to such a compound wherein n=0 and X is thia or is imino, and the other moieties are as defined under (A), or a pharmaceutically acceptable salt thereof.

(B) Special preference is given to a compound of formula I, especially formula IA, comprised in a pharmaceutical preparation or to be sued according to the invention wherein
r is 0;
n is 0 or 1,
m is 0;
A, B, D, and E are in each case CH,
G is lower alkylene, especially methylene,
R is H,
X is imino,
Y is phenyl, which is unsubstituted or is substituted by one or two substituents independently of one another from the group comprising amino; lower alkanoylamino, especially acetylamino; halogen, especially fluorine, chlorine, or bromine; lower alkyl, especially methyl; halogen-lower alkyl, especially trifluoromethyl; hydroxy; lower alkoxy, especially methoxy; phenyl-lower alkoxy, especially benzyloxy; and cyano; especially phenyl, 2-, 3- or 4-aminophenyl, 2-, 3- or 4-acetylaminophenyl, 2-, 3- or 4-fluorophenyl, 2-, 3- or 4-chlorophenyl, 2-, 3- or 4-bromophenyl, 2,3-, 2,4-, 2,5- or 3,4-dichlorophenyl, chlorofluorophenyl, such as 3-chloro-4-fluorophenyl, 2,- 3- or 4-methylphenyl, 2-, 3- or 4-trifluoromethylphenyl, 2-, 3- or 4-hydroxyphenyl, 2-, 3- or 4-methoxycarbonyl, methoxychlorophenyl, such as 3-chloro-4-methoxycarbonyl, 2-, 3- or 4-benzyloxyphenyl, or 2-, 3- or 4-cyanophenyl; and the bonds characterized by a wavy line are double bonds;

or a pharmaceutically acceptable salt thereof; or to such a compound of formula I, especially IA, wherein n=0 and the other moieties are as defined under (B), or a salt thereof.

Special preference is given to a compound of formula I, especially formula IA, such as is mentioned in the Examples below, or a pharmaceutically acceptable salt thereof, especially a compound specifically mentioned in the Examples or a salt thereof.

Special preference is given also to all compounds of formula I which have an $IC_{50}$ below 1 $\mu$M in Example 80.

High preference is given to a compound selected from 1-(4-Chloroanilino)-4-(4-pyridylmethyl)phthalazine;
1-(3-Chloroanilino)-4-(4-pyridylmethyl)phthalazine;
1-Anilino-4-(4-pyridylmethyl)phthalazine;
1-Benzylamino-4-(4-pyridylmethyl)phthalazine;
1-(4-Methoxyanilino)-4-(4-pyridylmethyl)phthalazine;
1-(3-Benzyloxyanilino)-4-(4-pyridylmethyl)phthalazine;
1-(3-Methoxyanilino)-4-(4-pyridylmethyl)phthalazine;
1-(2-Methoxyanilino)-4-(4-pyridylmethyl)phthalazine;
1-(4-Trifluoromethylanilino)-4-(4-pyridylmethyl) phthalazine;
1-(4-Fluoroanilino)-4-(4-pyridylmethyl)phthalazine;
1-(3-Hydroxyanilino)-4-(4-pyridylmethyl)phthalazine;
1-(4-Hydroxyanilino)-4-(4-pyridylmethyl)phthalazine;
1-(3-Aminoanilino)-4-(4-pyridylmethyl)phthalazine;
1-(3,4-Dichloroanilino)-4-(4-pyridylmethyl)phthalazine;
1-(4-Bromoanilino)-4-(4-pyridylmethyl)phthalazine;
1-(3-Chloro-4-methoxyanilino)-4-(4-pyridylmethyl) phthalazine;
1-(4-Cyanoanilino)-4-(4-pyridylmethyl)phthalazine;
1-(4-Methylanilino)-4-(4-pyridylmethyl)phthalazine; and also
1-(3-Chloro-4-fluoroanilino)-4-(4-pyridylmethyl) phthalazine;
1-(3-Methylanilino)-4-(4-pyridylmethyl)phthalazine;

or a pharmaceutically acceptable salt thereof.

A compound of formula I may be prepared by processes known per se for other compounds, especially by reacting a) a compound of formula II,

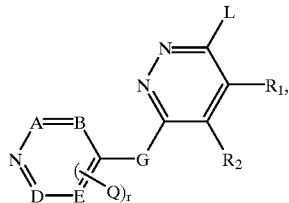
(II)

wherein A, B, D, E, Q, G, R₁, R₂, and n are as defined for a compound of formula I [, especially a phthalazine derivative of formula IIA,

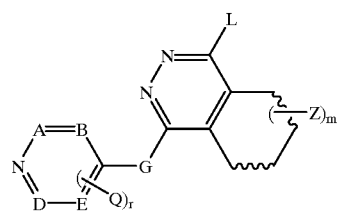
(IIA)

wherein r, m, A, B, D, E, G, Q, and Z, as well as bonds characterized by wavy lines, are as defined for a compound of formula IA]

and L is a nucleofugal leaving group, with a compound of formula III

(III)

wherein n, R, X, and Y are as defined for a compound of formula I, the functional groups in the compounds of formula II and formula III which do not participate in the reaction being present in protected form where necessary, and removing any protective groups present, or reacting b) a compound of formula IV,

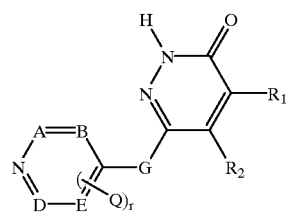

wherein A, B, D, E, Q, G, R₁, R₂, and r are as defined for a compound of formula I [, especially a phthalazinone compound of formula IVA,

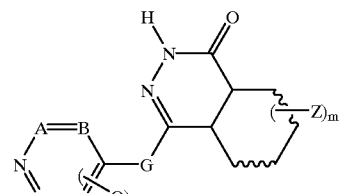
(IVA)

wherein r, m, A, B, D, E, G, Q, and Z, as well as bonds characterized by wavy lines, are as defined for a compound of formula IA] with a compound of formula III, as shown under process a), in the presence of a dehydrating agent and a tertiary amine, the functional groups in the compounds of formula II and formula III which do not participate in the reaction being present in protected form where necessary, and removing any protective groups present, or c) for the preparation of a compound of formula I, wherein G is —CH₂—, —CH₂—O—, —CH₂—S— or —CH₂—NH—, or also oxa, thia, or imino, and the other symbols are as described for a compound of formula I, reacting a compound of formula V,

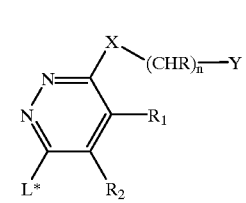
(V)

wherein the radicals R₁, R₂, X, Y, R and r, are as defined for a compound of formula I,

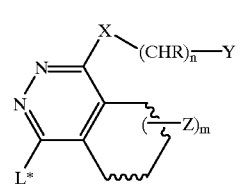
(VA)

wherein Z, Y, x, R, n, and m are as described for compounds of formula IA] and wherein L is a nucleofugal leaving group, with a compound of formula VI,

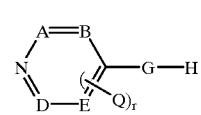
(VI)

wherein G is —CH₂—O—, —CH₂—S— or —CH₂—NH—, or also oxa, thia or imino and A, B, D, E, O, and r are as defined for compounds of formula I, or (for the preparation of a compound of formula I, wherein G is the bivalent radical —CH$_2$—) with the corresponding metallate of a compound of formula VI, wherein the radical —CH$_2$—Me takes the place of G—H, wherein Me is a metal, the functional groups in the compounds of formula V and formula VI or their metallate which do not participate in the reaction being present in protected form where necessary, and removing any protective groups present, or d) for preparation of a compound of formula i, wherein G is —CH$_2$—O—, —CH$_2$—S—, —CH$_2$—NH—, oxa, thia or imino, and the other symbols are as described for a compound of formula I, reacting a compound of formula VII,

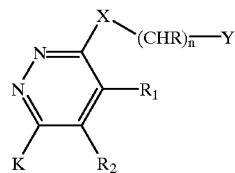

(VII)

wherein X, Y, R$_1$, R$_2$, R and n are as defined for a compound of formula I,

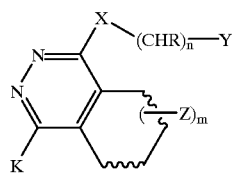

(VIIA)

wherein X, Y, Z, R, m, and n are as described for compounds of formula IA] and where K is amino, hydroxy or mercapto, or a tautomer thereof, with a compound of formula VIII,

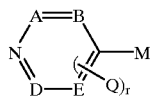

(VIII)

wherein M is —CH$_2$—L or —L, where L** is a nucleofugal leaving group; and the other symbols are as described for a compound of formula I, the functional groups in the compounds of formula VII and formula VIII which do not participate in the reaction being present in protected form where necessary, and removing any protective groups present, or e) for the preparation of a compound of formula I, wherein G is lower alkylene substituted by acyloxy, and the other radicals are as under formula I, reacting a compound of formula

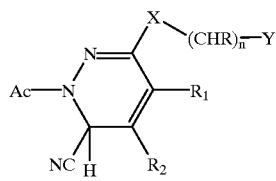

(XV)

wherein Ac is acyl, as defined under formula I for lower alkylene G substituted by acyloxy, and X, Y, R$_1$, R$_2$, R, and n are as defined for a compound of formula I, with an aldehyde of formula XVI,

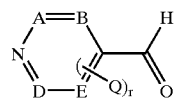

(XVI)

wherein A, B, D, E, Q, and r are as described for a compound of formula I, in the presence of a strong base, the functional groups in the compounds of formula XV and formula XVI which do not participate in the reaction being present in protected form where necessary, and removing any protective groups present, where the starting compounds defined in a) to e) may also be present in the form of salts, provided a salt-forming group is present and the reaction in salt form is possible;

and, if so desired, converting an obtainable compound of formula I or an N-oxide thereof into another compound of formula I or an N-oxide thereof, converting a free compound of formula I or an N-oxide thereof into a salt, converting an obtainable salt of a compound of formula I or an N-oxide thereof into the free compound or another salt, and/or separating a mixture of isomeric compounds of formula I or N-oxides thereof into the individual isomers.

Detailed Description of the Process Varients

In the more detailed description of the process below, r, n, m, R$_1$, R$_2$, A, B, D, E, G, Q, R, X, Y, and Z, as well as the bonds characterized by a wavy line, are as defined for compounds of formula 1, unless otherwise indicated.

Process a)

In the compound of formula II, a nucleofugal leaving group L is especially halogen, above all bromine, iodine, or especially chlorine.

The reaction between the compound of formula II and the compound of formula III takes place in suitable, inert polar solvents, especially alcohols, e.g. lower alkanols, such as methanol, propanol or especially ethanol or n-butanol, or in a melt without the addition of a solvent, especially if one of the reaction partners is present in liquid form. The reaction takes place at elevated temperatures, preferably between about 60° C. and the reflux temperature, for example under reflux conditions, or at a temperature between approximately 90 and approximately 110° C. The compound of formula III can be used as a salt, for example as an acid addition salt with a strong acid, such as hydrogen halide, for example as a hydrochloride salt.

If one or more other functional groups, for example carboxy, hydroxy, amino, or mercapto, are or need to be protected in a compound of formulae II and/or III, because they should not take part in the reaction, these are such groups as are usually used in the synthesis of peptide compounds, and also of cephalosporins and penicillins, as well as nucleic acid derivatives and sugars.

The protecting groups for functional groups in raw materials whose transformation should be avoided, in particular carboxy, amino, hydroxy, and mercapto groups, include especially the conventional protecting groups that are normally used in the synthesis of peptide compounds, but also those used in the synthesis of cephalosporins and penicillins, as well as nucleic acids and sugars. The protecting groups may already be present in precursors and should protect the functional groups concerned against unwanted secondary reactions, such as acylations, etherifications, esterifications, oxidations, solvolysis, and similar reactions. In certain cases, the protecting groups may, in addition to this protection, effect a selective, typically stereoselective, course of reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter.

The protection of such functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

Protecting groups which are not components of the desired end-product of formula I (or the N-oxide thereof), typically the carboxy, amino, hydroxy, and/or mercapto protecting groups, are removed in known manner, for example by solvolysis, especially hydrolysis, alcoholysis, or acidolysis, or by reduction, especially hydrogenolysis or using other reducing agents, as well as photolysis, where applicable in gradual steps or simultaneously; enzymatic methods may also be used. The removal of protecting groups is described for example in the reference works mentioned hereinabove in the section on "Protecting groups".

The protecting groups mentioned in the Examples are preferably introduced according to the methods described and where necessary removed.

Process b)

The compound of formula IV is in tautomeric equilibrium (lactam/lactim form), the lactam form (formula IV) presumably predominating. Formula IV is used to represent the two possible equilibrium forms.

The lactim form has the structure as in formula IV*,

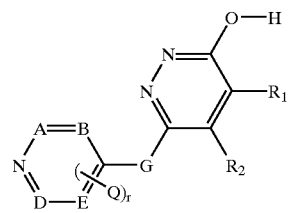

(IV*)

wherein the radicals are as defined above for compounds of formula IV.

As dehydrating agent, especially a strong chemical dehydrating agent is used, especially phosphorus pentoxide ($P_4O_{10}$).

Suitable as tertiary amine is especially ammonia substituted by three radicals selected independently of one another from alkyl, especially lower alkyl, such as methyl or ethyl, and cycloalkyl having from 3 to 7 carbon atoms, especially cyclohexyl, for example N,N-dimethyl-N-cyclohexylamine, N-ethyl-N,N-diisopropylamine or triethylamine, or, furthermore, also pyridine, N-methylmorpholine or 4-dimethylaminopyridine.

In the preferred embodiment, the tertiary amine is present as a salt with a strong acid, preferably an inorganic acid, typically sulfuric acid, phosphoric acid, or especially a hydrogen halogenide, such as hydrogen chloride.

The reaction between the phthalazinone of formula IV and the compound of formula III takes place at elevated temperature, for example at from 160 to 250° C.

The types of protecting groups used, the mode of introduction, and the methods of removing them from compounds of formulae III and IV as well as compounds obtainable from formula I (and where applicable N-oxides thereof) correspond to the specifications given under process a).

Process c)

In the compound of formula V there is a nucleofugal leaving group L*, especially halogen, above all bromine, iodine, or especially chlorine.

The reaction between the compound of formula V and that of formula VI takes place preferably under conditions as described under process a) for the reaction of a compound of formula II with a compound of formula III, provided G is —$CH_2$—O—, —$CH_2$—S—, —$CH_2$—NH—, oxa, thia, or imino; if a compound of formula VI is used, wherein the place of the G—H group is taken by the radical —$CH_2$—Me (a compound of formula VI, wherein G is —$CH_2$— and is present as a metallate), the reaction can be carried out under catalysis with a palladium complex, for example with tetrakis(triphenylphosphinyl)palladium complexes, palladium(0)-P(o-tolyl)$_3$ complexes, palladium(0) complexes with chelating bis(phosphines) (see for example J. Org. Chem. 61, 7240–1 [1996]) or similar. In the radical —$CH_2$—Me, Me is especially Li or Sn.

Process c) is preferably used for the preparation of a compound of formula I (and N-oxides thereof), wherein G is —$CH_2$—O—, —$CH_2$—S—, —$CH_2$—NH—, oxa, thia, or imino, based on the corresponding compounds of formulae VI and V.

The types of protecting groups used, the mode of introduction, and the methods of removing them from compounds of formulae V and III (including the metallate if G=—$CH_2$—) as well as compounds obtainable from formula I (and where applicable N-oxides thereof) correspond to the specifications given under process a).

Process d)

A starting compound of formula VII may also be present as a tautomer; a proton belonging to K may thus be transferred to a cyclic nitrogen of the phthalazine ring system so that an imino (=NH), oxo (=O), or thioxo (=S) is then present instead of K, and a double bond in the phthalazine ring is missing. The specialist is familiar with the occurrence of such tautomeric compounds. A compound of formula VII may also occur as a mixture of tautomers, if these are present for example in equilibrium under the reaction conditions.

In the compound of formula VII there is a nucleofugal leaving group L**, especially halogen, above all bromine, iodine, or especially chlorine.

The reaction between the compound of formula VII and that of formula VIII takes place preferably under conditions as described under process a) for the reaction of a compound of formula II with a compound of formula III.

The types of protecting groups used, the mode of introduction, and the methods of removing them from compounds of formulae VII and VIII as well as compounds obtainable from formula I correspond to the specifications given under process a).

Process e)

The reaction between the compound of formula XV and formula XVI takes place preferably in a suitable inert solvent, typically an ether, for example tetrahydrofuran, at low temperatures, preferably between –80 and –50° C., for example at about –78° C., in the presence of a strong base, for example an alkali metal-bis(tri-lower alkylsilyl)amide, e.g. lithium or potassium-bis(trimethylsilyl)amide, the compound of formula XV preferably first being incubated in the solvent with the base, and the compound of formula XVI then being added.

The types of protecting groups used, the mode of introduction, and the methods of removing them from compounds of formulae XV and XVI as well as compounds obtainable from formula I correspond to the specifications given under process a).

Additional Process Steps

In the additional process steps, carried out as desired, functional groups of the starting compounds which should not take part in the reaction may be present in unprotected form or may be protected for example by one or more of the protecting groups mentioned hereinabove under process a). The protecting groups are then wholly or partly removed according to one of the methods described under process a).

Salts of a compound of formula I (or an N-oxide thereof) with a salt-forming group may be prepared in a manner known per se. Acid addition salts of compounds of formula I or N-oxides thereof may thus be obtained by treatment with an acid or with a suitable anion exchange reagent. A salt with two acid molecules (for example a dihalogenide of a compound of formula I [or an N-oxide thereof]) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of formula I (or an N-oxide thereof).

Salts can usually be converted to free compounds, e.g. by treating with suitable basic agents, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

A compound of formula I can be converted to a corresponding N-oxide. The reaction is carried out with a suitable oxidizing agent, preferably a peroxide, for example m-chloroperbenzoic acid, in a suitable solvent, e.g. halogenated hydrocarbon, typically chloroform or dichloromethane, or in a lower alkanecarboxylic acid, typically acetic acid, preferably at a temperature between 0° C. and the boiling temperature of the reaction mixture, especially at about room temperature.

A compound of formula I (or an N-oxide thereof), wherein Z is lower alkanoylamino, can be hydrolysed to a corresponding amino compound (Z=amino), for example by hydrolysis with an inorganic acid, especially hydrogen chloride (HCl) in an aqueous solution, further solvents possibly being added, preferably at elevated temperature, e.g. under reflux.

A compound of formula I (or an N-oxide thereof), wherein Z is amino substituted by one or two radicals selected independently from lower alkyl, hydroxy-lower alkyl, and phenyl-lower alkyl, can be converted to a compound that is correspondingly substituted at the amino group, for example by reaction with a lower alkyl halide, if necessary a hydroxy-protected (see process a)) hydroxy-lower alkyl halide or phenyl-lower alkyl halide, under reaction conditions as described under process a). For the introduction of 2-hydroxy-lower alkyl substituents at the amino group Z, addition based on an epoxide (for example ethylene oxide) is also possible. The addition takes place especially in aqueous solution and/or in the presence of polar solvents, typically alcohols, for example methanol, ethanol, isopropanol, or ethylene glycol, ethers, typically dioxane, amides, typically dimethylformamide, or phenols, typically phenol, and also under non-aqueous conditions, in non-polar solvents, typically benzene and toluene, or in benzene/water emulsions, where applicable in the presence of acidic or basic catalysts, for example leaches, typically sodium hydroxide solution, or in the presence of solid-phase catalysts, typically aluminium oxide, that have been doped with hydrazine, in ethers, for example diethylether, generally at temperatures from about 0° C. to the boiling temperature of the corresponding reaction mixture, preferably between 20° C. and reflux temperature, if necessary under increased pressure, e.g. in a sealed tube, a temperature in excess of boiling point also being possible, and/or under inert gas, typically nitrogen or argon. Reductive alkylation of an amino group Z with a lower alkanaldehyde, a phenyl-lower alkanaldehyde, or a hydroxy-lower alkanaldehyde, if necessary hydroxy-protected, is also possible. Reductive alkylation takes place preferably under hydrogenation in the presence of a catalyst, especially a precious-metal catalyst, typically platinum or especially palladium, which is preferably bound to a carrier, such as carbon, or in the presence of a heavy-metal catalyst, typically Raney-Nickel, at normal pressure or at pressures from 0.1 to 10 megapascal (MPa), or under reduction using complex hydrides, typically boranes, especially alkali cyanoborohydride, for example sodium cyanoborohydride, in the presence of a suitable acid, preferably a relatively weak acid, typically a lower alkanecarboxylic acid or especially a sulfonic acid, such as p-toluenesulfonic acid; in customary solvents, for example alcohols, such as methanol or ethanol, or ethers, for example cyclic ethers, such as tetrahydrofuran, in the presence or absence of water.

In a compound of formula I (or an N-oxide thereof), an amino group Z can be converted by acylation to an amino group substituted by lower alkanoyl, benzoyl, substituted benzoyl, or phenyl-lower alkoxycarbonyl, wherein the phenyl radical is unsubstituted or substituted. The corresponding acids comprise a free carboxy group or are present as reactive acid derivatives thereof, for example activated ester or reactive anhydride derivatives, and also reactive cyclic amide derivatives. The reactive acid derivatives may also be formed in situ. Activated esters are especially unsaturated esters at the bonding carbon atom of the radical to be esterified, for example of the vinyl ester type, typically vinyl ester (obtainable for example by reesterification of an appropriate ester with vinyl acetate; activated vinyl ester method), carbamoyl ester (obtainable for example by treatment of the corresponding acid with an isoxazolium reagent; 1,2-oxazolium or Woodward method), or 1-lower alkoxyvinyl ester (obtainable for example by treatment of the corresponding acid with a lower alkoxyacetylene; ethoxyacetylene method), or esters of the amidino type, typically N,N'-disubstituted amidino ester (obtainable for example by treatment of the corresponding acid with a suitable N,N'-disubstituted carbodiimide, for example N,N'-dicyclohexylcarbodiimide or especially N-(3-dimethylaminopropyl)-N'-ethylcarbodiimide; carbodiimide method), or N,N-disubstituted amidino ester (obtainable for example by treatment of the corresponding acid with an N,N-disubstituted cyanamide; cyanamide method), suitable aryl esters, especially phenyl esters suitably substituted by electrophilic substituents (obtainable for example by treatment of the corresponding acid with a suitably substituted phenol, for example 4-nitrophenol, 4-methylsulfonylphenol, 2,4,5-trichlorophenol, 2,3,4,5,6-pentachlorophenol or 4-phenyidiazophenol, in the presence of a condensing agent, typically N,N'-dicyclohexylcarbodiimide; method of activated aryl esters), cyanomethyl esters (obtainable for example by treatment of the corresponding acid with chloroacetonitrile in the presence of a base; cyanomethyl ester method), thioesters, where appropriate especially phenylthio esters substituted, for example, by nitro (obtainable for example by treatment of the corresponding acid where appropriate with thiophenols substituted, for example, by nitro, with the aid also of the anhydride or carbodiimide method; activated thiolester method), or especially amino or amido esters (obtainable for example by treatment of the corresponding acid with an N-hydroxyamino- or N-hydroxyamido compound, for example N-hydroxysuccinimide, N-hydroxypiperidine, N-hydroxyphthalimide, N-hydroxy-5-norbornene-2,3-dicarboximide, 1-hydroxybenztriazole or 3-hydroxy-3,4-dihydro-1,2,3-benztriazin-4-one, for example according to the anhydride or carbodiimide method; activated N-hydroxy ester method). Internal esters, for example γ-lactones, can also be used. Anhydrides of acids can be symmetrical or preferably mixed anhydrides of these acids, for example anhydrides with inorganic acids, typically acid halides, especially acid chloride (obtainable for example by treatment of the corresponding acid with thionyl chloride, phosphorus pentachlorde, phos-gene or oxalyl chloride; acid chloride method), azide (obtainable for example from a corresponding acid ester via the corresponding hydrazide and treatment thereof with nitrous acid; azide method), anhydrides with carbonic acid semi-esters, e.g. carbonic acid-lower alkyl semi-esters (especially methyl chlorocarbonate) (obtainable for example by treatment of the corresponding acid with chlorocarbonic acid-lower alkyl esters or with a 1-lower alkoxycarbonyl-2-lower alkoxy-1, 2-dihydroquinoline; mixed O-alkylcarbonic anhydride method), or anhydrides with dihalogenated, especially dichlorinated phosphoric acid (obtainable for example by treatment of the corresponding acid with phosphoroxychloride; phosphoroxychloride method), anhydrides with other phosphoric acid derivatives (for example, such as are obtainable with phenyl-N-phenylphosphoramidochloridate or by reaction of alkylphosphoric acid amides in the presence of sulfonic acid anhydrides and/or racemization-reducing additives, typically N-hydroxybenztriazole, or in the presence of cyanophosphonic acid diethyl ester) or with phosphorous acid derivatives, or anhydrides with organic acids, such as mixed anhydrides with organic carbonic acids (obtainable for example by treatment of the corresponding acid with a lower alkane or phenyl-lower alkanecarboxylic acid halide, substituted where appropriate, typically phenylacetyl, pivaloyl, or trifluoroacetic acid chloride; mixed carboxylic acid anhydride method) or with organic sulfonic acids (obtainable for example by treatment of a salt, typically an alkali metal salt, the corresponding acid with a suitable organic sulfonic acid halide, typically lower alkane or aryl, for example methane or p-toluenesulfonic acid chloride; method of mixed sulfonic acid anhydrides), as well as symmetrical anhydrides (obtainable for example through condensation of the corresponding acid in the presence of a carbodiimide or of 1-diethylaminopropine; method of symmetrical anhydrides). Suitable cyclic amides are especially amides with five-member diazacycles of aromatic character, typically amides with imidazolene, for example imidazole (obtainable for example by treatment of the corresponding acid with N,N'-carbonyldiimidazole; imidazole method), or pyrazole, for example 3,5-dimethylpyrazole (obtainable for example via the acid hydrazide by treatment with acetylacetone; pyrazolide method). As mentioned, carboxylic acid derivatives, which are used as acylation agents, can also be formed in situ. For example, N,N'-disubstituted amidino esters can be formed in situ by reacting the mixture of the starting material of formula I and the acid used as acylation agent in the presence of a suitable N,-N'-disubstituted carbodiimide, for example N,-N'-cyclohexylcarbodiimide or in particular N-(3-dimethylaminopropyl)-N'-ethylcarbodiimide. Amino or amido esters of the acids used as acylation agents can also be formed in the presence of the starting material of formula I that is to be acylated by reacting the mixture of the corresponding acid and amino starting materials in the presence of an N,N'-disubstituted carbodiimide, for example N,N'-dicyclohexylcarbodiimide, and an N-hydroxyamine or N-hydroxyamide, for example N-hydroxysuccinimide, where appropriate in the presence of a suitable base, for example 4-dimethylaminopyridine. Activation can also be achieved in situ through reaction with N,N,N',N'-tetraalkyluronium compounds, typically O-benztriazol-1yl-N,N,N',N'-tetramethyluronium hexafluorophosphate, O-(1,2-dihydro-2-oxo-1-pyridyl)-N, N,N',N'-tetramethyluronium tetrafluoroborate (in the presence or absence of 1,8-diazabicyclo[5.4.0]undec-7-ene-(1, 5-5)), or O-(3,4-dihydro-4-oxo-1,2,3-benztriazolin-3-yl)-N, N,N',N'-tetramethyluronium tetrafluoroborate. Finally, phosphoric acid anhydrides of carboxylic acids can be prepared in situ by reacting an alkylphosphoric acid amide, typically hexamethylphosphoric acid triamide, in the presence of a sulfonic acid anhydride, typically 4-toluenesulfonic acid anhydride, with a salt, such as tetrafluoroborate, for example sodium tetrafluoroborate, or with another derivative of hexamethylphosphoric acid triamide, typically benzotriazol-1-yl-oxy-tris-(dimethylamino)-phosphonium hexafluoride. If desired, an organic base is added, preferably a tertiary amine, for example a tri-lower alkylamine, especially ethyldiisopropylamine or above all triethylamine, and/or a heterocyclic base, for example 4-dimethylaminopyridine or preferably N-methylmorpholine or pyridine. Condensation is carried out preferably in an inert, aprotic, preferably non-aqueous solvent or solvent mixture, typically in a carboxamide, for example formamide or dimethylformamide, a halogenated hydrocarbon, for example dichloromethane, tetrachloromethane, or chlorobenzene, a ketone, for example acetone, a cyclic ether, for example tetrahydrofuran or dioxane, an ester, for example ethyl acetate, or a nitrile, for example acetonitrile, or in a mixture thereof, where appropriate at reduced or elevated temperature, for example in a range from about −40° C. to about +100° C., preferably from about −10° C. to about +70° C., also from about +100° C. to +200° C. when arylsulfonyl esters are used, especially at temperatures between 10 and 30° C., and where appropriate under inert gas, for example nitrogen or argon. Aqueous, typically alcoholic, for example ethanol, or aromatic solvents, for example benzene or toluene, are also possible.

A nitro group Z in a compound of formula I can be reduced to an amino group, for example by reduction with metals or by selective hydrogenation; for example by reaction with magnesium/ammonium sulfate in a water/alcohol mixture, typically methanol/water, at elevated temperature, for example between 30 and 60° C. (see Synth. Commun. 25 [2], 4025–8 [1995]); by reaction with zinc/boron hydride in an acid amide, typically dimethylformamide, at temperatures below room temperature, for example at about 0° C.; by reaction with 1,1'-dioctyl-4,4'-bipyridinium dibromide/sodium tetrathionate/potassium carbonate in water/halogenated hydrocarbon mixtures, for example water/dichloromethane mixtures, at elevated temperature, for example from 25 to 35° C. (see Tetrahedron Lett. 34(46), 7445–6 (1993)); with sodium borohydride on Amberlyte IRA-400 ion exchanger in chloride form in an alcohol, typically methanol/water, at preferred temperatures between 0 and 40° C. (see Synthetic Commun. 19(5/6), 805–11 (1989)); with potassium borohydride in a halogenated hydrocarbon/alcohol mixture, for example dichloromethane/methanol, at preferred temperatures between 10 and 35° C. (see Synthetic Commun. 19(17), 3047–50 (1989)); with sodium borohydride in dioxane; with borane in tetrahydrofuran; by hydrogenation in the presence of Pd/C in an alcohol at a preferred temperature of 0 to 35° C. and in the presence of ammonium formate (see Tetrahedron Lett. 25(32), 3415–8 (1989)); with titanium tetrachloride/lithium aluminium hydride or titanium tetrachloride/magnesium in an ether, typically tetrahydrofuran (see Bull. Chem. Soc. Belg. 97 [1], 51–3 [1988]); or with ferric ammonium chloride/water at elevated temperature, preferably under reflux (Synth. Commun. 22, 3189–95 [1992]).

In a compound of formula I, wherein G is lower alkyl substituted by acyloxy and the other radicals are as defined under formula I, the acyl radical can be removed by hydrolysis, resulting in the corresponding compound of formula I, in which G is lower alkylene substituted by hydroxy. The hydrolysis is carried out preferably under the usual conditions, typically in the presence of acids or bases, such as HCl or NaOH, in aqueous solution or a suitable solvent or solvent mixture.

From a compound of formula I wherein G is lower alkyl substituted by acycloxy, a compound of formula I can also be prepared wherein G is lower alkylene. The reaction here is carried out preferably with catalytic hydrogenation (hydrogen in the presence of a suitable catalyst) in a customary solvent or solvent mixture.

General Process Conditions

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralisiing agents, for example ion exchangers, typically cation exchangers, for example in the $H^+$ form, depending on the type of reaction and/or reactants at reduced, normal, or elevated temperature, for example in the range from −100° C. to about 190° C., preferably from about −80° C. to about 150° C., for example at −80 to −60° C., at room temperature, at −20 to 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric mixtures, typically as described under "Additional process steps".

In certain cases, typically in hydrogenation processes, it is possible to achieve stereo-selective reactions, allowing for example easier recovery of individual isomers.

The solvents from which those can be selected which are suitable for the reaction in question include for example water, esters, typically lower alkyl-lower alkanoates, e.g diethyl acetate, ethers, typically aliphatic ethers, e.g. diethylether, or cyclic ethers, e.g. tetrahydrofuran, liquid aromatic hydrocarbons, typically benzene or toluene, alcohols, typically methanol, ethanol or 1- or 2-propanol, nitriles, typically acetonitrile, halogenated hydrocarbons, typically dichloromethane, acid amides, typically dimethylformamide, bases, typically heterocyclic nitrogen bases, e.g. pyridine, carboxylic acids, typically lower alkanecarboxylic acids, e.g. acetic acid, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process. Such solvent mixtures may also be used in processing, for example through chromatography or distribution.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described hereinabove as preferred, particularly as especially preferred, primarily preferred, and/or preferred above all.

In the preferred embodiment, a compound of formula I (or N-oxide thereof) is prepared according to the processes and process steps defined in the Examples.

The compounds of formula I (or N-oxides thereof), including their salts, are also obtainable in the form of hydrates, or their crystals can include for example the solvent used for crystallization (present as solvates).

Pharmaceutical Preparations, Methods, and Uses

The present invention relates also to pharmaceutical compositions that comprise a compound of formula I (or an N-oxide thereof) as active ingredient and that can be used especially in the treatment of the diseases mentioned at the beginning. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The invention relates also to pharmaceutical compositions for use in a method for the prophylactic or especially therapeutic management of the human or animal body, to a process for the preparation thereof (especially in the form of compositions for the treatment of tumours) and to a method of treating tumour diseases, especially those mentioned hereinabove.

The invention relates also to processes and to the use of compounds of formula I (or an N-oxide thereof) for the preparation of pharmaceutical preparations which comprise compounds of formula I (or an N-oxide thereof) as active component (active ingredient).

In the preferred embodiment, a pharmaceutical preparation is suitable for administration to a warm-blooded animal, especially humans or commercially useful mammals suffering from a disease responsive to an inhibition of angiogenesis or of VEGF-receptor tyrosine kinase, for example psoriasis or especially a neoplastic disease, and comprises an effective quantity of a compound of formula I (or an N-oxide thereof) for the inhibition of angiogenesis or of VEGF-receptor tyrosine kinase, or a pharmaceutically acceptable salt thereof, if salt-forming groups are present, together with at least one pharmaceutically acceptable carrier.

A pharmaceutical composition for the prophylactic or especially therapeutic management of neoplastic and other proliferative diseases of a warm-blooded animal, especially a human or a commercially useful mammal requiring such treatment, especially suffering from such a disease, comprising as active ingredient in a quantity that is prophylactically or especially therapeutically active against the said diseases a novel compound of formula I (or an N-oxide thereof), is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, lip-sticks, drops, sprays, dispersions, etc. Examples are capsules containing from about 0.05 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known perse, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, for example Tween 80 [polyoxyethylene(20)sorbitan mono-oleate; trademark of ICI Americas, Inc, USA].

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcohol component of these fatty acid esters has a maximum of 6 carbon atoms and is a mono-valent or polyvalent, for example a mono-, di- or trivalent, alcohol, for example methanol, ethanol, propanol, butanol or pentanol or the isomers thereof, but especially glycol and glycerol. As fatty acid esters, therefore, the following are mentioned: ethyl oleate, isopropyl myristate, isopropyl palmitate, "Labrafil M 2375" (polyoxyethylene glycerol trioleate from Gattefossé, Paris), "Labrafil M 1944 CS" (unsaturated polyglycolized glycerides prepared by alcoholysis of apricot kernel oil and consisting of glycerides and polyethylene glycol ester; Gattefossé, France), "Labrasol" (saturated polyglycolized glycerides prepared by alcoholysis of TCM and consisting of glycerides and polyethylene glycol ester; Gattefossé, France), and/or "Miglyol 812" (triglyceride of saturated fatty acids of chain length $C_8$ to $C_{12}$ from Hüls A G, Germany), but especially vegetable oils such as cottonseed oil, almond oil, olive oil, castor oil, sesame oil, soybean oil and more especially groundnut oil.

The manufacture of injectable preparations is usually carried out under sterile conditions, as is the filling, for example, into ampoules or vials, and the sealing of the containers.

Pharmaceutical compositions for oral administration can be obtained, for example, by combining the active ingredient with one or more solid carriers, if desired granulating a resulting mixture, and processing the mixture or granules, if desired or necessary, by the inclusion of additional excipients, to form tablets or tablet cores.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, cross-linked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Other oral dosage forms are, for example, syrups prepared in customary manner which comprise the active ingredient, for example, in suspended form and in a concentration of about 5% to 20%, preferably about 10%, or in a similar concentration that provides a suitable single dose, for example, when administered in measures of 5 or 10 ml. Also suitable are, for example, powdered or liquid concentrates for the preparation of shakes, for example in milk. Such concentrates may also be packaged in single-dose units.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

The invention relates likewise to a process or a method for the treatment of one of the pathological conditions mentioned hereinabove, especially a disease which responds to an inhibition of the VEGF-receptor tyrosine kinase or an inhibition of angiogenesis, especially a corresponding neoplastic disease or also psoriasis. The compounds of formula I (or an N-oxide thereof) can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.1 g to approximately 5 g, preferably from approximately 0.5 g to approximately 2 g, of a compound of the present invention.

The present invention relates especially also to the use of a compound of formula I (or an N-oxide thereof), or a pharmaceutically acceptable salt thereof, especially a compound of formula I which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, especially a neoplastic disease or also psoriasis, more especially if the disease responds to an inhibition of angiogenesis or an inhibition of VEGF-receptor tyrosine kinase.

The present invention relates especially also to the use of a compound of formula I (or an N-oxide thereof), or a pharmaceutically acceptable salt thereof, especially a compound of formula I which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, preferably a disease which responds to an inhibition of VEGF-receptor tyrosine kinase or an inhibition of angiogenesis, especially a neoplastic disease or also psoriasis, more especially if the said disease responds to an inhibition of VEGF-receptor tyrosine kinase or angiogenesis.

The present invention relates especially also to the use of a compound of formula I (or an N-oxide thereof), or a pharmaceutically acceptable salt thereof, especially a compound of formula I which is said to be preferred, or a pharmaceutically acceptable salt thereof, for the preparation of a pharmaceutical formulation for the therapeutic and also prophylactic management of one or more of the diseases mentioned hereinabove, especially a neoplastic disease or also psoriasis, more especially if the disease responds to an inhibition of VEGF-receptor tyrosine kinase or angiogenesis.

The preferred dose quantity, composition, and preparation of pharmaceutical formulations (medicines) which are to be used in each case are described above.

Starting Materials

New starting materials and/or transients, as well as processes for the preparation thereof, are likewise the subject of this invention. In the preferred embodiment, such starting materials are used and reaction conditions so selected as to enable the preferred compounds to be obtained.

The starting materials of formulae II, III, IV, V, VI, VII, and VIII, and of XV and XVI, are known, capable of being prepared according to known processes, or commercially obtainable; in particular, they can be prepared using processes as described in the Examples.

In the preparation of starting materials, existing functional groups which do not participate in the reaction should, if necessary, be protected. Preferred protecting groups, their introduction and their removal are described under process a) or in the Examples. In place of the respective starting materials and transients, salts thereof may also be used for the reaction, provided that salt-forming groups are present and the reaction with a salt is also possible. Where reference is made hereinbefore and hereinafter to starting materials, the salts thereof are thus also always implied, insofar as their use is appropriate and feasible.

A compound of formula II, wherein G is methylene and the other symbols are as defined for a compound of formula I, may be prepared for example by converting an acid anhydride of formula IX,

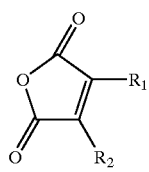
(IX)

[especially of formula IXA,

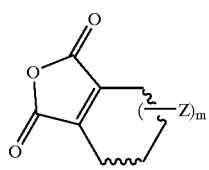
(IXA)]

wherein the symbols are as defined for a compound of formula I [especially formula IA], in a melt at elevated temperature, preferably a temperature between 50 and 200° C., with a compound of formula X,

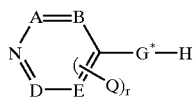
(X)

wherein G* is methylene and the other symbols are as defined for a compound of formula I, to a compound of formula XI,

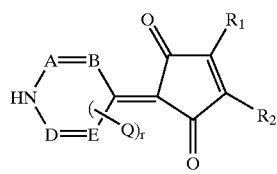
(XI)

[especially of formula XIA,

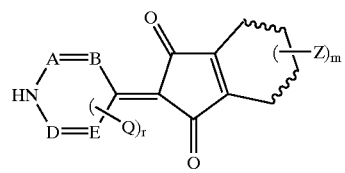
(XIA)]

wherein the radicals are as defined for a compound of formula I [especially formula IA], then reacting the resulting compound of formula XI [especially XIA] with hydrazine, preferably with hydrazine hydrate at a temperature of 100 to 150° C., obtaining a compound of formula IV [especially formula IVA], wherein G is methylene and the other radicals are as defined hereinabove. This compound can then be converted to the corresponding compound of formula II [especially formula IIA], wherein L is halogen, especially chlorine, G is methylene, and the remaining radicals are as defined under formula II [especially IIA], by reaction with a phosphoryl halide or phosphorus pentahalide, especially phosphoryl chloride (POCl$_3$) or phosphorus pentachloride without solvent or in a suitable solvent, for example acetonitrile, at preferred temperatures between 40° C. and reflux temperature, preferably under reflux. Instead of halogen L, another nucleofugal radical can be introduced by substitution under customary conditions.

A compound of formula II [especially formula IIA], wherein G is —CH$_2$—O—, —CH$_2$—S—, —CH$_2$—NH—, oxa, thia, or imino and the remaining radicals are as defined under formula II, can be prepared preferably from a compound of formula XII,

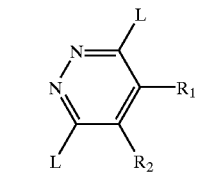
(XII)

[especially of formula XIIA

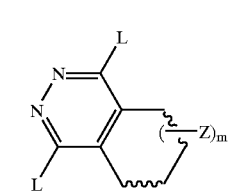
(XIIA)]

wherein L is a nucleofugal leaving group, especially for halogen, such as chlorine, by reacting this with a compound of formula VI, as defined under process c), under conditions as described under process c), the addition of a tertiary amine also being possible. Suitable as tertiary amine is especially ammonia substituted by three radicals selected independently of one another from alkyl, especially lower alkyl, such as methyl or ethyl, and cycloalkyl having from 3 to 7 carbon atoms, especially cyclohexyl, for example N,N-dimethyl-N-cyclohexylamine, N-ethyl-N,N-diisopropylamine or triethylamine, or, furthermore, also pyridine, N-methylmorpholine or 4-dimethylaminopyridine. The tertiary amine is preferably present as a salt with a strong acid, preferably an inorganic acid, typically sulfuric acid, phosphoric acid, or especially a hydrogen halide, such as hydrogen chloride.

Educts of formula XII are known or capable of preparation by processes known perse, for example as described in the German Offenlegungsschrift 2 021 195 (published on Nov. 12, 1970) or the Swiss Patent document no. 516 563, published on Jan. 31, 1972, as described in the J. Chem. Soc. (1948), 777-82 or the Can. J. Chem. 43, 2708–10 (1965), or they are commercially available (such as 1,4-dichlorophthalazine, Aldrich, Milwaukee, USA).

A phthalazinone compound of formula IV, wherein G is methylene and the remaining symbols are as defined under formula I, can be prepared for example as in the process described in J. Med. Chem. 36(25), 4052–60 (1993).

A compound of formula V can for example be obtained by reacting a compound of formula XII, as mentioned above, with a compound of formula III, as defined under process a), under the conditions defined thereunder, the addition of a tertiary amine also being possible. Suitable as tertiary amine is especially ammonia substituted by three radicals selected independently of one another from alkyl, especially lower alkyl, such as methyl or ethyl, and cycloalkyl having from 3 to 7 carbon atoms, especially cyclohexyl, for example N,N-dimethyl-N-cyclohexylamine, N-ethyl-N,N-diisopropylamine or triethylamine, or, furthermore, also pyridine, N-methylmorpholine or 4-dimethylaminopyridine.

A metallate of a compound of formula VI, wherein a bivalent radical —$CH_2$—Me is present instead of the —G—H group, wherein Me is a metal, especially Li or Sn, can be prepared preferably from a corresponding compound of formula VI*

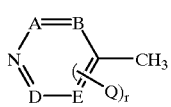

(VI*)

wherein the symbols are as defined for a compound of formula I, by reacting this compound with a corresponding lower alkyl metal, for example tert-butyl lithium or a tri-lower alkyl tin halide, such as tin chloride, in a suitable solvent, such as tetrahydrofuran.

A compound of formula VII is for example obtainable from a compound of formula V under customary reaction conditions, for example by ammonolysis, hydrolysis, or mercaptolysis.

A compound of formula XI, wherein the symbols are as defined above, is also obtainable by reacting a lactone compound of formula XII,

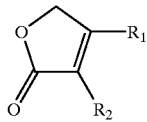

(XIII)

[especially of formula XIIIA,

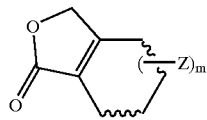

(XIIA)]

wherein the symbols are as defined for a compound of formula I [especially IA], with an aldehyde of formula XIV,

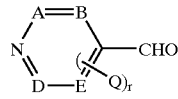

(XIV)

in a solvent, for example an ester, typically ethyl propionate, in the presence of an alcohol, typically methanol, and the corresponding alcoholate, typically an alkali metal methanolate, for example of sodium methanolate, at elevated temperature, preferably under reflux, obtaining the compound of formula XI [especially XIA].

In the preferred embodiment, starting materials of formula XV can be prepared as follows: Starting from a compound of formula XVII

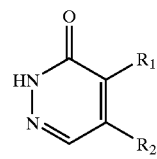

(XVII)

this is first converted by reacting with a phosphoryl halide or phosphorus pentahalide, especially phosphoryl chloride ($POCl_3$) or phosphorus pentachloride without solvent or in a suitable solvent, for example acetonitrile, at preferred temperatures between 40° C. and reflux temperature, preferably under reflux, to the corresponding compound of formula XVIII,

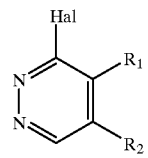

wherein the radicals are as defined for compounds of formula I; the compound is then reacted with a compound of formula XIX

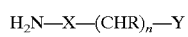

$H_2N$—X—$(CHR)_n$—Y    (XIX)

wherein the radicals and symbols are as described for compounds of formula I, under conditions as described under process a); the obtainable compound of formula XX,

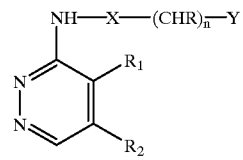

(XX)

wherein the radicals and symbols are as defined for compounds of formula I, is then reacted in the presence of a suitable solvent, such as dichloromethane, with aluminium chloride and tri-lower alkylsilylcyanide, such as trimethylsilyl cyanide, and then with an acyl chloride, such as benzoyl chloride, preferably at temperatures between −10 and 40° C., for example at about 0° C., preferably under inert gas, such as nitrogen, resulting in the compound of formula XV.

The starting materials are known, capable of being prepared according to known processes, or commercially available; in particular, they can be prepared using processes as described in the Examples.

EXAMPLES

The following Examples serve to illustrate the invention without limiting the invention in its scope.

Temperatures are measured in degrees celsius. Unless otherwise indicated, the reactions take place at room temperature.

| HPLC gradients: | |
|---|---|
| Grad$_{20-100}$ | 20% → 100% a) in b) for 13 min + 5 min 100% a). |
| Grad$_{5-40}$ | 5% → 40% a) in b) for 7.5 min + 7 min 40% a). |

Eluent a): acetonitrile+0.05% TFA; eluent b): water+0.05% TFA. Column (250×4.6 mm) packed with reversed-phase material C18-Nucleosil (5 μm mean particle size, with silica gel covalently derivatized with octadecylsilanes, Macherey & Nagel, Düren, Germany). Detection by UV absorption at 254 nm. The retention times ($t_{Ret}$) are given in minutes. Flow rate: 1 ml/min.

| The short forms and abbreviations used have the following definitions: | |
|---|---|
| abs. | absolute (non-aqueous solvent) |
| DIPE | diisopropyl ether |
| DMSO | dimethyl sulfoxide |
| DMEU | 1,3-dimethyl-2-imidazolidone |
| DMF | dimethylformamide |
| ESI-MS | electrospray ionization mass spectroscopy |
| Acetate | ethyl acetate |
| Ether | diethyl ether |
| FAB-MS | fast atom bombardment mass spectroscopy |
| sat. | saturated |
| h | hour(s) |
| HV | high vacuum |
| min | minute(s) |
| RT | room temperature |
| RE | rotary evaporator |
| m.p. | melting point |
| Brine | saturated sodium chloride solution |
| THF | tetrahydrofuran (distilled over sodium benzophenone) |

The following starting materials are obtained from the suppliers indicated:

4-Chloroaniline, 3-chloroaniline, aniline, benzylamine, 4-methoxyaniline, 3-methoxyaniline, 4-aminoacetanilide, (S)-1-phenylethylamine, (R)-1-phenylethylamine, 4-aminobenzotrifluoride (=4-(trifluoromethyl)aniline), 4-fluoroaniline, 1,3-phenylenediamine, methanesulfonic acid, 3,4-dichloroaniline, 4-bromoaniline: Fluka, Buchs, Switzerland. 3-Benzyloxyaniline, 2-aminophenol, 4-aminophenol: Aldrich, Buchs, Switzerland.

1-Chloro-4-(4-pyridylmethyl)phthalazine is prepared according to known processes (see German Auslegeschrift no. 1 061 788 [published Jul. 23, 1959]).

Hyflo Super Cel is diatomaceous earth which is used as a filtration aid (Fluka, Buchs, Switzerland).

Example 1

1-(4-Chloroanilino)-4-(4-pyridylmethyl)phthalazine dihydrochloride

A mixture of 15.22 g (59.52 mmol) 1-chloro-4-(4-pyridylmethyl)phthalazine (for preparation see German Auslegeschrift no. 1 061 788 [published Jul. 23, 1959]), 7.73 g (60.59 mmol) 4-chloroaniline and 200 ml 1-butanol is heated for 2 h under reflux. The crystallizate which is obtained when the mixture slowly cools to 5° C. is then filtered off and washed with 1-butanol and ether. The filter residue is dissolved in about 200 ml hot methanol, the solution is treated with 0.75 g activated carbon and filtered via a Hyflo Super Cel, and the pH of the filtrate is adjusted to about 2.5 with 7 ml 3N methanolic HCl. The filtrate is evaporated to about half the original volume and ether added until slight turbidity occurs; cooling then leads to the precipitation of crystals. The crystallizate is filtered off, washed with a mixture of methanol/ether (1:2) as well as ether, dried for 8 h at 110° C. under HV, and equilibrated for 72 h at 20° C. and in room atmosphere. In this way, the title compound is obtained with a water content of 8.6%; m.p. >270° C.; $^1$H NMR (DMSO-d$_6$) 11.05–12.20 (br), 9.18–9.23 (m, 1H), 8.88 (d, 2H), 8.35–8.40 (m, 1H), 8.18–8.29 (m, 2H), 8.02 (d, 2H), 7.73 (d, 2H), 7.61 (d, 2H), 5.02 (s, 2H); ESI-MS: (M+H)$^+$=347.

Example 2

1-(4-Chloroanilino)-4-(4-pyridylmethyl)phthalazine hydrochloride

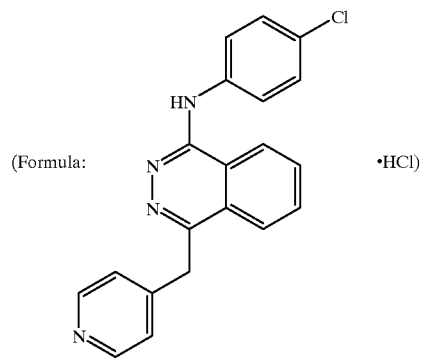

(Formula: ·HCl)

A mixture of 0.972 g (3.8 mmol) 1-chloro-4-(4-pyridylmethyl)phthalazine, 0.656 g (4 mmol) 4-chloroaniline hydrochloride (Research Organics, Inc., Cleveland, Ohio, USA) and 20 ml ethanol is heated for 2 h under reflux. The reaction mixture is cooled in an ice bath, filtered, and the crystallizate washed with a little ethanol and ether. After drying under HV for 8 h at 110° C. and for 10 h at 150° C., the title compound is obtained as a result of thermal removal of HCl; m.p. >270° C.; $^1$H NMR (DMSO-d$_6$) 9.80–11.40 (br), 8.89–8.94 (m, 1H), 8.67 (d, 2H), 8.25–8.30 (m, 1H), 8.06–8.17 (m, 2H), 7.87 (d, 2H), 7.69 (d, 2H), 7.49 (d, 2H), 4.81 (s, 2H); ESI-MS: (M+H)$^+$=347.

Example 3

1-(4-Chloroanilino)-4-(4-pyridylmethyl)phthalazine hydrochloride

A mixture of 1.28 g (5 mmol) 1-chloro-4-(4-pyridylmethyl)phthalazine, 0.67 g (5.25 mmol) 4-chloroaniline and 15 ml 1-butanol is heated for 0.5 h at 100 h while stirring in a nitrogen atmosphere. The mixture is then cooled to RT, filtered, and the filtrate washed with 1-butanol and ether. For purification, the crystallizate is dissolved in 40 ml of hot methanol, the solution treated with activated carbon, filtered via Hyflo Super Cel, and the filtrate evaporated to about half its original volume, resulting in the formation of a crystalline precipitate. After cooling to 0° C., filtration, washing of the filter residue with ether, and drying under HV for 8 h at 130° C., the title compound is obtained; m.p. >270° C.; $^1$H NMR (DMSO-d$_6$) 9.80–11.40 (br), 8.89–8.94 (m, 1 H), 8.67 (d, 2H), 8.25–8.30 (m, 1 H), 8.06–8.17 (m, 2H), 7.87 (d, 2H), 7.69 (d, 2H), 7.49 (d, 2H), 4.81 (s, 2H); ESI-MS: (M+H)$^+$=347.

Example 4

1-(4-Chloroanilino)-4-(4-pyridylmethyl)phthalazine

A mixture of 14.19 g (0.1 mol) phosphorus pentoxide, 13.77 g (0.1 mol) triethylamine hydrochloride and 12.76 g (0.1 mol) 4-chloroaniline is heated and stirred in a nitrogen atmosphere at 200° C. until a homogeneous melt has formed (about 20 min). To the melt, 5.93 g (0.025 mol) 4-(4-pyridylmethyl)-1 (2H)-phthalazinone (for preparation see German Auslegeschrift no. 1 061 788 [published Jul. 23, 1959]) is added, and the reaction mixture is stirred for 3 h at 200° C. After the reaction mixture has cooled to about 100° C., 200 ml of water is added. Stirring is continued until the temperature reaches about 30° C., and then 20 ml conc. ammonia (30% aqueous ammonium hydroxide solution) and 900 ml chloroform are added consecutively. As soon as a diphasic mixture has formed, the organic phase is separated off, dried over anhydrous sodium sulfate, filtered, and the filtrate evaporated on a RE to a volume of about 50 ml, to which 100 ml acetate is then added, and the mixture is cooled in an ice bath. The crystallizate obtained is filtered off and washed with acetate and ether. After recrystallization from methanol and drying under HV for 8 h at 120° C., the title compound is obtained; m.p. 194–195° C.; ESI-MS: $(M+H)^+=347$.

Example 5

1-(3-Chloroanilino)-4-(4-pyridylmethyl)phthalazine 1,8 hydrochloride

A mixture of 1.28 g (5 mmol) 1-chloro-4-(4-pyridylmethyl)phthalazine und 2.6 ml (25 mmol) 3-chloroaniline is stirred for 45 min at 90° C. under a nitrogen atmosphere. Excess 3-chloroaniline is then distilled off under HV at 60° C. and the residue distributed between 30 ml dichloromethane and 20 ml of 20% aqueous potassium carbonate solution. The organic solution dried over anhydrous sodium sulfate is evaporated and the residue purified on silica gel by flash chromatography using acetate and acetate/methanol (20:1). The product-containing fractions are dissolved in 3 ml of methanol, and acidified with 2.3 ml 3N methanolic HCl, then ether is added while stirring until slight turbidity occurs, and the mixture is cooled to 0° C., resulting in the formation of a crystalline precipitate. After filtration, washing of the filter residue with ether, drying under HV (8 h, 110° C.) and equilibration for 65 h at 20° C. and in room atmosphere, the title compound is obtained with a water content of 7.3%; Smp. 233–236° C.; ESI-MS: $(M+H)^+=347$.

Example 6

1-Anilino-4-(4-pyridylmethyl)phthalazine dihydrochloride

By analogy with Example 5, title compound with a water content of 7.96% is obtained starting from 1.28 g (5 mmol) 1-chloro-4-(4-pyridylmethyl)phthalazine and 1.37 ml (15 mmol) aniline and using 2.5 ml 3N methanolic HCl; m.p. 217–220° C.; ESI-MS: $(M+H)^+=313$.

Example 7

1-Benzylamino-4-(4-pyridylmethyl)phthalazine

A mixture of 1.28 g (5 mmol) 1-chloro-4-(4-pyridylmethyl)phthalazine and 1.64 ml (15 mmol) benzylamine is stirred for 4 min at 90° C. under a nitrogen atmosphere. The reaction mixture is then distributed between dichloromethane and 20% aqueous potassium carbonate solution. The organic phase dried over anhydrous sodium sulfate is evaporated and the residue purified on silica gel by flash chromatography using acetate and acetate/methanol (20:1). Title compound is obtained after crystallization of the product-containing fractions from acetonitrile and drying under HV (8 h, 80° C.); m.p. 137–138° C.; ESI-MS: $(M+H)^+=327$.

Example 8

1-(4-Methoxyanilino)-4-(4-pyridylmethyl) phthalazine

By analogy with Example 7, title compound is obtained starting from 1.28 g (5 mmol) 1-chloro-4-(4-pyridylmethyl) phthalazine and 1.85 g (15 mmol) 4-methoxyaniline, but with a reaction time of 2 h and crystallization from acetate; m.p. 223–224° C.; ESI-MS: $(M+H)^+=343$.

Example 9

1-(3-Benzyloxyanilino)-4-(4-pyridylmethyl) phthalazine

By analogy with Example 7, title compound is obtained starting from 0.767 g (3 mmol) 1-chloro-4-(4-pyridylmethyl)phthalazine and 1.793 g (9 mmol) 3-benzyloxyaniline with a reaction time of 2 h; m.p. 142–143° C.; ESI-MS: $(M+H)^+=419$.

Example 10

1-(3-Methoxyanilino)-4-(4-pyridylmethyl) phthalazine

By analogy with Example 7, title compound is obtained starting from 1.28 g (5 mmol) 1-chloro-4-(4-pyridylmethyl) phthalazine and 1.68 ml (15 mmol) 3-methoxyaniline with a reaction time of 2 h; m.p. 118–120° C.; ESI-MS: $(M+H)^+=343$.

Example 11

1-(4-Acetaminoanilino)-4-(4-pyridylmethyl) phthalazine

A mixture of 0.511 g (2 mmol) 1-chloro-4-(4-pyridylmethyl)phthalazine, 0.901 g (6 mmol) 4-aminoacetanilide and 5 ml 1-butanol is heated for 3 h at 110° C. The reaction mixture is then evaporated under vacuum, the crystalline residue is taken up in a mixture of 20 ml dichloromethane and 10 ml 20% aqueous potassium carbonate solution while stirring, then filtered and the filter residue washed with water and dichloromethane. After recrystallization from dichloromethane/methanol and drying under HV (8 h, 100° C.), title compound is obtained with a methanol content of 1.27%;

m.p. >270° C.; $^1$H NMR (DMSO-$d_6$) 9.91 (s, 1H), 9.13 (s, 1H), 8.59–8.64 (m, 1H), 8.84 (d, 2H), 8.08–8.13 (m, 1 H), 7.91–8.01 (m, 2H), 7.85 (d, 2H), 7.58 (d, 2H), 7.32 (d, 2H), 4.58 (s, 2H), 2,05 (s, 3H), [methanol: 4.13 (q, 0.15H), 3.19 (d, 0.45H)]; ESI-MS: $(M+H)^+=370$.

Example 12

(S)-1-(1-Phenylethylamino)-4-(4-pyridylmethyl) phthalazine 1.85 hydrochloride

A mixture of 0.511 g (2 mmol) 1-chloro-4-(4-pyridylmethyl)phthalazine, 1.273 ml (10 mmol) (S)-1phenylethylamine and 5 ml 1-butanol is stirred for 24 h at 110° C. The reaction mixture is evaporated under vacuum and the residue distributed between dichloromethane and 20% aqueous potassium carbonate solution. The organic phase dried over anhydrous sodium sulfate is evaporated in the RE and then under HV and the residue purified on silica gel by flash chromatography using dichloromethane/methanol (50:1). The product-containing fractions are dissolved in 5 ml methanol, acidified with 0.75 ml 3N methanolic HCl and evaporated under vacuum. After recrystallization of the residue from methanol/acetonitrile, drying of the crystallizate under HV (8 h, 100° C.) and equilibration for 15 h at 20° C. and in room atmosphere, title compound is obtained with a water content of 10.66%; m.p. 190° C. (decomp.); ESI-MS: (M+H)$^+$=341; $[a]_D^{20}$=+42.1±0.8° (c=1.272%, methanol).

Example 13

(R)-1-(1-Phenylethylamino)-4-(4-pyridylmethyl)phthalazine dihydrochloride

A mixture of 0.511 g (2 mmol) 1-chloro-4-(4-pyridylmethyl)phthalazine, 1.273 ml (10 mmol) (S)-1phenylethylamine and 5 ml 1-butanol is stirred for 40 h at 110° C. After processing as described in Example 12 and equilibration for 65 hours at 20° C. and in room atmosphere, title compound is obtained with a water content of 10.53%; m.p. 190° C. (decomp.); ESI-MS: (M+H)$^+$=341; $[a]_D^{20}$=+38.4±0.7° (c=1.507%, methanol).

Example 14

1-(2-Methoxyanilino)-4-(4-pyridylmethyl)phthalazine

By analogy with Example 7, title compound is obtained starting from 0.511 g (2 mmol) 1-chloro-4-(4-pyridylmethyl)phthalazine and 0.677 ml (6 mmol) 3-methoxyaniline with a reaction time of 1 h; m.p. 190–191° C.; ESI-MS: (M+H)$^+$=343.

Example 15

1-(3-Pyridylamino)-4-(4-pyridylmethyl)phthalazine

A mixture of 0.511 g (2 mmol) 1-chloro-4-(4-pyridylmethyl)phthalazine and 0.565 g (6 mmol) 3-aminopyridine is heated for 3 h at 90° C. The residue is then distributed between acetate and 20% aqueous potassium carbonate solution. The organic phase dried over anhydrous sodium sulfate is evaporated and the residue purified on silica gel by flash chromatography using acetate/methanol mixtures (49:1 to 4:1). Title compound is obtained after crystallization of the product-containing fractions from acetonitrile and drying under HV (6 h, 80° C.); m.p. 137–139° C.; ESI-MS: (M+H)$^+$=314.

Example 16

1-(4-Trifluoromethylanilino)-4-(4-pyridylmethyl)phthalazine

A mixture of 0.511 g (2 mmol) 1-chloro-4-(4-pyridylmethyl)phthalazine and 0.746 ml (6 mmol) 4-aminobenzotrifluoride is heated for 2.5 h at 100° C. The reaction mixture is then distributed between acetate and 20% aqueous potassium carbonate solution. The title compound is obtained after further processing as described in Example 7; m.p. 205–206° C.; ESI-MS: (M+H)$^+$=381.

Example 17

1-(4-Fluoroanilino)-4-(4-pyridylmethyl)phthalazine

A mixture of 0.511 g (2 mmol) 1-chloro-4-(4-pyridylmethyl)phthalazine and 0.576 ml (6 mmol) 4-fluoroaniline is heated for 2 h at 90° C. The residue is then distributed between acetate and 20% aqueous potassium carbonate solution. The organic phase washed with water and dried over sodium sulfate is evaporated and the residue purified on silica gel by flash chromatography using acetate/methanol mixtures (50:1 and 25:1). Title compound is obtained after crystallization of the product-containing fractions from acetonitrile and drying under HV (6 h, 100° C.); m.p. 129–131° C.; ESI-MS: (M+H)$^+$=331.

Example 18

1-(3-Hydroxyanilino)-4-(4-pyridylmethyl)phthalazine

A mixture of 0.384 g (1.5 mmol) 1-chloro-4-(4-pyridylmethyl)phthalazine and 0.491 g (4.5 mmol) 3-aminophenol is heated under nitrogen atmosphere for 1 h at 90° C. and for 3 h at 120° C. The reaction mixture is then taken up in a mixture of 30 ml acetate and 20 ml 20% aqueous potassium carbonate solution while stirring for about 4 h, and the filtration material is digested for 20 min in 20 ml of boiling methanol. After cooling to RT, filtration, washing of the filter residue with methanol, and drying under HV (8 h, 130° C.), title compound is obtained with a water content of 1.94%; m.p. 217–219° C.; ESI-MS: (M+H)$^+$=329.

Example 19

1-(4-Hydroxyanilino)-4-(4-pyridylmethyl)phthalazine

A mixture of 0.384 g (1.5 mmol) 1-chloro-4-(4-pyridylmethyl)phthalazine and 0.491 g (4.5 mmol) 4-aminophenol is heated under nitrogen atmosphere for 2 h at 150° C. After processing as described in Example 18, drying under HV (8 h at 100° C. and 24 h at 145° C.), title compound is obtained with a water content of 0.68%; m.p. 239–241° C.; $^1$H NMR (DMSO-d$_6$) 9.19 (s, 1H), 8.99 (brs, 1H), 8.56 (d, 1H), 8.44 (d, 2H), 8.06 (d, 1H), 7.86–7.96 (m, 2H), 7.61 (d, 2H), 7.30 (d, 2H), 6.77 (d, 2H), 4.53 (s, 2H); ESI-MS: (M+H)$^+$=329.

Example 20

1-(3-Aminoanilino)-4-(4-pyridylmethyl)phthalazine trimesylate

A mixture of 0.384 g (1.5 mmol) 1-chloro-1,3-(4-pyridylmethyl)phthalazine and 0.487 g (4.5 mmol) phenylenediamine is stirred for 1 h at 90° C. under a nitrogen atmosphere. The residue is then distributed between acetate and 20% aqueous potassium carbonate solution. The organic phase dried over anhydrous sodium sulfate is evaporated and the residue purified on silica gel by flash chromatography using acetate/methanol mixtures (49:1 to 9:1). The product-containing fractions are dissolved in 3 ml methanol, and a solution of 0.16 ml (2.47 mmol) methanesulfonic acid in 1 ml methanol is first stirred in, then hexane is stirred in until slight turbidity occurs, and the mixture is cooled in an ice bath, resulting in the formation of a crystalline precipitate. After filtration and drying under HV (8 h at 100° C.), the title compound is obtained; m.p. 249–251° C.; ESI-MS: (M+H)$^+$=328.

Example 21

1-(3,4-Dichloroanilino)-4-(4-pyridylmethyl)phthalazine

A mixture of 0.384 g (1.5 mmol) 1-chloro-3,4-(4-pyridylmethyl)phthalazine and 0.729 g (4.5 mmol)

4-dichloroaniline is heated under nitrogen atmosphere for 2 h at 90° C. The reaction mixture is then taken up in a mixture of 30 ml acetate and 20 ml 20% aqueous potassium carbonate solution while stirring, and the organic phase dried over anhydrous sodium sulfate is filtered and evaporated under vacuum. The filtration material and the evaporation residue are combined and purified on silica gel by flash chromatography using acetate/methanol (50:1 and 25:1). Title compound is obtained after crystallization of the product-containing fractions from dichloromethane/methanol and drying under HV (8 h, 110° C.); m.p. 249–250° C.; ESI-MS: $(M+H)^+=381$ und 383 (2 peaks through isotope content of the two chlorine atoms).

Example 22

1-(4-Bromoanilino)-4-(4-pyridylmethyl)phthalazine

A mixture of 0.384 g (1.5 mmol) 1-chloro-4-(4-pyridylmethyl)phthalazine and 0.774 g (4.5 mmol) 4-bromoaniline is heated under nitrogen atmosphere for 1.5 h at 90° C. The process is then carried out as in Example 21. Title compound is obtained after recrystallization from acetate/hexane and drying under HV (8 h at 100° C.); m.p. 201–202° C.; ESI-MS: $(M+H)^+=391$ und 393.

Example 23

1-(3-Chloro-4-methoxyanilino)-4-(4-pyridylmethyl)phthalazine

By analogy with Example 22, title compound is obtained starting from 0.384 g (1.5 mmol) 1-chloro-4-(4-pyridylmethyl)phthalazine and 0.709 g (4.5 mmol) 3-chloro-4-methoxyaniline after recrystallization of product purified from acetonitrile and methanol/acetonitrile by means of flash chromatography; m.p. 195–197° C.; ESI-MS: $(M+H)^+=377$.

Example 24

1-(4-Cyanoanilino)-4-(4-pyridylmethyl)phthalazine

A mixture of 0.384 g (1.5 mmol) 1-chloro-4-(4-pyridylmethyl)phthalazine and 0.532 g (4.5 mmol) 4-aminobenzonitrile is heated for 1.5 h at 90° C. The reaction mixture is then distributed between dichloromethane and 20% aqueous potassium carbonate solution. The organic phase washed with water and dried over sodium sulfate is evaporated and the residue purified on silica gel by flash chromatography using acetate/methanol mixtures (50:1 and ). 25:1). Title compound is obtained after crystallization of the product-containing fractions from dichloromethane and drying under HV (8 h, 90° C.); m.p. 228–230° C.; ESI-MS: $(M+H)^+=338$.

Example 25

7-Acetamino-1-(4-chloroanilino)-4-(4-pyridylmethyl)phthalazine hydrochloride

Under exclusion of air, 207 mg (0.66 mmol) 7-acetamino-1-chloro-4-(4-pyridylmethyl)phthalazine is heated to boiling for 4 h in 2.7 ml 1-butanol with 253 mg (1.98 mmol) 4-chloroaniline. After cooling, the dark suspension is filtered off, washed with 1-butanol and ethanol, and dried to obtain title compound: m.p.: 260–265° C.; HPLC: $t_{Ret}(Grad_{5-40})$=10.9; FAB MS $(M+H)^+=404$.

The starting material is prepared as follows:

25.1) 7-Acetamino-1-chloro-4-(4-pyridylmethyl)phthalazine

Under a nitrogen atmosphere, a suspension of 2.24 g (7.6 mmol) 7-acetamino-1-hydroxy-4-(4-pyridylmethyl)phthalazine hydrochloride ($\equiv$1-oxo-4-[pyridyl-(4')-methyl]-7-acetamino-1,2-dihydrophthalazine hydrochloride: for preparation see German Auslegeschrift no. 1 061 788 [published Jul. 23, 1959]) in 22 ml acetonitrile is spiked with 1.74 ml (19 mmol) phosphoroxychloride and heated for 4 h to 95° C. The mixture is cooled to 10° C., and 7.5 g NaHCO$_3$ in 30 ml water is added. The deep-red suspension is stirred for 15 min, filtered, and washed out with water. Drying under HV yields the title compound: HPLC: $t_{Ret}(Grad_{5-40})$=10.2; FAB MS $(M+H)^+=313$.

Example 26

7-Acetamino-1-(4-methoxyanilino)-4-(4-pyridylmethyl)phthalazine hydrochloride

Under exclusion of air, 354 mg (2.88 mmol) 4-methoxyaniline and 13 mg lithium iodide are added to 300 mg (0.96 mmol) 7-acetamino-1-chloro-4-(4-pyridylmethyl)phthalazine in 3.9 ml 1-butanol and heated to boiling for 20 h. After cooling, the dark suspension is filtered off, washed with 1-butanol and ethanol, and dried to obtain title compound: m.p.: 160–163° C.; HPLC: $t_{Ret}(Grad_{5-40})$=9.5; FAB MS $(M+H)^+=400$.

Example 27

7-Acetamino-1-(3-methoxyanilino)-4-(4-pyridylmethyl)phthalazine hydrochloride

By analogy with 25, 300 mg (0.96 mmol) 7-acetamino-1-chloro-4-(4-pyridylmethyl)phthalazine is reacted in 3.9 ml 1-butanol with 321 µl (2.88 mmol) 3-methoxyaniline to obtain title compound: m.p.: 156–159° C.; HPLC: $t_{Ret}(Grad_{5-40})$=11.0; FAB MS $(M+H)^+=400$.

Example 28

7-Acetamino-1-(3-chloroanilino)-4-(4-pyridylmethyl)phthalazine hydrochloride

By analogy with Example 25, 300 mg (0.96 mmol) 7-acetamino-1-chloro-4-(4-pyridylmethyl)phthalazine is reacted in 3.9 ml 1-butanol with 302 µl (2.88 mmol) 3-chloroaniline. Suspension of the raw product in 1 ml boiling ethanol and filtration lead to the title compound: HPLC: $t_{Ret}(Grad_{5-40})$=11.3; FAB MS $(M+H)^+=404$.

Example 29

7-Acetamino-1-anilino-4-(4-pyridylmethyl)phthalazine hydrochloride

By analogy with Example 25, 250 mg (0.80 mmol) 7-acetamino-1-chloro-4-(4-pyridylmethyl)phthalazine is reacted in 3.2 ml 1-butanol with 0.22 ml (2.4 mmol) aniline to obtain title compound: m.p.: 162–166° C.; HPLC: $t_{Ret}(Grad_{5-40})$=9.75; FAB MS $(M+H)^+=370$.

The following Examples 31 and 33 to 36 are prepared in the same manner as in the Examples or processes described hereinbefore.

Example 30

7-Acetamino-1-(3,4-dichloroanilino)-4-(4-pyridylmethyl)phthalazine hydrochloride The preparation is carried out in the manner described under Example 25, starting from 7-acetamino-1-chloro-4-(4-pyridylmethyl)phthalazine and 3,4-dichloroaniline.

Example 31

7-(Benzoyloxycarbonylamino)-1-(4-chloroanilino)-4-(4-pyridylmethyl)phthalazine hydrochloride The preparation is carried out starting from 7-amino-1-(4-chloroanilino)-4-(4-pyridylmethyl)phthalazine and carbobenzoxy chloride.

Example 32

A: 7-Amino-1-(4-chloroanilino)-4-(4-pyridylmethyl)phthalazine hydrochloride

Under exclusion of air, 381 mg (0.77 mmol) 7-trifluoroacetamino-1-chloro-4-(4-pyridylmethyl) phthalazine is heated to 100° C. for 5 h in 3.1 ml n-butanol with 295 mg (2.31 mmol) 4-chloroaniline. After cooling, the dark suspension is filtered off, washed with n-butanol and ethanol, and dried to obtain title compound: m.p.: >300° C.; HPLC: $t_{Ret}(Grad_{5-40})$=12.9; FAB MS $(M+H)^+$=362. With DIPE, further product may be precipitated out from the filtrate. The starting material is prepared as follows:

32A.1) 7-Trifluoroacetamino-4-(4-pyridylmethyl)-1(2H)-phthalazinone hydrochloride A suspension of 500 mg (1.98 mmol) 7-amino-4-(4-pyridylmethyl)-1(2H)-phthalazinone [≡1-oxo-4-[pyridyl-(4')-methyl]-7-amino-1,2-dihydrophthalazine (for preparation see German Auslegeschrift no. 1061788 [published Jul. 23, 1959]) in 1.65 ml (11.88 mmol) trifluoroacetic acid anhydride is stirred over the weekend at RT. Addition of water and sonication yield a suspension which can be filtered and washed out with water. The crystals are suspended in 15 ml acetic acid. When 2.47 ml of a 2.4 M solution of HCl in dioxane is added, the suspension dissolves, and scraping eventually leads to renewed crystallization. Filtering and washing with ethyl acetate yield the title compound; HPLC: $t_{Ret}(Grad_{5-40})$=11.3; FAB MS $(M+H)^+$=349.

32A.2) 7-Trifluoroacetamino-1-chloro-4-(4-pyridylmethyl)phthalazine

Under $N_2$ atmosphere, 552 mg (1.44 mmol) 7-trifluoroacetamino-4-(4-pyridylmethyl)-1(2H)-phthalazinone hydrochloride is added to 4.2 ml acetonitrile 0.328 ml (3.58 mmol) phosphoroxychloride and heated for 4 h to 100° C. This is then cooled to 10° C., and 1.4 g $NaHCO_3$ in 7 ml water is added. After ethyl acetate is added, a reddish suspension forms which is filtered and washed out. Drying under HV yields the title compound: HPLC: $t_{Ret}(Grad_{5-40})$=12.1; FAB MS $(M+H)^+$=367.

The following compounds are prepared in the same manner:

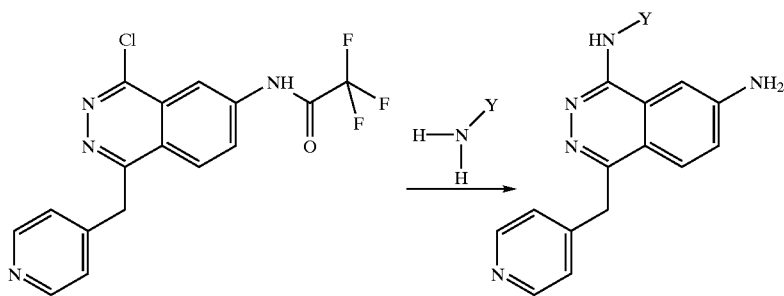

| Example | $H_2N$—Y | —HN-Y | HPLC: $t_{Ret}$ | FAB MS $(M+H)^+$ |
|---|---|---|---|---|
| 32B | 3-chloroaniline (1) | 3-chloro-HN-phenyl | 10.5 | 362 |
| 32C | aniline (1,2) | HN-phenyl | 9.0 | 328 |
| 32D | 4-methylaniline (1,2) | HN-(4-methylphenyl) | 10.3 | 342 |

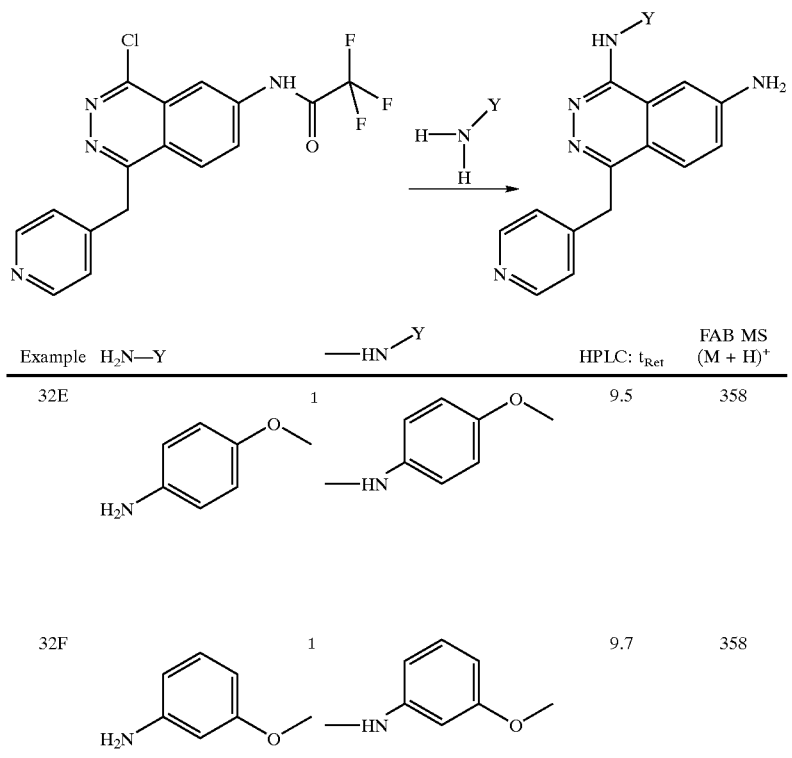

| Example | H₂N—Y | —HN-Y | HPLC: $t_{Ret}$ | FAB MS $(M + H)^+$ |
|---|---|---|---|---|
| 32E | H₂N–C₆H₄–OCH₃ (para) | —HN–C₆H₄–OCH₃ (para) | 9.5 | 358 |
| 32F | H₂N–C₆H₄–OCH₃ (meta) | —HN–C₆H₄–OCH₃ (meta) | 9.7 | 358 |

HPLC:(Grad₅₋₄₀)
[1] Fluka, Buchs/Switzerland;
[2] Product accumulates as a mixture of 7-amino- and 7-trifluoroacetamino- derivative → treatment with CH₃OH/NH₃ (aq. 25%) 9:1 at RT completely removes the trifluoroacetate.

Example 33

7-(3-Nitrobenzoylamino)-1-(4-chloroanilino)-4-(4-pyridylmethyl)phthalazine hydrochloride Preparation is carried out starting from the title compound from Example 32A and 3-nitrobenzoyl chloride.

Example 34

7-(3-Aminobenzoylamino)-1-(4-chloroanilino)-4-(4-pyridylmethyl)phthalazine hydrochloride Preparation is carried out by reduction of the title compound from Example 33.

Example 35

7-(2-Hydroxyethylamino)-1-(4-chloroanilino)-4-(4-pyridylmethyl)phthalazine hydrochloride Starting from the title compound from Example 32A, preparation is carried out by reductive alkylation with O-protected hydroxyacetaldehyde and removal of the protecting group.

Example 36

7-Bromo-1-(4-chloroanilino)-4-(4-pyridylmethyl) phthalazine hydrochloride

The preparation is carried out starting from 7-bromo-1-chloro-4-(4-pyridylmethyl)phthalazine and 4-chloroaniline.

The starting material is prepared as follows:

36.1) 5-Bromo-2-(1H-pyridin-4-ylidene)-indan-1,3-dione

Under N₂ atmosphere, a mixture of 30 g (132 mmol) 5-bromoisobenzofuran-1,3-dione (≡4-bromophthalic acid anhydride; Apin, GB) and 12.87 ml (132 mmol) 4-picoline is heated for 15 h to 180° C. The resulting black mass is cooled to 100° C., mixed with 160 ml ethanol, boiled for 2 hours, and filtered off. The dried residue is triturated in a mortar, boiled further for 1 h in 180 ml ethanol, filtered, and washed with ethanol. The residue is dissolved at 140° C. in 90 ml DMEU, cooled, mixed with 250 ml ethyl acetate and filtered (→residue is washed out with ethyl acetate and discarded). The ethyl acetate from the filtrate is evaporated off and the residue then diluted with 260 ml acetonitrile, the title compound crystallizing out in the process: HPLC: $t_{Ret}$(Grad₂₀₋₁₀₀)=10.4; MS (M)⁺=301/303.

36.2) 1-Oxo-4-[(pyridin-4-yl)-methyl]-7-bromo-1,2-dihydrophthalazine

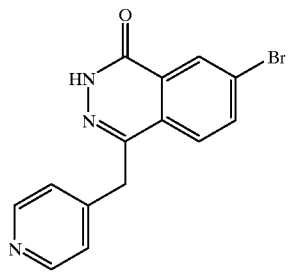

A

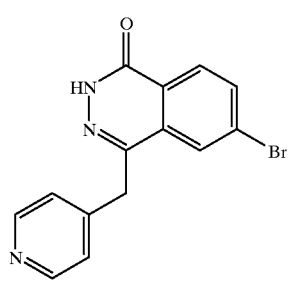

B

Under exclusion of air, 4.75 g (15.7 mmol) 5-bromo-2-(1H-pyridin-4-ylidene)indan-1,3-dione and 14 ml hydrazine hydrate are heated for 4 h to 130° C. Cooling, filtering, and washing with ethanol yields title compound A in the mixture with a little 1-oxo-4-[(pyridin-4-yl)-methyl]-6-bromo-1,2-dihydrophthalazine (B). A: HPLC: $t_{Ret}(Grad_{5-40})$=1.5; $^1$H-NMR (DMSO-$d_6$) 12.76 (HN), 8.46 (d, J=6, 2H), 8.34 (d, J=2, 1H), 8.07 (dd, J=8, 2, 1H), 7.85 (d, J=8, 1H), 7.30 (d, J=6, 2H), 4.33 (s, 2H); B: HPLC: $t_{Ret}(Grad_{5-40})$=11.3; $^1$H-NMR (DMSO-$d_6$) 12.76 (HN), 8.46 (d, J=6, 2H), 8.16 (d, J=8, 1H), 8.14 (d, J=2, 1H), 8.00 (dd, J=8, 2, 1H), 7.3 (d, J=6, 2H), 4.35 (s, 2H).

36.3) 7-Bromo-1-chloro-4-(4-pyridylmethyl)phthalazine

Example 37

1-(4-Methylanilino)-4-(4-pyridylmethyl)phthalazine

A mixture of 0.384 g (1.5 mmol) 1-chloro-4-(4-pyridylmethyl)phthalazine and 0.482 g (4.5 mmol) p-toluidine is stirred for 1.5 h at 90° C. under a nitrogen atmosphere. The reaction mixture is then distributed between 30 ml acetate and 20% aqueous potassium carbonate solution. The organic phase washed with water and dried over anhydrous sodium sulfate is evaporated and the residue purified on silica gel by flash chromatography using acetate/methanol mixtures (50:1 to 9:1). Title compound is obtained after crystallization of the product-containing fractions from acetonitrile and drying under HV; m.p. 152–153° C.; ESI-MS: (M+H)$^+$=327.

Example 38

1-(4-Chloroanilino)-4-(4-pyridylmethyl)phthalazine

A mixture of 17.03 g (0.12 mol) phosphorus pentoxide, 11.56 g (0.084 mol) triethylamine hydrochloride and 15.31 g (0.12 mol) 4-chloroaniline is heated and stirred under argon atmosphere at 200° C. (oil bath temperature) until a homogeneous melt has formed (about 45 min). To the melt (internal temperature about 160° C.) 7.12 g (0.03 mol) of 4-(4-pyridylmethyl)-1(2H)-phthalazinone (for preparation see German Auslegeschrift no. 1 061 788 [published Jul. 23, 1959]) is added and the reaction mixture stirred for 4 h at an internal temperature of 160–170° C. After cooling to about 120° C. (internal temperature)28 ml tetramethylurea is added dropwise, the temperature rising temporarily to 150° C. For about 10 min at 120° C., 100 ml water is then added to the reaction mixture, which is stirred for 0.5 h at 100–103° C. (internal temperature), then cooled to 60° C., before a mixture of 40 ml water and 37 ml concentrated ammonia solution is added dropwise to the brown solution, whereupon a suspension forms. While cooling to an ultimate temperature of 15° C., the suspension is stirred for 0.5 h, then mixed with 80 ml ether and stirred for a further 10 min. The mixture is filtered, the filter residue is washed with water, then ether, and dried in air. After recrystallization from methanol/ether (under treatment with activated carbon) and drying under HV for 8 h at 120° C., the title compound is obtained with a water content of 0.31%; m.p. 207–209° C.; $^1$H NMR (DMSO-$d_6$) 9.29 (s, 1H), 8.58–8.63 (m, 1H), 8.44–8.47 (m, 2H), 8.10–8.15 (m, 1H), 7.89–8.05 (m, 4H), 7.37–7.45 (m, 2H), 7.31–7.34 (m, 2H), 4.59 (s, 2H). A further portion of title compound can be obtained from the mother liquor.

Example 39

1-(4-Chloroanilino)-4-(4-pyridylmethyl)phthalazine hemifumarate

A solution of 0.696 g (6 mmol) fumaric acid in 20 ml methanol is added to a hot solution of 1.04 g (3 mmol) 1-(4-chloroanilino)-4-(4-pyridylmethyl)phthalazine in 30 ml methanol. As it cools to 0° C., crystals precipitate out; these are filtered off and recrystallized again from methanol. Title compound is obtained after drying under HV (8 h at 100° C.); m.p. 202° C. (decomp.); ESI-MS: (M+H)$^+$=347.

Example 40

1-(4-Chloroanilino)-4-(4-pyridylmethyl)phthalazine dimesylate

A solution of 0.583 ml (9 mmol) methanesulfonic acid and, at about 30° C., ether are added to a hot solution of 1.56 g (4,5 mmol) 1-(4-chloroanilino)-4-(4-pyridylmethyl)phthalazine until slight turbidity occurs. As it cools to 0° C., crystals precipitate out; these are filtered off and recrystallized again from methanol. After drying under HV (8 h, 120° C.) and equilibration for 24 h at 20° C. and in room atmosphere, title compound is obtained with a water content of 3.97 %; m.p. 145–150° C.; $^1$H NMR (DMSO-$d_6$) 10.50–11.70 (br), 8.82–8.88 (m, 3H), 8.33–8.39 (m, 1 H), 8.18–8.29 (m, 2H), 7.98 (d, 2H), 7.58–7.70 (m, 4H), 4.94 (s, 2H), 2.32, (s, 6H); ESI-MS: (M+H)$^+$=347.

Example 41

1-(4-Chloroanilino)-4-(4-pyridylmethyl)phthalazine dihydrochloride

While stirring, 6.24 g (18 mmol) 1-(4-chloroanilino)-4-(4-pyridylmethyl)phthalazine is dissolved in 180 ml methanol at about 50° C. The solution is cooled to RT and mixed slowly with 3.15 ml (38.2 mmol) conc. (about 37%) hydrochloric acid. When 100 ml ether is added dropwise to the reaction mixture, a crystalline precipitate forms. The suspension thereof is stirred for 15 min at RT. A further 80 ml is added dropwise to the suspension, which is stirred for a further 15 min at 20° C. and then for 0.5 h under ice cooling. After filtration, washing of the filter residue with ether, drying under HV (5 h, 90° C.) and equilibration (room atmosphere, 24 h, 20° C.), title compound is obtained with a water content of 8.63%; m.p. 268–270° C.; $^1$H NMR (DMSO-d$_6$): Identical to Example 1 apart from high-field shift of signals by 0.03 ppm.

Example 42

1-(3-Chloro-4-fluoroanilino)-4-(4-pyridylmethyl) phthalazine

A mixture of 1.42 g (10 mmol) phosphorus pentoxide, 1.38 g (10 mmol) triethylamine hydrochloride, and 1.46 g (10 mmol) 3-chloro-4-fluoroaniline is heated and stirred in a nitrogen atmosphere at 200° C. until a homogeneous melt has formed. To the melt, 0.593 g (2.5 mmol) 4-(4-pyridylmethyl)-1(2H)-phthalazinone is added and the reaction mixture stirred for a further 3 h at 200° C. After cooling to RT, the hyalinocrystalline reaction mixture is distributed between 150 ml dichloromethane and a mixture of 10 ml water and 20 ml 2N sodium hydroxide solution with intensive stirring and sonication. The organic phase washed with water and dried over sodium sulfate is concentrated by evaporation and the residue recrystallized from acetate. Title compound is obtained after a second recrystallization from methanol/water and drying under HV (8 h at 100° C.); m.p. 185–187° C.; ESI-MS: (M+H)$^+$=365.

Example 43

1-(3-Methylanilino)-4-(4-pyridylmethyl)phthalazine

A mixture of 2.39 g (16,8 mmol) phosphorus pentoxide, 2.31 g (16,8 mmol) triethylamine hydrochloride, and 1.82 ml (16.8 mmol) m-toluidine is heated and stirred in a nitrogen atmosphere at 200° C. until a homogeneous melt has formed. To the melt, 1 g (4.2 mmol) 4-(4-pyridylmethyl)-1(2H)-phthalazinone is added and the reaction mixture stirred for a further 3.5 h at 205° C. After cooling to about 170° C., 4 ml tetramethylurea is added to the reaction mixture, followed by 2 ml water at about 110° C. The mixture is stirred for a further 30 min while cooling to RT and then distributed between dichloromethane and a mixture of 20 ml water and 5 ml conc. ammonia. The organic phase dried over sodium sulfate is concentrated by evaporation and the residue purified on silica gel by flash chromatography using acetate and acetate/methanol (99:1 and 19:1). Title compound is obtained after crystallization of the product-containing fractions from acetonitrile and subsequent recrystallization from acetate; m.p. 141–143° C.; ESI-MS: (M+H)$^+$=327.

Example 44

The following compounds are prepared in the same manner as one of the processes mentioned hereinbefore.

Example 44

A) 1-(4-Ethylanilino)-4-(4-pyridylmethyl)phthalazine; m.p. 163–164° C.; ESI-MS: (M+H)$^+$=341.
B) 1-(4-Propylanilino)-4-(4-pyridylmethyl)phthalazine; m.p. 180–181° C.; ESI-MS: (M+H)$^+$=355.
C) 1-(3-Fluoro-4-methylanilino)-4-(4-pyridylmethyl) phthalazine; m.p. 210–212° C.; ESI-MS: (M+H)$^+$=345.
D) 1-(4-Chloro-2-fluoroanilino)-4-(4-pyridylmethyl) phthalazine; m.p. 157–159° C.; ESI-MS: (M+H)$^+$=365.
E) 1-(4-Ethoxyanilino)-4-(4-pyridylmethyl)phthalazine; m.p. 223–224° C.; ESI-MS: (M+H)$^+$=357 (see Ex. 52).
F) 1-(4-Chloroanilino) 4-[(2-methyl-4-pyridyl)methyl] phthalazine; m.p. 158–159° C.; ESI-MS: (M+H)$^+$=361 (see Ex. 59).
G) 1-(4-Chloroanilino) 4-[(2,6-methyl-4-pyridyl)methyl] phthalazine; m.p. 175–176° C.; ESI-MS: (M+H)$^+$=375 (see Ex. 60).
H) 1-(4-Chloroanilino) 4-(4-pyridylmethyl)-5,6,7,8-tetrahydrophthalazine; m.p. 181–183° C.; ESI-MS: (M+H)$^+$=351 (see Ex. 51).

Example 45

1-(3,4-Dimethylanilino)-4-(4-pyridylmethyl) phthalazine

A mixture of 1.80 g (12.68 mmol) phosphorus pentoxide, 1.73 g (12.6 mmol) triethylamine hydrochloride, and 1.529 g (12.6 mmol) 3,4-dichloromethylaniline is heated and stirred in a nitrogen atmosphere at 200° C. until a homogeneous melt has formed. To the melt, 1 g (4.2 mmol) of 4-(4-pyridylmethyl)-1(2H)-phthalazinone (for preparation see German Auslegeschrift no. 1 061 788 [published 23.07.1959]) is added and the mixture stirred for 4 h at 200° C. After slight cooling, 4 ml tetramethylurea is added to the reaction mixture, followed by 2 ml water at about 120° C. The solution obtained is then distributed between dichloromethane and a mixture of 20 ml water and 5 ml conc. ammonia, and the organic phase dried over anhydrous sodium sulfate, filtered and evaporated under vacuum. Double recrystallization of the residue from acetonitrile and drying under HV (8 h, 120° C.) yields title compound; m.p. 180–181° C.; ESI-MS: (M+H)$^+$=341.

Example 46

1-(3,5-Dimethylanilino)-4-(4-pyridylmethyl) phthalazine

Preparation as described under Example 45, with 3,5-dimethylaniline instead of 3,4-dimethylaniline. Title compound: m.p. 174–175° C.; ESI-MS: (M+H)$^+$=341.

Example 47

1-(4-Isopropylanilino)-4-(4-pyridylmethyl) phthalazine dihydrochloride

In the manner described in Example 45, a mixture of 1.80 g (12.68 mmol) phosphorus pentoxide, 1.73 g (12.6 mmol) triethylamine hydrochloride, 1.8 ml (12.74 mmol) 4-isopropylaniline, and 1 g (4.2 mmol) 4-(4-pyridylmethyl)-1 (2H)-phthalazinone is stirred for 4 h at 210° C. The frozen melt is then suspended in water using an ultrasonic bath, filtered, and the filtrate evaporated in the RE. The oil-like residue is distributed between dichloromethane and a mixture of 20 ml water and 5 ml conc. ammonia, and the organic phase dried over anhydrous sodium sulfate, filtered and evaporated under vacuum. The residue is then stirred with acetonitrile, filtered off from some non-transformed 4-(4-pyridylmethyl)-1(2H)-phthalazinone, and the filtrate evaporated under vacuum. Flash chromatography of the residue on silica gel with a particle size of 0.04–0.06 mm using acetate/methanol mixtures (20:1 and 10:1) yields a resin (free base of the title compound), which is dissolved in a mixture of 4 ml methanol and 1.5 ml of 3 N methanolic HCl. After evaporation under vacuum, recrystallization of the residue from methanol/ether, drying under HV (8 h, 120°

C.), and equilibration for 16 h at 20° C. and in room atmosphere, title compound is obtained with a water content of 9.4%; m.p. >250° C.; ESI-MS: (M+H)$^+$=355.

Example 48

1-(4-tert-Butylanilino)-4-(4-pyridylmethyl) phthalazine dihydrochloride

In the manner described in Example 45, a mixture of 1.80 g (12.68 mmol) phosphorus pentoxide, 1.73 g (12.6 mmol) triethylamine hydrochloride, 1,9 ml (12.5 mmol) 4-tertbutylaniline, and 1 g (4.2 mmol) 4-(4-pyridylmethyl)-1(2H)-phthalazinone is stirred for 4.5 h at 210° C. The frozen melt is then dissolved in dichloromethane using an ultrasonic bath, filtered off from undissolved components, and the filtrate evaporated in the RE. The oil-like residue is distributed between dichloromethane and a mixture of 20 ml water and 5 ml conc. ammonia, and the organic phase dried over anhydrous sodium sulfate, filtered and evaporated under vacuum. The residue is then stirred with 10 ml acetonitrile, filtered off from some non-transformed 4-(4-pyridylmethyl)-1(2H)-phthalazinone, and the filtrate evaporated under vacuum. Flash chromatography of the residue on silica gel with a particle size of 0.04–0.06 mm using a toluene/acetone mixture (7:3) yields a resin (free base of the title compound), which is dissolved in a mixture of 4 ml methanol and 1.5 ml of 3 N methanolic HCl. After evaporation under vacuum, recrystallization of the residue from methanol/ether, drying under HV (6 h, 80° C.), and equilibration for 16 h at 20° C. and in room atmosphere, title compound is obtained with a water content of 4.47%; m.p. 196–200° C.; ESI-MS: (M+H)$^+$=369.

Example 49

1-(4-Chloroanilino)-4-(4-pyridylmethylamino) phthalazine

A mixture of 0.5 g (1.5436 mmol) 1-chloro-4-(4-chloroanilino)phthalazine hydrochloride (for preparation see J. Chem. Soc. 1948, 777–782) and 2 g (18.50 mmol) 4-aminomethylpyridine is stirred for 36 h at 90° C. and then purified by means of flash chromatography on silica gel with a particle size of 0.04–0.06 mm using acetate and acetate/methanol (20:1). Evaporation of product-containing fractions, recrystallization of the residue from methanol, and drying of the crystallizate under HV yield the title compound; m.p. 233–236° C.; ESI-MS: (M+H)$^+$=362.

Example 50

1-(4-Chloroanilino)-4-(4-pyridylmethoxy) phthalazine

A mixture of 1 g (9.16 mmol) 4-hydroxymethylpyridine, 0.44 g (11.0 mmol) sodium hydride (60% dispersion in oil) and 15 ml DMF is incubated for 20 min at 0° C. while stirring in a nitrogen atmosphere. At RT, 1 g (3.07 mmol) 1-chloro-4-(4-chloroanilino)phthalazine hydrochloride is added to the mixture, which is stirred for about 1 h at 500C and for 15 h at 80° C. Addition to the reaction mixture of a little water, evaporation under vacuum, recrystallization of the residue from methanol, and drying under HV yield the title compound with a water content of 3.36%; m.p. 139–141° C.; ESI-MS: (M+H)$^+$=363.

Example 51

1-(4-Chloroanilino) 4-(4-pyridylmethyl)-5,6,7,8-tetrahydrophthalazine

Preparation up to evaporation under vacuum as described under Example 45, but using 4-chloroaniline instead of 3,4-dimethylaniline. Further purification of the residue is then carried out by means of flash chromatography on silica gel with a particle size of 0.04–0.06 mm using acetate/methanol mixtures (40:1 and 20:1). Title compound is obtained after evaporation of the product-containing fractions under vacuum and recrystallization of the residue from acetonitrile; m.p. 181–183° C.; ESI-MS: (M+H)$^+$=351. The starting material is prepared as follows:

51.1) 2-[4(1H)-Pyridinylidene]-4,5,6,7-tetrahydro-inden-1,3-dione

Four portions each of 0.99 ml 5,4 M methanolic sodium methylate solution (21.4 mmol) are stirred into a solution of 2.957 g (21.4 mmol) 4,5,6,7-tetrahydro-1(3H)-isobenzofuranone (for preparation see J. Am. Chem. Soc. 118, 1–12 [1996]), 2.02 ml (21.4 mmol) pyridine-4-carbaldehyde, and 10.7 ml (93.2 mmol) ethyl propionate in 17.4 ml methanol at intervals of 5 min respectively and at 0° C. The reaction mixture is stirred for 20 min at RT, heated for 2 h under reflux, and then evaporated under vacuum. Stirring of the residue in 5 ml water, filtration, washing of the filter residue with water, and drying under HV (8 h, 100° C.) yields the title compound; m.p. 258–261° C.; ESI-MS: (M+H)$^+$=228. A further, slightly impure batch of title compound may be obtained by extracting the aqueous filtrate with diethylether, adjusting the aqueous phase to pH 7 with glacial acetic acid, filtering, and washing the filter residue with water.

51.2) 4-(4-Pyridylmethyl)-5,6,7,8-tetrahydro-1(2H)-phthalazinone

A mixture of 0.773 g (3.4 mmol) 2-[4(1H)-pyridinylidene]-4,5,6,7-tetrahydro-inden-1,3-dione and 5 ml hydrazine hydrate is heated for 4 h under reflux. The title compound is obtained after cooling to 0° C., filtration, washing of the filter residue with water, then ether, and drying under HV (8 h, 100° C.); m.p. 193–194° C.; ESI-MS: (M+H)$^+$=242.

Example 52

1-(4-Ethoxyanilino)-4-(4-pyridylmethyl)phthalazine

A mixture of 0.3 g (1.173 mmol) 1-chloro-4-(4-pyridylmethyl)phthalazine (for preparation see German Auslegeschrft no. 1 061 788 [published 23.07.1959]), and 0.483 g (3.52 mmol) 4-ethoxyaniline is heated for 30 min at 90° C. The cooled reaction mixture is distributed with thorough stirring between a dichloromethane/methanol mixture (18:1) and saturated aqueous sodium carbonate solution. The organic phase washed with water and brine is dried over anhydrous sodium sulfate and evaporated under vacuum. Title compound is obtained after recrystallization of the residue from acetate/methanol and acetonitrile; m.p. 223–224° C.; ESI-MS: (M+H)$^+$=357.

Example 53

1-(4-Phenylanilino)-4-(4-pyridylmethyl)phthalazine

A mixture of 2.41 g (16.98 mmol) phosphorus pentoxide, 2.32 g (16.85 mmol) triethylamine hydrochloride, 3 g (17.73 mmol) 4-aminobiphenyl, and 1 g (4.21 mmol) 4-(4-pyridylmethyl)-1(2H)-phthalazinone is stirred for 20 h at 200° C. under a nitrogen atmosphere. After cooling to RT, the hyalinocrystalline melt is distributed between a dichloromethane/methanol mixture (99:1) and a mixture of water and saturated aqueous carbonate solution (1:1) with intensive stirring and the use of an ultrasonic bath. The organic phase dried over sodium sulfate is evaporated under vacuum and the residue purified by means of flash chromatography on silica gel with particle size 0.04–0.06 mm, using a dichloromethane/methanol mixture (49:1). Title compound is obtained after evaporation of the product-containing fractions under vacuum and recrystallization of the residue from acetonitrile; m.p. 189–191° C.; ESI-MS: (M+H)$^+$=389.

Example 54

1-(3,4,5-Trimethoxyanilino)-4-(4-pyridylmethyl) phthalazine

A mixture of 0.3 g (1.173 mmol) 1-chloro-4-(4-pyridylmethyl)phthalazine (for preparation see German Auslegeschrift no. 1 061 788 [published 23.07.1959]), and 0.645 g (3.52 mmol) 3,4,5-trimethethoxyaniline is heated for 1 h at 110° C. The cooled reaction mixture is distributed with thorough stirring between a dichloromethane/methanol mixture (20:1) and saturated aqueous sodium carbonate solution. The organic phase washed with water and brine is dried over anhydrous sodium sulfate, evaporated under vacuum, and the residue purified by means of flash chromatography on silica gel with particle size 0.04–0.06 mm, using an acetate/methanol mixture (19:1). Title compound is obtained after evaporation of the product-containing fractions under vacuum and recrystallization of the residue from dichloromethane/hexane; m.p. 110–111° C.; ESI-MS: (M+H)$^+$=403.

Example 55

1-(4-Chloroanilino)-4-(4-pyridylmethyl)phthalazine-3-oxide

A mixture of 1.53 g (4.41 mmol) 1-(4-chloroanilino)-4-(4-pyridylmethyl)phthalazine (see Example 4), 1.74 g (about 5.75 mmol) 3-chloroperbenzoic acid (about 57%), and 80 ml acetate is stirred for 1 h at RT. Then 25 ml 1 N aqueous sodium hydrogencarbonate solution is added to the reaction mixture, which is stirred for 10 min, filtered, washed with water, then acetate, and the filter residue purified by means of flash chromatography on silica gel with particle size 0.04–0.06 mm, using an acetate/methanol mixture (19:1). Title compound is obtained after evaporation of the product-containing fractions under vacuum and recrystallization of the filter residue from methanol; m.p. 226–228° C.; ESI-MS: (M+H)$^+$=363.

Example 56

1-(3-Hydroxyphenoxy)-4-(4-pyridylmethyl) phthalazine

A solution of 0.2 g (1.82 mmol) resorcinol in 5 ml dioxane is spiked with 0.37 ml 5.4 M methanolic sodium methylate solution (2 mmol) The crystalline residue is then suspended in 5 ml dioxane, 0.511 g (2 mmol) 1-chloro-4-(4-pyridylmethyl)phthalazine is added, and the reaction mixture stirred under nitrogen atmosphere for 18 h at 120° C. After cooling to RT and filtration, the filtrate is evaporated under vacuum, and the residue purified by means of flash chromatography on silica gel with particle size 0.04–0.06 mm, using acetate and ethyl acetate/methanol mixtures (50:1 and 25:1). The product-containing fractions are evaporated under vacuum, the crystalline residue suspended in about 5 ml dichloromethane, and filtered. Title compound is obtained after drying of the crystallizate under HV (6 h, 100° C.); m.p. 206–207° C.; ESI-MS: (M+H)$^+$=330.

Example 57

1-Cyclohexylamino-4-(4-pyridylmethyl)phthalazine

A mixture of 0.3 g (1.173 mmol) 1-chloro-4-(4-pyridylmethyl)phthalazine and 0.523 g (5.278 mmol) cyclohexylamine is stirred for 8 h at 11 5° C. The cooled reaction mixture is then distributed between dichloromethane and saturated aqueous sodium hydrogencarbonate solution. The organic solution washed with brine and dried over anhydrous sodium sulfate is evaporated and the residue purified on silica gel by flash chromatography using acetate/methanol (19:1). Title compound (with water content of 0.56%) is obtained after crystallization of the product-containing fractions from acetonitrile and drying under HV; m.p. 137–139° C.; ESI-MS: (M+H)$^+$=319.

Example 58

1-Cyclopentylamino-4-(4-pyridylmethyl)phthalazine

A mixture of 0.3 g (1.173 mmol) 1-chloro-4-(4-pyridylmethyl)phthalazine and 0.4 g (4.692 mmol) cyclopentylamine is stirred for 6 h at 115° C. The cooled reaction mixture is then distributed between dichloromethane and saturated aqueous sodium hydrogencarbonate solution. The organic solution washed with brine and dried over anhydrous sodium sulfate is evaporated and the residue purified on silica gel by flash chromatography using acetate/methanol (9:1). Title compound is obtained after crystallization of the product-containing fractions from acetonitrile/water and drying under HV (8 h, 100° C.); m.p. 163–165° C.; ESI-MS: (M+H)$^+$=305.

Example 59

1-(4-Chloroanilino) 4-[(2-methyl-4-pyridyl)methyl] phthalazine

A mixture of 910 mg (6.36 mmol) phosphorus pentoxide, 876 mg (6.36 mmol) triethylamine hydrochloride, and 812 mg (6.36 mmol) 4-chloroaniline is heated at 200° C. until a homogeneous melt has formed. To the melt, 400 g (1.59 mmol) 4-[(2-methyl-pyridin-4-yl)-methyl]-1(2H)-phthalazinone is added and the reaction mixture stirred for a further 16 h at 200° C. The cooled reaction mixture is distributed with thorough stirring and use of an ultrasonic bath between a dichloromethane/methanol mixture (about 20:1) and saturated aqueous sodium carbonate solution. The organic phase washed with water and brine is dried over anhydrous sodium sulfate, evaporated under vacuum, and the residue purified by means of flash chromatography on silica gel with particle size 0.04–0.06 mm, using an acetate/methanol mixture (19:1). Title compound is obtained after evaporation of the product-containing fractions under vacuum and crystallization of the residue from acetonitrile; m.p. 158–159° C.; ESI-MS: (M+H)$^+$=361. The starting material is prepared as follows:

59.1) 2-[2-Methyl-1.H.-pyridin-4-ylidene]-indan-1,3-dione

A mixture of 27.7 g (0.187 mol) phthalic acid anhydride and 20.04 g (0.187 mol) 2,4-dimethylpyridine is heated for 20 h at 180° C. in a nitrogen atmosphere with stirring. The reaction mixture is then suspended in 250 ml ethanol at about 75° C. using an ultrasonic bath. The suspension is filtered, the filtrate evaporated under vacuum, and the residue purified by means of flash chromatography on silica gel with particle size 0.04–0.06 mm, using acetate/methanol mixtures (49:1 and 19:1). The product-containing fractions are evaporated under vacuum, the residue heated in a methanol/dichloromethane mixture (3:1) and then cooled in an ice bath. Fitration and drying of the filter residue under HV (8 h, 100° C.) yields title compound; m.p. >260° C.; ESI-MS: (M+H)$^+$=238.

59.2) 4-[2-Methyl-1.H.-pyridin-4-yliden]-1(2H)-phthalazinone

A mixture of 5.5 g (23.18 mmol) 2-[2-methyl-1.H.-pyridin-4-ylidene]-indan-1,3-dione and 21.8 ml hydrazine hydrate is heated for 4 h at 130° C. under a nitrogen atmosphere. Then 50 ml ethanol is added to the reaction mixture, which is cooled to RT, filtered, and the filter residue washed with ethanol and ether. Title compound is obtained after drying under HV; m.p. 183–184° C.; ESI-MS: (M+H)$^+$=252.

Example 60

1-(4-Chloroanilino) 4-[(2,6-dimethyl-4-pyridyl)methyl]phthalazine

Title compound is obtained using the method described under Example 59, but with 4-[(2,6-dimethyl-pyridin-4-ylyl)methyl]-1(2H)-phthalazinone instead of 4-[(2-methyl-pyridin-4-yl)-methyl]-1(2H)-phthalazinone; m.p. 175–176° C.; ESI-MS: (M+H)$^+$=375. The starting material is prepared as follows:

60.1) 2-[2,6-Dimethyl-1.H.-pyridin-4-ylidene]-indan-1,3-dione

Title compound is obtained using the method described under Example 59.1, but with 2,4,6-trimethylpyridine instead of 2,4-dimethylpyridine; m.p. >250° C.; ESI-MS: (M+H)$^+$=252.

60.2) 4-[(2,6-Dimethyl-pyridin-4-yl)methyl]-1(2H)-phthalazinone

Using the method described under Example 59.2, title compound is obtained starting from 2-[2,6-dimethyl-1.H.-pyridin-4-ylidene]-indan-1,3-dione and hydrazine hydrate; m.p. 229–230° C.; ESI-MS: (M+H)$^+$=266.

Example 61

1-Cyclopropylamino-4-(4-pyridylmethyl)phthalazine, 1.58 hydrochloride

A mixture of 0.3 g (1.173 mmol) 1-chloro-4-(4-pyridylmethyl)phthalazine and 1.4 ml (14.076 mmol) cyclopropylamine is stirred for 8 h at 110° C. The cooled reaction mixture is then distributed between dichloromethane and saturated aqueous sodium hydrogencarbonate solution. The organic solution washed with brine and dried over anhydrous sodium sulfate is evaporated and the residue purified on silica gel by flash chromatography using acetate/methanol (9:1). The product-containing fractions are evaporated under vacuum, and the residue is stirred with 1 ml 3N methanolic HCl. The crystallizate obtained is filtered off with a little methanol and washed with ether. After drying under HV (8 h, 160° C.), title compound is obtained with a water content of 8.63%; m.p. >250° C.; ESI-MS: (M+H)$^+$=277.

Example 62

1-(4-Chloroanilino)-4-(4-pyridylmethyl)phthalazine succinate

A solution of 1.77 g (15 mmol) succinic acid in 35 ml ethanol is added to a hot solution of 5.0 g (14.4 mmol) 1-(4-chloroanilino)-4-(4-pyridylmethyl)phthalazine in 150 ml ethanol. As the mixture cools (scraping) to 0° C., a crystalline precipitate slowly forms, which is filtered off, washed with ethanol, and dried: Anal. calc.($C_{24}H_{21}N_4ClO_4$) C, 62.00%; H, 4.55%; N, 12.05%; found C, 62.02%; H, 4.75%; N, 12.04%.

Example 63

1-(4-Chloroanilino)-4-(4-pyridylmethyl)phthalazine oxalate

A solution of 1.35 g (15 mmol) oxalic acid in 35 ml ethanol is added to a hot solution of 5.0 g (14.4 mmol) 1-(4-chloroanilino)-4-(4-pyridylmethyl)phthalazine in 150 ml ethanol. On stirring, crystals precipitate out. Cooling, filtering, washing with ethanol, and drying yield the title compound: Anal. calc.($C_{22}H_{17}N_4ClO_4$) C, 60.49%; H, 3.92%; N, 12.83%; found C, 60.69%; H, 4.05%; N, 12.97%.

Example 64 rac 1-(4-Chloroanilino) 4-[1-(4-pyridyl)ethyl]phthalazine

A mixture of 300 mg (1.19 mmol) rac4-[1-(4-pyridyl)ethyl]-1(2H)-phthalazinone, 683 mg (4.77 mmol) phosphorus pentoxide, 657 mg (4.77 mmol) triethylamine hydrochloride, and 609 mg (4.77 mmol) 4-chloroaniline is heated for 8 h to 205° C. The brown solution is taken up in dichloromethane/methanol 19:1, washed successively with sat. $Na_2CO_3$ solution, 3× with water and brine, and the organic phase ($Na_2O_4$) is washed and concentrated by evaporation. Chromatography ($SiO_2$; ethyl acetate/$CH_3OH$, 19:1) yields the title compound: m.p.: 132–134° C.; Anal. calc.($C_{21}H_{17}N_4Cl.½CH_3OH$) C, 68.52%; H, 5.08%; N, 14.87%; found C, 68.4%; H, 5.0%; N, 14.9%. The starting material is prepared as follows:

64.1) 3-(1-Pyridin-4-yl-ethylidene)-3-.H.-isobenzofuran-1-one 25.0 g (168.9 mmol) phthalic acid anhydride, 11.8 g (77.9 mmol) 3-pyridin-4-yl-propionic acid [for preparation, see: J. Med. Chem. 39, 609 (1996)], 1.065 g (13 mmol) sodium acetate and 40 ml dimethylacetamide are stirred for 4 h at 180° C. The reaction mixture is then poured onto a mixture of ice and 250 ml 0.2 N sodium hydroxide solution, stirred, and extracted twice with ethyl acetate. The organic phases are washed with water and brine, dried ($Na_2O_4$) and concentrated by evaporation. Chromatography ($SiO_2$; ethyl acetate/$CH_3OH$, 19:1) and crystallization from ethanol yield the title compound: FAB MS (M+H)$^+$=238.

64.2)) rac 4-[1-(4-Pyridyl)ethyl]-1(2H)-phthalazinone

In 50 ml ethanol, 2.2 g (9.27 mmol) 3-(1-pyridin-4-yl-ethylidene)-3-.H.-isobenzofuran-1-one and 597 ml (12 mmol) hydrazine hydrate are boiled for 4.5 h under reflux. A white solid settles out, which is filtered off and discarded. The filtrate is concentrated by evaporation and title compound crystallized out from acetonitrile. m.p.: 201–203° C.;

Anal. calc. ($C_{15}H_{13}N_3O$·0.15 $H_2O$) C, 70.93%; H, 5.28%; N, 16.54%; found C, 70.8%; H, 5.2%; N, 16.8%.

Example 65

1-(4-Chloroanilino) 4-[(1-oxypyridin-4-yl)methyl] phthalazine

To a solution of 437.7 mg (3.407 mmol) 4-chloroaniline in 25 ml ethanol, 1.25 g (≈80%; 3.245 mmol) 1-chloro-4-[(1-oxypyridin-4-yl)methyl]phthalazine hydrochloride is added and heated for 2 h to reflux temperature. The suspension is filtered and washed with ethanol. The resulting crude product contains ≈6–7% 1-(4-chloroanilino)-4-(4-pyridylmethyl)phthalazine as by-product. Chromatography ($SiO_2$; acetate/$CH_2Cl_2$/$CH_3OH$/$NH_3$ 70:15:15:1) and crystallization from acetate yield the title compound: m.p.: 249–251° C.; $^1$H-NMR (DMSO-$d_6$) 9.27 (s, 1H), 8.59 (d, 1H), 8.14 (d, 1H), 8.10 (d, 2H), 7.99 (m, 3H), 7.95 (m, 1H), 7.39 (d, 2H), 7.33 (d, 2H), 4.55 (s, 2H); FAB MS (M+H)$^+$=363. The starting material is prepared as follows:

65.1) 4-[(1-Oxypyridin-4-yl)methyl]-1(2H)-phthalazinone

To an ice-cooled solution of 5.0 g (21.07 mmol) 4-(4-pyridylmethyl)-1(2H)-phthalazinone [for preparation, see German Auslegeschrift no. 1061788 (published 23.7.1959)] in 30 ml acetic acid, 14 ml peracetic acid (Fluka, Buchs/Switzerland; 32% in acetic acid) is added and stirred for 52 h at RT. The reaction solution is concentrated by evaporation, the residue suspended in 15 ml water and neutralized with sat. $NaHCO_3$ solution. Filtration and washing with water leads to title compound, which still comprises about 20% 4-(4-pyridylmethyl)-1(2H)-phthalazinone. This crude product is used for the next stage. Chromatography ($SiO_2$; $CH_2Cl_2$/$CH_3OH$, 9:1) yields pure title compound: m.p.: 274–275° C.; FAB MS (M+H)$^+$=254.

65.2)) 1-Chloro-4-[(1-oxypyridin-4-yl)methyl] phthalazine hydrochloride

A suspension of 4.45 g (17.6 mmol) 4-[(1-oxypyridin-4-yl)-methyl]-1(2H)-phthalazinone in 65 ml acetonitrile is mixed with 8.8 ml (35.2 mmol) 4N HCl solution in dioxane and finally with 4.17 ml (45.7 mmol) phosphoryl chloride. After stirring for 30 h at 45° C., the red suspension is filtered and washed with acetonitrile: FAB MS (M+H)$^+$=272.

Example 66

1-(4-Chloroanilino)-4-(4-pyrimidinylmethyl) phthalazine

A mixture of 100 mg (0.45 mmol) 1-chloro-4-(4-pyrimidinylmethyl)phthalazine hydrochloride and 149 mg (1.17 mmol) 4-chloroaniline is heated for 1.5 h to 100° C. The reaction mixture is distributed between dichloromethane/$CH_3OH$, 19:1 and sat. $NaHCO_3$ solution. The organic phase is separated off, washed with water and brine, dried ($Na_2SO_4$), and concentrated by evaporation. Chromatography ($SiO_2$; ethyl acetate/$CH_3OH$, 19:1) and crystallization from ethyl acetate/ether yield the title compound: m.p.: 174–176° C.; FAB MS (M+H)$^+$=348. The starting material is prepared as follows:

66.1) 2-Pyrimidin-4-yl-indan-1,3-dione 7.87 g (53.1 mmol) phthalic acid anhydride and 22 ml (0.24 mol) 4-methylpyrimidine are stirred for 1 h at 140° C. and for 4 h at 210° C. The reaction mixture is then stirred with 15 ml methanol, filtered, and the residue washed with methanol. Further product is obtainable by evaporating the filtrate and stirring the residue with water m.p.: 168–169° C.); Anal. calc.($C_{13}H_8N_2O_2$) C, 69.64%; H, 3.60%; N, 12.49%; found C, 69.8%; H 3.7%; N, 12.4%; FAB MS (M+H)$^+$=225.

66.2) 4-(4-Pyrimidinylmethyl)-1(2H)-phthalazinone 1.20 g (5.35 mmol) 2-pyrimidin-4-yl-indan-1,3-dione in 30 ml ethanol is spiked with 345 μl (6.96 mmol) hydrazine hydrate and heated for 5 h to 100° C. After cooling, the product is filtered off and washed with ethanol: m.p.: 204–206° C.; Anal. calc.($C_{13}H_{10}N_4O$·0.5 $H_2O$) C, 63.15%; H, 4.48%; N, 22.66%; found C, 63.3%; H, 4.5%; N, 22.7%; FAB MS (M+H)$^+$=239.

66.3) 1-Chloro-4-(4-pyrimidinylmethyl)phthalazine hydrochloride 850 mg (3.57 mmol) 4-(4-pyrimidinylmethyl)-1(2H)-phthalazinone in 15 ml acetonitrile is mixed with 1.78 ml (7.14 mmol) 4N HCl solution in dioxane and finally with 1.14 ml (12.5 mmol) phosphoryl chloride. After stirring for 36 h at 50° C., the red suspension is filtered and washed with acetonitrile: FAB MS (M–H)$^+$=255. Further product is obtainable from the evaporated filtrate by distribution between dichloromethane and sat. $NaHCO_3$ solution.

Example 67

A: 1-(3-Phenoxyanilino)-4-(4-pyridylmethyl) phthalazine

A mixture of 256 mg (1.00 mmol) 1-chloro-4-(4-pyridylmethyl)phthalazine and 556 mg (3.00 mmol) 4-phenoxyaniline (Aldrich) is heated for 2 h at 90° C. The melt is cooled and stirred with 6 ml $NH_3$ solution (10% in water: or 10 ml sat. $NaHCO_3$ solution) and 15 ml dichloromethane/methanol 50:1 for 30 min. The aqueous phase is then separated off and extracted again with dichloromethane. The organic phase is dried ($Na_2SO_4$), concentrated by evaporation, and chromatographed ($SiO_2$; ethyl acetate→ethyl acetate/$CH_3OH$, 19:1→10:1). Crystallization from acetonitrile yields the title compound: m.p.: 186–189° C.; Anal. calc. ($C_{26}H_{21}N_4O$) C, 77.02%; H, 5.22%; N, 13.82%; found C, 77.2%; H, 4.9%; N, 13.8%. The starting material is prepared as follows:

67.A1) 1-Chloro-4-(4-pyridylmethyl)phthalazine

Under exclusion of air, 29 g (122 mmol) 4-(4-pyridylmethyl)-1(2H)-phthalazinone [for preparation, see German Auslegeschrift no. 1061788 (published 23.7.1959)] in 450 ml acetonitrile is mixed with 61 ml HCl/dioxane 4N and 28 ml (306 mmol) phosphoryl chloride and stirred for 27 h at 50° C. To the white suspension, 119 g $NaHCO_3$ in 1.45 l water is then added dropwise under ice cooling, and the mixture is stirred and the title compound filtered off. Anal. calc.($C_{14}H_{10}N_3Cl$) C, 65.76%; H, 3.94%; N, 16.43%; Cl 13.86%; found C, 65.40%; H, 4.12%; N, 16.45%; Cl, 13.66%; FAB MS (M+H)$^+$=256.

In the same manner, the following compounds are prepared by reaction in the melt:

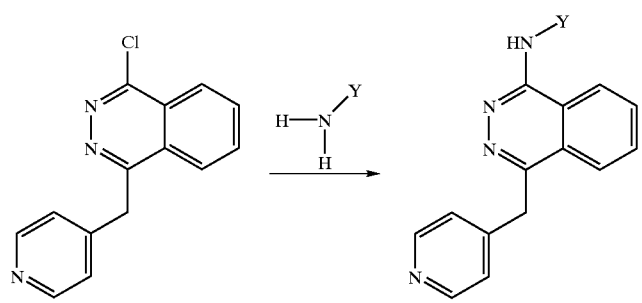
| Example | H₂N—Y | —HN—R | m.p. [°C.] | Anal.[1] | FAB-MS (M + H)⁺ |
|---|---|---|---|---|---|
| 67B | 2, 3-amino-2-methylphenol (H₂N-Ar-OH, Me) | HN-Ar-OH, Me | 192–195 | CHN (1.5 H₂O) | 343 |
| 67C | 3, 5-amino-2-methoxyphenol | HN-Ar(OMe)-OH | 256–258 | CHN (0.23 H₂O) | 359 |
| 67D | 2, 3-(methylthio)aniline | HN-Ar-SMe | 148–149 | CHN | 359 |
| 67E | 2, 3-ethylaniline | HN-Ar-Et | 143–144 | CHN | 341 |
| 67F | 2, 3-ethoxyaniline | HN-Ar-OEt | 193–195 | CHN | 357 |
| 67G | 2, 3-(trifluoromethyl)aniline | HN-Ar-CF₃ | 184–185 | CHN | 381 |
| 67H | 4, 3-(trifluoromethoxy)aniline | HN-Ar-OCF₃ | 176–178 | CHN | 397 |
| 67I | 3-bromoaniline | HN-Ar-Br | | | 391/393 |

-continued

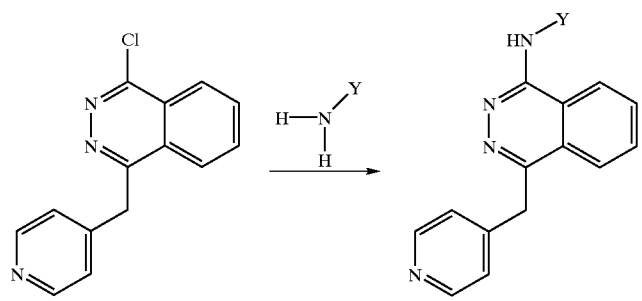

| Example | H₂N—Y | —HN⟨R | m.p. [° C.] | Anal.¹ | FAB-MS (M + H)⁺ |
|---|---|---|---|---|---|
| 67J | 3-aminobenzyl alcohol (2) | 3-(methylamino)benzyl alcohol | 192–193 | CHN | 343 |
| 67K | 1-(3-aminophenyl)ethanol (5) | 1-(3-(methylamino)phenyl)ethanol | 221–222 | CHN | 357 |
| 67L | 3-isopropoxyaniline (6) | 3-isopropoxy-N-methylaniline | 188–190 | CHN | 371 |
| 67M | 3-methoxy-5-(trifluoromethyl)aniline (5) | 3-methoxy-N-methyl-5-(trifluoromethyl)aniline | 143–145 | CHN | 411 |
| 67N | 3,5-dimethoxyaniline (2) | 3,5-dimethoxy-N-methylaniline | 193–196 | CHN | 373 |
| 67O | 3-tert-butylaniline (7) | 3-tert-butyl-N-methylaniline |  | CHN (0.5 H₂O) | 369 |

-continued

| Example | H₂N—Y | R (number) | —HN-R | m.p. [° C.] | Anal.[1] | FAB-MS (M + H)⁺ |
|---|---|---|---|---|---|---|
| 67P | 3-bromo-5-(trifluoromethyl)aniline | 4 | N-methyl-3-bromo-5-(trifluoromethyl)aniline | 223–226 | CHN | 459/461 |
| 67Q | 3-isopropylaniline | 6 | N-methyl-3-isopropylaniline | — | CHN (0.5 H₂O) | 355 |
| 67R | 3-fluoro-5-(trifluoromethyl)aniline | 4 | N-methyl-3-fluoro-5-(trifluoromethyl)aniline | 253–255 | CHN | 399 |
| 67S | 3-(1,1,2,2-tetrafluoroethoxy)aniline | 5 | N-methyl-3-(1,1,2,2-tetrafluoroethoxy)aniline | 185–187 | CHN F (0.3 H₂O) | 429 |
| 67T | 2,5-dimethoxyaniline | 2 | N-methyl-2,5-dimethoxyaniline | 199–201 | CHN | 373 |

[1]Deviation ≤ 0.4%;
manufacturer: [2]Fluka;
[3]Lancaster;
[4]JRD Fluorochemicals;
[5]Aldrich;
[6]TCI;
[7]Maybridge.

Example 68

A: 1-(3-Decyloxyanilino)-4-(4-pyridylmethyl)phthalazine

To 262 mg (1.05 mmol) decyloxyaniline (Salor) in 5 ml ethanol, 0.26 ml HCl/dioxane 4N is added, the mixture stirred for ≈3 min, and then 256 mg (1.00 mmol) 1-chloro-4-(4-pyridyl-methyl)phthalazine (Example 67A.1) is added. After 2 h boiling under reflux, the mixture is cooled and concentrated by evaporation. The residue is stirred with 6 ml NH₃ solution (10% in water: or 10 ml sat. NaHCO₃ solution)

and 15 ml dichloromethane/methanol 50:1 for 30 min. The aqueous phase is then separated off and extracted again with dichloromethane. The organic phase is dried (Na$_2$SO$_4$) and concentrated by evaporation. Crystallization [possibly after chromatography on SiO$_2$ (ethyl acetate/CH$_3$OH, 19:1)] from acetonitrile (or methanol) yields the title compound: m.p.: 116–119° C.; Anal. calc.(C$_{30}$H$_{36}$N$_4$O) C, 76.89%; H, 7.74%; N, 11.96%; found C, 76.7%; H, 7.7%; N, 11.9%; FAB MS (M+H)$^+$=469.

By the same manner, the following compounds are prepared in ethanol while heating:

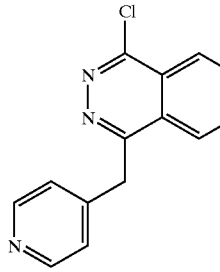

| Example | H$_2$N—Y | 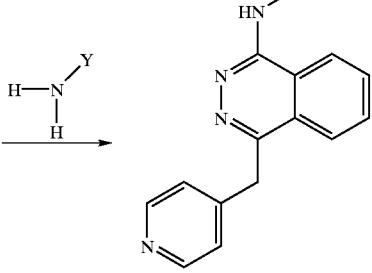 HN—R | m.p. [° C.] | Anal.[1] | FAB MS (M + H)$^+$ |
|---|---|---|---|---|---|
| 68B | 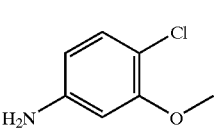 | 2 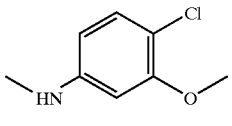 | 242–243 | CHN | 377 |
| 68C | 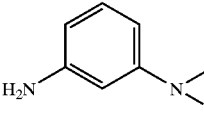 | 3,8 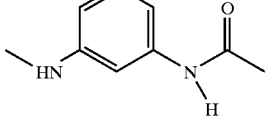 | 143–145 | CHN | 356 |
| 68D | 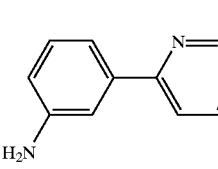 | 9 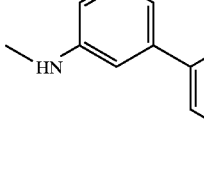 | 263–265 | CHN (0.22 H$_2$O) | 370 |
| 68E | 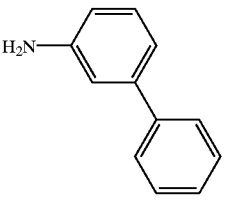 | 4,10 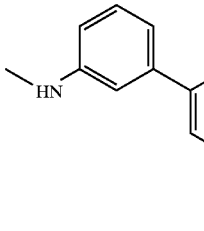 | 214–216 | CHN (0.13 H$_2$O) | 405 |
| 68F | 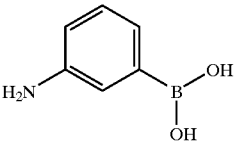 | 4,11 | | CHN (0.4 CH$_3$CN) | 389 |
| 68G | | 4,5,12,16 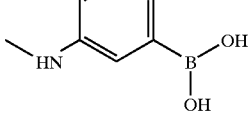 | | CHN (0.5 H$_2$O) | 357 |

-continued
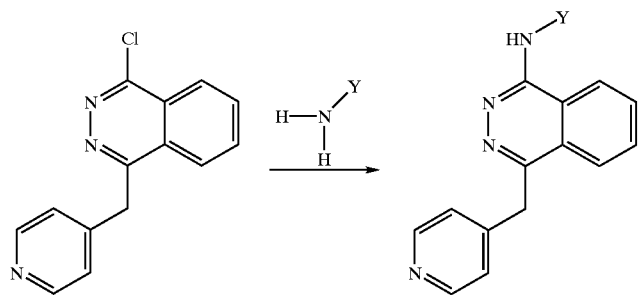
| Example | H₂N—Y | | HN(Me)R | m.p. [°C.] | Anal.[1] | FAB MS (M + H)⁺ |
|---|---|---|---|---|---|---|
| 68H | ethyl 3-aminobenzoate | 4,6,12 | ethyl 3-(methylamino)benzoate | 153–155 | CHN | 385 |
| 68I | 4-amino-3-methylphenol | 4,6,8 | 3-methyl-4-(methylamino)phenol | | | 343 |
| 68J | 3-(methylsulfonyl)aniline | 5,13 | N-methyl-3-(methylsulfonyl)aniline | 239–241 | CHN (0.2 H₂O) | 391 |
| 68K | 3-(phenylsulfonyl)aniline | 14 | N-methyl-3-(phenylsulfonyl)aniline | 196–199 | CHNS (0.26 H₂O) | 453 |
| 68L | 3-(pentyloxy)aniline | 7,14 | N-methyl-3-(pentyloxy)aniline | | CHNCl (1.6 H₂O) | 399 |

-continued

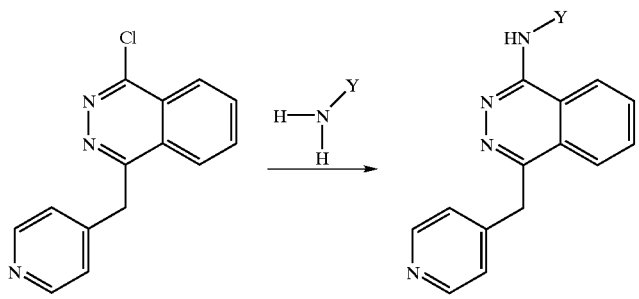

| Example | H₂N—Y | R (on HN) | m.p. [° C.] | Anal.[1] | FAB MS (M + H)⁺ |
|---|---|---|---|---|---|
| 68M | (3-oxazol-5-yl-aniline) [10] | | 194–196 | CHN (0.2 H₂O) | 380 |
| 68N | (4-chloro-3-trifluoromethyl-aniline) [8] | | 220–222 | CHNF | 415 |
| 68O | (4-fluoro-3-methoxy-aniline) [15] | | 190–192 | CHNF | 361 |
| 68P | (4-isopropyl-3-methyl-aniline) [7] | | 163–166 | CHN | 369 |

[1]Deviation ≤ 0.4%;
[2]prepared by hydrogenation (Raney-Nickel; EtOH/THF) of 4-chloro-3-methoxynitrobenzene (Riedel de Haen);
[3]addition of 2 eq HCl/dioxane;
[4]without addition of HCl/dioxane;
[5]reaction mixture concentrated by evaporation is taken up in water/CH₂Cl₂, addition of NH₃(aq) leads to crystallization of title compound;
[6]n-butanol as solvent, 120° C.;
[7]isolated as hydrochloride.
Manufacturers:
[8]Fluka;
[9]Bayer;
[10]Maybridge;
[11]TCI;
[12]Aldrich;
[13]Acros;
[14]Salor;
[15]Butt Park;
[16]Hemisulfate derivative.

Example 69

A: 1-[(4-Acetyl-3-hydroxyanilino)-4-(4-pyridylmethyl)phthalazine

302 mg (2.0 mmol) 2-acetyl-5-aminophenol (Maybridge) and 256 mg (1.00 mmol) 1-chloro-4-(4-pyridylmethyl)phthalazine (Example 67A.1) in 2 ml DMEU are heated for 3–18 h to 100° C. The reaction mixture is stirred with 10 ml NH₃ solution (10% in water) and 25 ml ethyl actetate (or dichloromethane) and filtered via Celite. The organic phase of the filtrate is dried (Na₂SO₄), evaporated, and chromatographed (SiO₂; ethyl acetate/CH₃OH, 40:1→10:1) Crystallization from acetonitrile yields the title compound: m.p.: 234–236° C.; HPLC: $t_{Ret}(Grad_{5-40})$=9.5; FAB MS $(M+H)^+$= 371.

In the same manner (with DMEU while heating), the following compounds are prepared:

3-methoxyanilino)-4-(4-pyridylmethyl)phthalazine (Example 68B) in 4 ml dichloromethane at 0° C. under a nitrogen atmosphere. The resinous mixture is left to stand for 18 h at RT, the dichloromethane phase is then decanted, and the glutinous residue stirred with 10 ml THF and 5 ml

| Example | $H_2N$—Y | —HN$^{Y}$ | m.p. [° C.] | Anal.[1] | FAB MS $(M + H)^+$ |
|---|---|---|---|---|---|
| 69B | (3-aminobenzamide) | [3] | 266–268 | 7.1[2] | 356 |
| 69C | (aminobenzodioxole) | [4] | 186–188 | CHN (0.7 $H_2O$) | 357 |

[1]Deviation ≦ 0.4%;
[2]HPLC: $t_{Ret}(Grad_{5-40})$.
Manufacturers:
[3]Aldrich;
[4]Fluka.

Example 70

1-(3-Acetylanilino)-4-(4-pyridylmethyl)phthalazine (A) and 1-[(2'-methyl-1',3'-dioxolan-2'-yl)-anilino]-4-(4-pyridylmethyl)phthalazine (B)

A mixture of 256 mg (1.00 mmol) 1-chloro-4-(4-pyridylmethyl)phthalazine (Example 67A.1) and 537 mg (3.00 mmol) 3-(2'-methyl-1',3'-dioxolan-2'-yl)-aniline (A. Bader Chem.) is stirred for 2 h at 90° C. The melt is cooled and stirred with 10 ml 20% $K_2CO_3$ solution and 30 ml dichloromethane. The aqueous phase is then separated off and extracted again with dichloromethane. The organic phase is dried ($Na_2SO_4$), concentrated by evaporation, and chromatographed on silica gel ($SiO_2$; acetate→acetate/$CH_3OH$, 100:1→4 19:1). Fractionated crystallization of the evaporated product fractions from 4 ml acetonitrile yields first A: m.p.: 229–231° C.; HPLC: $t_{Ret}(Grad_{5-40})$=8.2; FAB MS $(M+H)^+$=355. Cooling of the first mother liquor in an ice bath leads to crystallization of B: HPLC: $t_{Ret}(Grad_{5-40})$=9.3; FAB MS $(M+H)^+$=399.

Example 71

1-(4-Cloro-3-hydroxyanilino)-4-(4-pyridylmethyl) phthalazine

A solution of 2 ml boron tribromide (≈1 M in $CH_2Cl_2$) is mixed with a suspension of 0.19 g (0.50 mmol) 1-(4-chlorosat. $NaHCO_3$ solution. The resulting suspension is filtered, the filter residue washed with THF and discarded. The THF phase is separated and dried ($Na_2SO_4$), concentrated by evaporation, chromatographed ($SiO_2$; acetate/$CH_3OH$, 40:1→19:1) and title compound crystallized from acetonitrile/methanol: m.p.: 245–246° C.; HPLC: $t_{Ret}$ $(Grad_{5-40})$=8.8; FAB MS $(M+H)^+$=363.

Example 72

A: 1-(3-Chlorophenoxy)-4-(4-pyridylmethyl) phthalazine

Under exclusion of air, 200 mg (0.78 mmol) 1-chloro-4-(4-pyridylmethyl)phthalazine (Example 67A.1), 173 mg (1.25 mmol) $K_2CO_3$, and 120 mg (0.94 mmol) 3-chlorophenol (Fluka) are heated in 2 ml DMSO for 3 h to 90° C. The reaction mixture is distributed between 20 ml water and 20 ml ethyl acetate, and the aqueous phase separated and extracted with 2 portions of ethyl acetate. The organic phase is washed with water and brine, dried ($MgSO_4$), and concentrated by evaporation. The residue is dissolved in ≈15 ml THF, precipitated with hexane, and filtered. Title compound is obtained from the evaporated filtrate after chromatography ($SiO_2$; ethyl acetate/$CH_3OH$, 4:1): m.p.: 143–145° C.; HPLC: $t_{Ret}(Grad_{20-100})$=8.9; FAB MS $(M+H)^+$=348.

The following compounds are prepared in the same manner:

and 14.13 ml (150 mmol) 4-pyridinecarbaldehyde in 120 ml methanol and 75 ml ethyl propionate, 27.8 ml (150 mmol)

| Example | H—X—Y | —X—Y | m.p. [° C.] | HPLC $t_{rel}$ (Grad$_{20-100}$) | FAB MS (M + H)$^+$ |
|---|---|---|---|---|---|
| 72B | 4-chlorophenol (H—O—C₆H₄—Cl)[1] | —O—C₆H₄—Cl | 207–208 | 8.9 | 348 |
| 72C | 4-methylphenol (H—O—C₆H₄—CH₃)[1] | —O—C₆H₄—CH₃ | 175–176 | 8.6 | 328 |
| 72D | 4-methoxyphenol (H—O—C₆H₄—OCH₃)[1] | —O—C₆H₄—OCH₃ | 194–196 | 8.1 | 344 |
| 72E | 4-chlorothiophenol (H—S—C₆H₄—Cl)[1] | —S—C₆H₄—Cl | 204–206 | 9.5 | 364 |

Manufacturer:
[1] Fluka

Example 73

5-(4-Chloroanilino)-8-(4-pyridylmethyl)pyrido[2,3-d]pyridazine

Under N$_2$ atmosphere, a mixture of 1.19 g (8.38 mmol) phosphorus pentoxide, 1.156 g (8.4 mmol) triethylamine hydrochloride, and 1.072 g (8.4 mmol) 4-chloroaniline is heated for 5 min to 200° C. Then 0.50 g (2.1 mmol) 8-(4-pyridylmethyl)-.6H.-pyirdo[2,3-.d.]pyridazin-5-one is added to the melt, and this is stirred for 3 h at 200° C. After cooling, the melt is taken up in 25 ml dichloromethane, 10 ml water, and 5 ml sat. NH$_3$ solution, and the organic phase is separated off, dried (Na$_2$SO$_4$), and concentrated by evaporation. Column chromatography (SiO$_2$; acetate/CH$_3$OH, 50:1→25:1) and crystallization from acetonitrile/methanol yields the title compound: m.p.: 220–222° C.; Anal. calc. (C$_{19}$H$_{14}$N$_5$Cl) C, 65.61%; H, 4.06%; N, 20.14%; found C, 65.7%; H, 4.1%; N, 20.1%; FAB MS (M+H)$^+$=348. The starting material is prepared as follows:

73.1) 6-(Pyridin-4-yl)-[1]pydrindin-5,7-dione

To a suspension of 20.27 g (150 mmol) furo[3,4-b]pyridin-5(7H)-one (for preparation see Synthesis 1997,113) of a 5.4 M solution of sodium methylate in methanol is added dropwise under ice cooling (and N$_2$ atmosphere). The mixture is heated for 15 min to RT and then for 2 h to reflux temperature. The suspension temporarily goes into solution before a solid forms again. After cooling, 120 ml water is added, before stirring, filtering and washing the product with water. Further product is obtainable from the filtrate by acidification with acetic acid: FAB MS (M+H)$^+$=225.

73.2) 8-(4-Pyridylmethyl)-.6H.-pyrido[2,3-.d.]pyridazin-5-one (A) and 5-(4-pyridylmethyl)-.7H.-pyrido[2,3-.d.]pyridazin-8-one (B)

A suspension of 8.7 g (38.8 mmol) 6-(pyridin-4-yl)-[1]pyrindin-5,7-dione in 40 ml hydrazine hydrate is heated for 4 h to reflux. The suspension goes into solution temporarily, then once again a solid precipitates out, which is filtered off after cooling to RT, washed with water and ether, and dried. Fractionated crystallization from boiling methanol leads to mixtures of A and B. Column chromatography (SiO$_2$; ethyl acetate/CH$_3$OH, 19:1→7:3) and stirring in boiling methanol yields A followed by B. A: m.p.: 246–248° C.; $^1$H-NMR (DMSO-d$_6$) 12.83 (s, HN), 9.13 (dd, 1H), 8.59 (dd, 1H), 8.43 (d, 2H), 7.85 (dd, 1H), 7.29 (d, 2H), 4.38 (s, 2H; NOE on signal at 7.29$^{pyridine}$); Anal. calc.($C_{13}H_{10}N_4O$) C, 65.54%; H, 4.23%; N, 23.52%; found C, 65.2%; H, 4.3%; N, 23.5. B: m.p.: >260° C.; $^1$H-NMR (DMSO-$d_6$) 12.83 (s, HN), 9.04 (dd, 1H), 8.46 (d, 2H), 8.33 (dd, 1H), 7.86 (dd, 1H), 7.30 (d, 2H), 4.34 (s, 2H; NOE on signal at 7.29$^{pyridine}$ and 8.33$^{HC-4}$); Anal. calc.($C_{13}H_{10}N_4O$) C, 65.54%; H, 4.23%; N, 23.52%; found C, 65.2%; H, 4.3%; N, 23.5.

Example 74

8-(4-Chloroanilino)-5-(4-pyridylmethyl)pyrido[2,3-d]pyridazine

In the manner described in Example 73, 1.025 g (7.22 mmol) phosphorus pentoxide, 0.994 g (7.22 mmol) triethylamine hydrochloride, 0.921 g (7.22 mmol) 4-chloroaniline, and 0.43 g (1.8 mmol) 5-(4-pyridylmethyl)-.7H.-pyrido[2,3-.d.]-pyridazin-8-one (Example 73.2) is converted to title compound: m.p.: 196–197° C.; Anal. calc.($C_{19}H_{14}N_5Cl$) C, 65.61%; H, 4.06%; N, 20.14%; found C, 65.5%; H, 4.1%; N, 20.1%; FAB MS (M+H)$^+$=348.

Example 75

1-(4-Chloroanilino)-4-(4-pyridylmethyl)pyrido[3,4-d]pyridazine

In the manner described in Example 73, 714 mg (5.03 mmol) phosphorus pentoxide, 694 mg (5.04 mmol) triethylamine hydrochloride, 643 mg (5.04 mmol) 4-chloroaniline, and 300 mg (1.26 mmol) 4-(4-pyridylmethyl)-.2H.-pyrido[3,4-.d.]-pyridazin-1-one is converted to title compound: m.p.: 227–228° C.; HPLC: $t_{Ref}$(Grad$_{5-40}$)=9.1; FAB MS (M+H)$^+$=348. The starting material is prepared as follows:

75.1) 6-(Pyridin-4-yl)-[2]pyrindin-5,7-dione

In the manner described in Example 73.1, title compound is prepared from 4.44 g (32.9 mmol) of a mixture of furo[3,4-c]pyridin-1(3H-one and furo[3,4-c]pyridin-3(1H)-one [for preparation see *Can. J. Chem.* 64 (1986), 1031] and 3.1 ml (32.9 mmol) 4-pyridinecarbaldehyde in 26 ml methanol and 16.4 ml ethyl propionate with 6.1 ml (32.9 mmol) sodium methylate 5.4 M in methanol: FAB MS (M+H)$^+$=225.

75.2) 4-(4-Pyridylmethyl)-.2H.-pyrido[3,4-.d.] pyridazin-1-one (A) and 1-(4-pyridylmethyl).3H.-pyrido[2,3-.d.]pyridazin-4-one (B)

2.69 g (12 mmol) 6-(pyridin-4-yl)-[2]pyrindin-5,7-dione in 12 ml hydrazine hydrate is heated for 3 h to reflux. After cooling to 5° C., the mixture is filtered off, washed with water and ether, and dried. Column chromatography (SiO$_2$, applied as solution in dichloromethane/methanol; eluent: toluene/isopropanol 19:1→toluene/isopropanol/NH$_3$(aq) 90:10:0.25→90:20:0.5) and crystallization from isopropanol yields A followed by B. A: m.p.: 236–237° C.; $^1$H-NMR (DMSO-$d_6$) 12.9 (s, HN), 9.32 (s, 1H), 8.96 (d, 1H), 8.47 (d, 2H), 8.08 (d, 1H), 7.34 (d, 2H), 4.43 (s, 2H; NOE on singlet at 9.32); FAB MS (M+H)$^+$=239. B: $^1$H-NMR (DMSO-$d_6$) 12.93 (s, HN), 9.45 (s, 1H), 9.00 (d, 1H), 8.47 (d, 2H), 7.80 (d, 1H), 7.33 (d, 2H), 4.34 (s, 2H; NOE on doublet at 7.80); FAB MS (M+H)$^+$=239.

Example 76

4-(4-Chloroanilino)-1-(4-pyridylmethyl)pyrido[3,4-d]pyridazine

In the manner described in Example 73, 714 mg (5.03 mmol) phosphorous pentoxide, 694 mg (5.04 mmol) triethylamine hydrochloride, 643 mg (5.04 mmol) 4-chloroaniline, and 300 mg (1.26 mmol) 1-(4-pyridylmethyl)-.3H.-pyrido[3,4-d]-pyridazin-4-one (Example 75.2) is converted to title compound: m.p.: 220–221° C.; HPLC: $t_{Ref}$(Grad$_{5-40}$)=9.3; FAB MS (M+H)$^+$=348.

Example 77 rac Benzoic acid-[4-(4-chloroanilino)phthalazin-1-yl](pyridin-4-yl)methyl ester

Under N$_2$ atmosphere, a solution of 500 mg (1.29 mmol) 2-benzoyl-4-(4-chloroanilino)-1,2-dihydrophthalazine-1-carbonitrile in 13 ml THF is mixed with 1.94 ml (1 M in THF; 1.94 mmol) lithium-bis(trimethylsilyl)amide at −70° C. and stirred for 60 min. Then 2.13 ml (1 M in THF; 2.13 mmol) freshly distilled 4-pyridinecarbaldehyde is added, stirred for 3 h, and the solution poured on ice water. Extraction with Acetate, washing with brine, drying (Na$_2$SO$_4$) and column chromatography (SiO$_2$; toluene/acetone 3:1→2:1) yield the title compound: m.p. 183–185° C., HPLC: $t_{Ref}$(Grad$_{20-100}$)=8.4; FAB MS (M+H)$^+$=467. The starting material is prepared as follows:

77.1) 1-(4-Chloroanilino)phthalazine 30 g (149 mmol) 1-chlorophthalazine (prepared from phthalazone in the manner described under Example 67A.1) and 20 g (157 mmol) 4-chloroaniline are heated in 630 ml n-butanol for 30 min to 65° C. The crude product is filtered off, washed with ether, taken up in 2 l dichloromethane/methanol 9:1, and washed with sat. NaHCO$_3$ solution and brine. The aqueous phases are extracted three times with dichloromethane/methanol 9:1, the organic phases dried (Na$_2$SO$_4$), and evaporated to a residual volume of ≈50 ml, leading to crystallization of the title compound: m.p.: 211° C.; Anal. calc.($C_{14}H_{10}N_3Cl$) C, 65.76%; H, 3.94%; N, 16.43%; Cl, 13.86%; found C, 66.02%; H, 3.92%; N, 16.53%; Cl, 13.51%.

77.2) 2-Benzoyl-4-(4-chloroanilino)-1,2-dihydrophthalazine-1-carbonitrile

Under N$_2$ atmosphere, first 164 mg (1.2 mmol) anhydrous aluminium chloride is added to 12.6 g (49.3 mmol) 1-(4-chloroanilino)phthalazine in 90 ml dichloromethane, followed by 12.3 ml (98.6 mmol) trimethylsilyl cyanide. Finally, 11.5 ml (98.6 mmol) benzoyl chloride is added under ice cooling and stirred for 3 h at RT. The suspension is poured onto 0.6 ml water, filtered off, washed with water, and dried. Mixing in 150 ml boiling ethanol yields pure title compound: m.p.: 201–202° C.; Anal. calc.($C_{22}H_{15}N_4ClO$) C, 68.31%; H, 3.91%; N, 14.48%, Cl, 9.16%; found C, 68.03%; H, 3.89%; N, 14.22%; Cl, 9.42%.

Example 78 rac [4-(4-Chloroanilino)phthalazin-1-yl](pyridin-4-yl)methanol 100 mg (0.214 mMol) of rac benzoic acid-[4-(4-chloroanilino)phthalazin-1-yl](pyridin-4-yl)-methyl ester in 2 ml dioxane, 1 ml methanol and 1 ml water are saponified with 9.9 mg (0.235 mmol) lithiumhydroxide monohydrate. After 16 h, the title compound is filtered off: m.p. 196–197° C., FAB MS (M+H)$^+$=363.

Example 79

The following compounds are prepared in the same manner as described in this disclosure, especially in the Examples mentioned herein before and hereinafter:
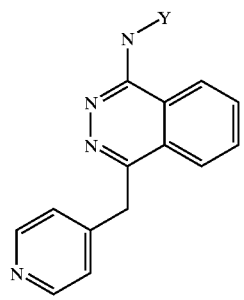
| Example | H₂N—Y | —HN-Y |
|---|---|---|
| 79A | 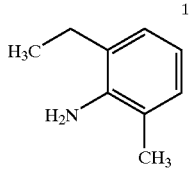 1 | 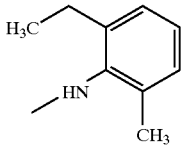 |
| 79B | 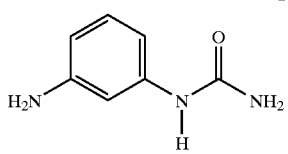 2 | 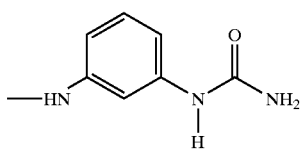 |
| 79C | 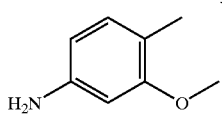 3 | 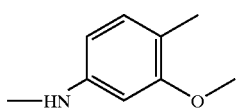 |
| 79D | 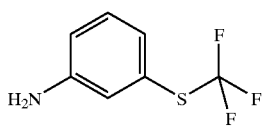 4 | 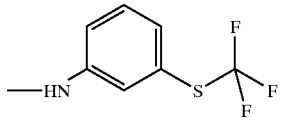 |
| 79E | 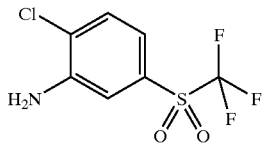 5 | 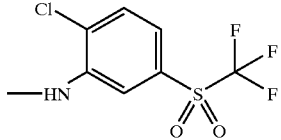 |
| 79F | 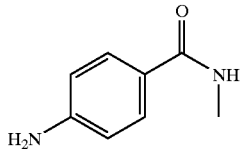 6 | 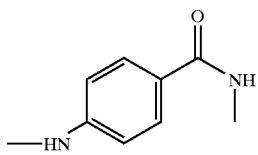 |
| 79G | 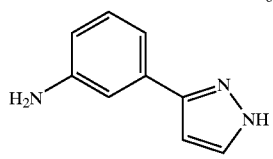 6 | 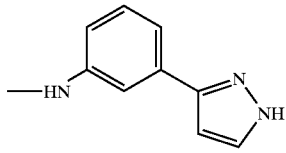 |

-continued
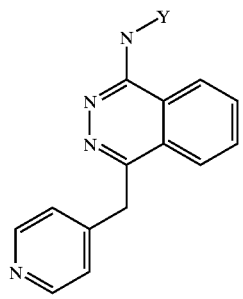
| Example | H₂N—Y | —HN-Y |
|---|---|---|
| 79H | 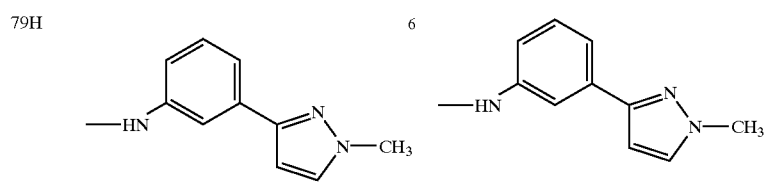 | |
| 79I | 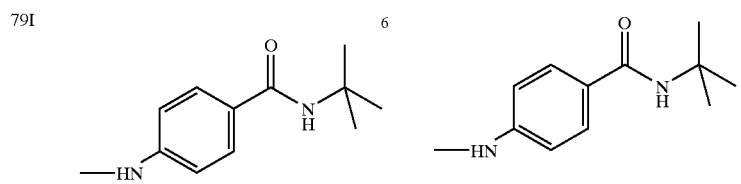 | |
| 79J | 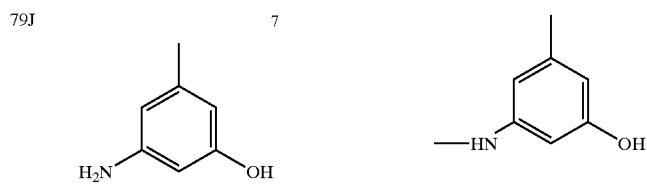 | |
| 79K | 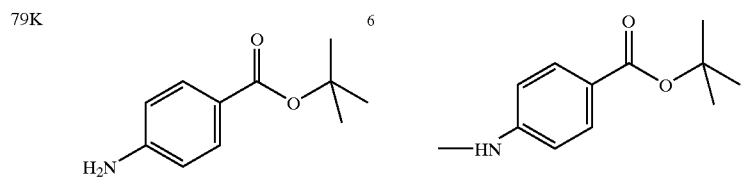 | |
| 79L | 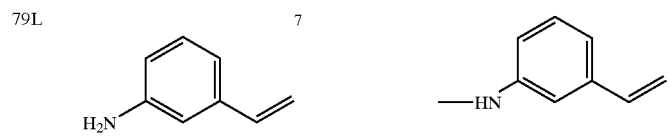 | |
| 79M | 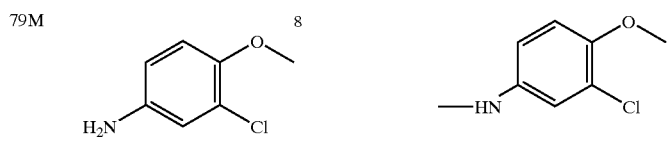 | |
| 79N | 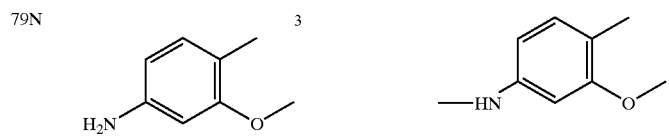 | |

-continued

| Example | H₂N—Y | —HN—Y |
|---|---|---|
| 79O | (3,5-bis(trifluoromethyl)aniline) | 1 (3,5-bis(trifluoromethyl)phenyl-NH) |

Manufacturers:
[1]Fluka;
[2]Bayer;
[3]Merck;
[4]JRD Fluorochemicals;
[5]Maybridge;
[6]Butt Park;
[7]ICN;
[8]Aldrich.

Example 80

Test for Activity Against Flt-1 VEGF-receptor Tyrosine Kinase

The test is conducted using Flt-1 VEGF-receptor tyrosine kinase, as described hereinabove. The IC$_{50}$ values determined are given below, insofar as they have been accurately recorded:

| Title compound from Example | IC$_{50}$ ($\mu$M) |
|---|---|
| 1 to 4 | 0.1 to 0.26 |
| 5 | 0.21 |
| 6 | 0.23 |
| 7 | 0.64 |
| 8 | 0.33 |
| 9 | 0.97 |
| 10 | 0.2 |
| 14 | 0.74 |
| 16 | 0.52 |
| 17 | 0.29 |
| 18 | 0.21 |
| 19 | 0.73 |
| 20 | 0.5 |
| 21 | 0.41 |
| 22 | 0.18 |
| 23 | 0.515 |
| 24 | 0.666 |
| 32A | 0.042 |
| 32B | 1 |
| 32D | 0.48 |
| 32F | 0.793 |
| 37 | 0.154 |
| 39 | 0.251 |
| 42 | 0.211 |
| 43 | 9.07 |
| 44A | 0.277 |
| 44B | 0.234 |
| 44C | 0.042 |
| 44D | 0.317 |
| 44E | 0.49 |
| 44F | 0.624 |
| 44H | 11.4 |
| 45 | 0.345 |
| 46 | 0.349 |
| 47 | 0.188 |
| 48 | 0.549 |
| 50 | 0.195 |
| 53 | 1.04 |
| 56 | 1 |
| 57 | 16 |
| 58 | 7.3 |
| 64 | 0.907 |
| 66 | 2.4 |
| 67B | 0.335 |
| 67D | 0.401 |
| 67E | 0.44 |
| 67F | 1.2 |
| 67H | 0.615 |
| 67Q | 0.328 |
| 67S | 1.2 |
| 69 | 0.742 |
| 70A | 1 |
| 70B | 1 |

-continued

| Title compound from Example | IC$_{50}$ ($\mu$M) |
|---|---|
| 72A | 1.27 |
| 72B | 0.284 |
| 72C | 0.747 |
| 72D | 0.593 |
| 72E | 1.2 |
| 73 | 0.397 |
| 74 | 1 |
| 75 | 1 |
| 76 | 3.2 |
| 82A | 0.478 |
| 82B | 0.774 |
| 82E | 2.5 |

With the other compounds, insofar as they were measured, no accurate IC$_{50}$ values were determined, but these usually lie above 1 $\mu$M.

Example 81
In vivo Activity in the Nude Mouse Xenotransplant Model (A-431 Tumours):

Using the test system described in the introductory section, tumour volumes are measured with and without administration of the title compound from Example 1 (dissolved in water). Measurement is carried out on Day 5 after tumour transplantation, and thereafter twice a week, until the final measurement 24 h after the end of treatment (Day 28 after the start of treatment). Six animals are used per dose.

Example 82

The following compounds are prepared as described below:

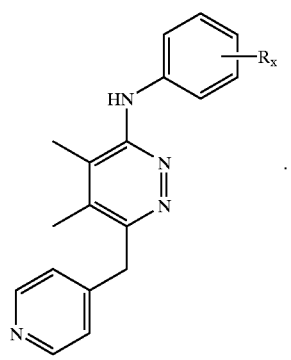

A: $R_x$ = 4-Cl
B: $R_x$ = 4-CH$_3$
C: $R_x$ = 4-OCH$_3$
D: $R_x$ = 3-Cl
E: $R_x$ = 3-CH$_3$

Preparation of 82A=3-(4-chloroanilino)-4,5-dimethyl-6-(pyridin-4-yl)methylpyridazine ($R_x$= para-chloro)

A solution of 0.070 g 3-chloro-4,5-dimethyl-6-(pyridin-4-yl)methylpyridazine and 0.153 g para-chloroaniline is heated in a sealed tube for 20 h to 130° C. After cooling to RT, the solution is concentrated by evaporation, the residue diluted with 100 ml CH$_2$Cl$_2$ and then extracted with 100 ml sat. aqueous NaHCO$_3$ solution. The organic phase is dried over MgSO$_4$, concentrated by evaporation, and the residue purified by flash chromatography (FC) on silica gel in Ch$_2$Cl$_2$/methanol 19/1. The title compound is obtained: m.p. 196–199° C. $^1$H-NMR (250 MHz, CDCl$_3$): δ=8.45 (s, wide, 2H); 7.55 (d, 2H); 7.25 (d, 2H); 7.10 (d, 2H); 6.20 (s, wide, 1H); 4.25 (s, 2H); 2.15 (s, 3H); 2.10 (s, 3H). ES-MS 325, 327 (M+H for $^{35}$Cl and $^{37}$Cl).

Preparation of 82B=3-(4-methylanilino)-4,5-dimethyl-6-(pyridin-4-yl)methylpyridazine ($R_x$= para-methyl)

The compound is prepared from 0.070 g 3-chloro-4,5-dimethyl-6-(pyridin-4-yl)methylpyridazine and 0.129 g para-methylaniline in the manner described in Example 82A. Title compound is obtained after FC in CH$_2$Cl$_2$/Methanol 19/1; m.p. 68–70° C. $^1$H-NMR (250 MHz, CDCl$_3$): δ=8.45 (s, wide, 2H); 7.45 (d, 2H); 7.10 ("d", wide, 4H); 6.10 (s, wide, 1H); 4.25 (s, 2H); 2.30 (s, 3H); 2.15 (s, 3H); 2.10 (s, 3H). ES-MS 305 (M+H).

Preparation of 82C=3-(4-methoxyanilino)-4,5-dimethyl-6-(pyridin-4-yl)methylpyndazine ($R_x$= para-methoxy)

The compound is prepared from 0.070 g 3-chloro-4,5-dimethyl-6-(pyridin-4-yl)methylpyridazine and 0.129 g para-methoxyaniline in the manner described in Example 82A. Title compound is obtained after FC in CH$_2$Cl$_2$/Methanol 19/1. $^1$H-NMR (250 MHz, CDCl$_3$): δ=8.45 (d, 2H); 7.45 (d, 2H); 7.10 (d, 2H); 6.85 (d, 2H); 6.05 (s, wide, 1H); 4.25 (s, 2H); 3.80 (s, 3H); 2.30 (s, 3H); 2.15 (s, 3H); 2.10 (s, 3H). ES-MS 321 (M+H).

Preparation of 82D=3-(3-chloroanilino)-4,5-dimethyl-6-(pyridin-4-yl)methylpyridazine ($R_x$= meta-chloro)

The compound is prepared starting from 0.070 g 3-chloro-4,5-dimethyl-6-(pyridin-4-yl)methylpyridazine and 0.153 g meta-chloroaniline in the manner described in Example 82A. After heating for 20 h to 130° C., siginificant quantities of 3-chloro-4,5-dimethyl-6-(pyridin-4-yl)methylpyridazine are still present (TLC). For this reason, a further 0.153 g meta-chloroaniline is added and heated for another 24 h to 130° C. Processing is in the manner described for Example 82A. Title compound is obtained after FC in CH$_2$Cl$_2$/methanol 19/1: m.p. 164–167°. $^1$H-NMR (250 MHz, CDCl$_3$): δ=8.45 (s, wide, 2H); 7.70 (t, 1H); 7.45 (dd, 1H); 7.25–7.10 (m, 3H)); 7.00 (dd, 1H); 6.20 (s, wide, 1H); 4.25 (s, 2H); 2.15 (s, 3H); 2.10 (s, 3H). ES-MS 325, 327 (M+H for $^{35}$Cl and $^{37}$Cl).

Preparation of 82E=3-(3-methylanilino)-4,5-dimethyl-6-(pyridin-4-yl)methylpyridazine ($R_x$= meta-methyl)

The compound is prepared starting from 0.070 g 3-chloro-4,5-dimethyl-6-(pyridin-4-yl)methylpyridazine and 0.129 g meta-methylaniline in the manner described in Example 82A. After heating for 20 h to 130° C., significant quantities of 3-chloro-4,5-dimethyl-6-(pyridin-4-yl)methylpyridazine are still present (TLC). For this reason, a further 0.129 g meta-methylaniline is added and heated for another 24 h to 130° C. Processing is in the manner described for Example 82A. Title compound of about 90% purity is obtained after FC in CH$_2$Cl$_2$/methanol 19/1; m.p. 68–90%°. $^1$H-NMR (250

MHz, CDCl$_3$): δ=8.45 (d, 2H); 7.70 (t, 1H); 7.50 (s, 1H); 7.40–7.10 (m, 4H)); 6.90 (d, 1H); 6.15 (s, wide, 1H); 4.30 (s, 2H); 2.35 (s, 3H); 2.15 (s, 3H); 2.10 (s, 3H). ES-MS 305 (M+H). The starting material is prepared as follows:

82.1) 2H-3-Oxo-4,5-dimethyl-6-(pyridin-4-yl) methylpyridazine

To a solution of 26.1 ml diisopropylamine in 200 ml THF, 124 ml of a 1.6 M solution of butyl lithium in THF is added at 0° C. At −20 to −30° C., a solution of 19.3 ml 4-picoline in 200 ml THF is then added dropwise and stirred for 60 min at −30° C. To the yellow solution, a solution of 10 g maleic acid anhydride in 100 ml THF is then added dropwise at −78° C. and subsequently stirred for 1 h at −78° C. and for 2 h at RT. The reaction mixture is then mixed with 500 ml 2N HCl and washed twice with acetate. The aqueous phase is then concentrated by evaporation, the pH adjusted to alkaline with 2N NaOH, and washed again twice with acetate. The aqueous solution is then acidified again with 2N HCl and concentrated by evaporation. The orange residue obtained in this way is filtered via silica gel (CH$_2$Cl$_2$/MeOH, 5/1), and the material obtained ($^1$H-NMR (250 MHz, CDCl$_3$): δ=3.20 (s, 2H); 1.25 (s, 3H); 1.20 (s, 3H). ES-MS 220 (M+H)) processed without further purification.

A solution of 2 g of the crude product obtained above and 1.11 ml hydrazine hydrate in 2 ml n-butanol is heated under nitrogen for 2 h to 1 20° C. After cooling to RT, the resulting emulsion is concentrated by evaporation, mixed with a little water, and then extracted three times with CH$_2$Cl$_2$. The organic phases are filtered via cottonwool, concentrated by evaporation, and the resulting yellow oil dissolved in CH$_2$Cl$_2$ and precipitated with diisopropyl ether. The title compound is obtained in the form of white crystals.

$^1$H-NMR (250 MHz, CDCl$_3$): δ=8.55 (dd, 2H); 7.10 (d, 2H); 3.95 (s, 2H); 2.15 (s, 3H); 2.00 (s, 3H). ES-MS 216 (M+H).

82.2) 3-Chloro-4,5-dimethyl-6-(pyridin-4-yl) methylpyridazine

A solution of 0.700 g of title compound from 82.1 in 7 ml POCl$_3$ is heated for 3 h to 120° C. For processing, the resulting suspension is first poured onto ice water and the pH adjusted to alkaline with 2N NaOH before extraction three times with CH$_2$Cl$_2$. The combined organic phases are filtered through Cottonwood, concentrated by evaporation, and the residue purified by FC on silica gel in the eluent system CH$_2$Cl$_2$/methanol 19/1. The title compound is obtained in the form of brown crystals: $^1$H-NMR (250 MHz, CDCl$_3$): δ=8.50 (dd, 2H); 7.10 (d, 2H); 4.25 (s, 2H); 2.35 (s, 3H); 2.15 (s, 3H). ES-MS 234, 236 (M+H for $^{35}$Cl and $^{37}$Cl).

Example 83 rac Benzoic acid-{1-[4-(4-chloroanilino)phthalazin-1-yl]-3-(pyridin-4-yl)propyl} ester Preparation starting from 2-benzoyl-4-(4-chloroanilino)-1,2-dihydrophthalazine-1-carbonitrile and 3-(pyridin-4-yl) propionaldehyde as described in Example 77 yields the title compound: FAB-MS (M+H)$^+$=495.

Example 84

1-(4-Chloroanilino)-4-[3-(4-pyridyl)propyl]-phthallazine

Hydrogenation of rac benzoic acid-{1-[4-(4-chloroanilino)phthalazin-1-yl]-3-(pyridin-4-yl)propyl} ester yields the title compound

Example 85

Soft Capsules 5000 soft gelatin capsules, each comprising as active ingredient 0.05 g of one of the compounds of formula I mentioned in the preceding Examples, are prepared as follows:

| Composition | |
| --- | --- |
| Active ingredient | 250 g |
| Lauroglycol | 2 liters |

Preparation process: The pulverized active ingredient is suspended in Lauroglykol® (propylene glycol laurate, Gattefossé S. A., Saint Priest, France) and ground in a wet pulverizer to produce a particle size of about 1 to 3 μm. 0.419 g portions of the mixture are then introduced into soft gelatin capsules using a capsule-filling machine.

Example 86

Soft Capsules 5000 soft gelatin capsules, each comprising as active ingredient 0.05 g of one of the compounds of formula I mentioned in the preceding Examples, are prepared as follows:

| Composition | |
| --- | --- |
| Active ingredient | 250 g |
| PEG 400 | 1 liter |
| Tween 80 | 1 liter |

Preparation Process

The pulverized active ingredient is suspended in PEG 400 (polyethylene glycol with M$_r$ between about 380 and about 420, Fluka, Switzerland) and Tween® 80 (polyoxyethylene sorbitan mono-oleate, Atlas Chem. Ind., Inc., USA, supplied by Fluka, Switzerland) and ground in a wet pulverizer to produce a particle size of about 1 to 3 μm. 0.43 g portions of the mixture are then introduced into soft gelatin capsules using a capsule-filling machine.

Example 87

Formulation in Klucel

2After micronization, the compound from Example 62 is formulated in aqueous Klucel HF (0.5%), active ingredient (free base) being present in a concentration of 7 mg/ml. Estimates of particle size lay at a mean of about 5 μm, within a range of about 3 to 12 μm.

What is claimed is:

1. A compound of formula I

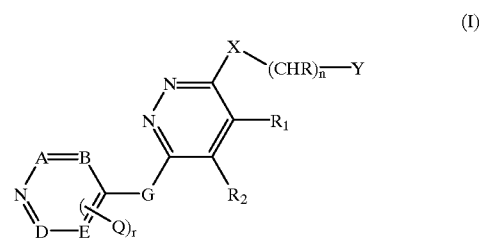

(I)

wherein
r is 0 to 2;
n is 0;
R¹ and R₂ together form a bridge in subformula I**

(I**)

wherein
one or two of the ring members $T_1$, $T_2$, $T_3$ and $T_4$ are nitrogen, and the others are in each case CH, and the binding is achieved via $T_1$ and $T_4$;
A, B, D and E are, independently of one another, N or CH, with the stipulation that not more than 2 of these radicals are N;
G is lower alkyene;
Q is methyl, which is bound to A, to D, or to A and D;
R is H or lower alkyl;
X is imino;
Y is phenyl, which is unsubstituted or substituted by one or two substituents independently of one another selected from the group consisting of amino, lower alkanoyl-amino, halogen, lower alkyl, halogen-lower alkyl, hydroxy, lower alkoxy, phenyl-lower alkoxy and cyano; or pyridyl; or a salt thereof.

2. A compound according to claim 1 wherein the salt is one which is pharmaceutically acceptable.

3. A compound according to claim 1 selected from the group consisting of 5-(4-chloroanalino)-8-(4-pyridylmethyl)pyrido[2,3-d]pyridazine, 8-(4-chloroanalino)-5-(4-pyridylmethyl)pyrido[2,3-d]pyridazine, 1-(4-chloroanalino)-4-(4-pyridylmethyl)pyrido[3,4-d]pyridazine and 4-(4-chloroanalino)-1-(4-pyridylmethyl)pyrido[3,4-d]pyridazine, or a pharmaceutically acceptable salt thereof.

4. A pharmaceutical composition comprising at least one pharmaceutically acceptable carrier and a therapeutically effective amount of a compound of claim 1, or a pharmaceutically acceptable salt thereof.

5. A compound according to claim 1 wherein r is 0; m is 0; A, B, D and E are in each case CH; G is lower alkylene; R is H; X is imino; and Y is phenyl, which is unsubstituted or substituted by one or two substituents independently of one another selected from the group consisting of amino, lower alkanoyl-amino, halogen, lower alkyl, halogen-lower alkyl, hydroxy, lower alkoxy, phenyl-lower alkoxy and cyano; or a salt thereof.

6. A compound according to claim 1 wherein r is 0; m is 0; A, B, D and E are in each case CH; G is methylene; R is H; X is imino; and Y is selected from the group consisting of phenyl, 2-, 3- or 4-aminophenyl, 2-, 3- or 4-acetylaminophenyl, 2-, 3- or 4-fluorophenyl, 2-, 3- or 4-chlorophenyl, 2-, 3- or 4-bromophenyl, 2,3-, 2,4-, 2,5- or 3,4-dichlorophenyl, chlorofluorophenyl, 2-, 3- or 4-methylphenyl, 2-, 3- or 4-trifluoromethylphenyl, 2-, 3- or 4-hydroxyphenyl, 2-, 3- or 4-methoxyphenyl, methoxychlorophenyl, 2-, 3- or 4-benzyloxyphenyl, or 2-, 3- or 4-cyanophenyl; or a salt thereof.

7. A compound according to claim 5 wherein the salt is one which is pharmaceutically acceptable.

8. A compound according to claim 6 wherein the salt is one which is pharmaceutically acceptable.

* * * * *

UNITED STATES PATENT AND TRADEMARK OFFICE
CERTIFICATE OF CORRECTION

PATENT NO. : 6,514,974 B2
DATED : February 4, 2003
INVENTOR(S) : Bold et al.

It is certified that error appears in the above-identified patent and that said Letters Patent is hereby corrected as shown below:

Title page,
Item [62], Related U.S. Application Data, should read:

-- Related U.S. Application Data

(62) Division of application No 09/367,273, having a 35 USC 371 date of Oct. 20, 1999, now issued as U.S. Pat No. 6,258,812, which is a 371 of International Application No. PCT/EP98/00764, filed Feb. 11, 1998. --.

Signed and Sealed this

Twenty-sixth Day of August, 2003

JAMES E. ROGAN
*Director of the United States Patent and Trademark Office*